United States Patent
Ueda et al.

(10) Patent No.: US 6,268,310 B1
(45) Date of Patent: Jul. 31, 2001

(54) OXAZOLE DERIVATIVE, PROCESS FOR PRODUCING THE SAME, AND HERBICIDE

(75) Inventors: Akiyoshi Ueda, Kanagawa; Yasuyuki Miyazawa, Nakago-mura; Yoshihiko Hara, Ooiso-machi; Masami Koguchi, Kanagawa; Akihiro Takahashi, Kanagawa; Takashi Kawana, Kanagawa, all of (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 09/248,372

(22) Filed: Feb. 10, 1999

Related U.S. Application Data

(63) Continuation-in-part of application No. 08/750,932, filed on Jan. 28, 1997, now Pat. No. 5,962,685.

(51) Int. Cl.$^7$ .................. C07D 413/12; A01N 43/54
(52) U.S. Cl. .................. 504/242; 504/243; 544/300; 544/310; 544/316; 544/317
(58) Field of Search .................. 544/300, 310, 544/316, 317; 504/242, 243

(56) References Cited

U.S. PATENT DOCUMENTS

| | | | |
|---|---|---|---|
| 4,248,618 | * | 2/1981 | Serban et al. ............................. 71/92 |
| 4,423,047 | * | 12/1983 | Benneche ............................. 424/251 |
| 4,427,437 | * | 1/1984 | Serban et al. ............................. 71/92 |

\* cited by examiner

Primary Examiner—John M. Ford

(74) *Attorney, Agent, or Firm*—Joseph C. Mason, Jr.; Dennis G. LaPointe; Mason & Assoc., P.A.

(57) ABSTRACT

The present invention is directed to oxazole derivatives represented by the formula [I];

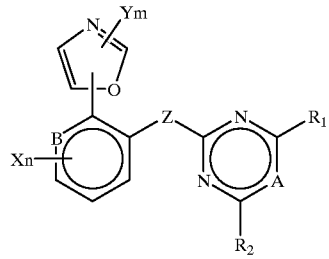

(I)

wherein A represents a nitrogen atom or a $R_3$-substituted carbon atom; B represents a nitrogen atom, or an unsubstituted or X-substituted carbon atom; Z represents an oxygen atom, sulfinyl or sulfonyl; $R_1$ and $R_2$ represent each independently hydrogen, $C_1$–$C_6$ alkyl, $C_1$–$C_6$ alkoxy, $C_1$–$C_6$ haloalkoxy, $C_1$–$C_6$ haloalkyl or the like; $R_3$ represents hydrogen, $C_1$–$C_6$ alkyl, halogen, nitro, formyl or acyl; X represents hydrogen, $C_1$–$C_6$ alkyl, $C_3$–$C_7$ cycloalkyl, $C_2$–$C_6$ alkenyl, $C_3$–$C_6$ alkynyl, $C_1$–$C_6$ haloalkyl or the like; Y represents hydrogen, $C_1$–$C_6$ alkyl, $C_3$–$C_7$ cycloalkyl, $C_2$–$C_6$ alkenyl, $C_3$–$C_6$ alkynyl, $C_1$–$C_6$ haloalkyl or the like; m represents an integar of 1 or 2, and n represents an integar of 1, 2, 3 or 4, and the salts thereof. The compounds specified in the present invention have an excellent herbicidal activity and are useful as an active ingredients for herbicides.

2 Claims, No Drawings

OXAZOLE DERIVATIVE, PROCESS FOR PRODUCING THE SAME, AND HERBICIDE

RELATED APPLICATION

This is a continuation in part application of U.S. patent application Ser. No. 08/750,932 filed Jan. 28, 1997, now U.S. Pat. No. 5,962,685.

FIELD OF THE INVENTION

The present invention relates to novel oxazole derivatives, process for producing said oxazole derivatives, and herbicides comprising said derivative(s) as the active ingredient(s) thereof.

BACKGROUND ART

In cultivation of agricultural and horticultural crops, herbicides have been used for weed control for which enormous labours have been required. However, such herbicides have often caused phytotoxicity on crops, have remained as residues in the environment and have been therefore a cause of environmental pollution. From such reasons, a development of herbicides, which can give firm herbicidal effectiveness with a lower dose and can be used without a problem of phytotoxicity, environmental residue and environmental pollution, has been required intensively.

Pyrimidyloxy-substituted salicylic acids similar to the compounds of the present invention and the sulfur homologs thereof are disclosed in Japanese Patent laid-open Nos. Sho 59-59669, Sho 62-174059, Hei 3-232884, Hei 4-77487, etc., however, there is no compound which has a satisfactory herbicidal-effect and a selectivity to crop plants.

In Japanese patent laid-open No. Hei 5-202038, it is disclosed that compounds represented by the following chemical formula;

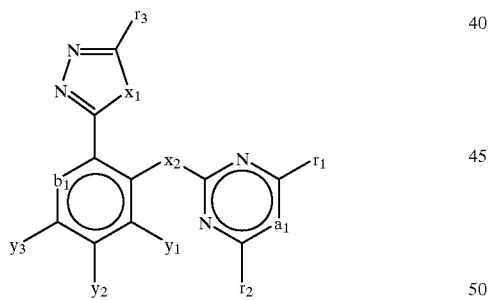

where in $r_1$ and $r_2$ represent each independently lower alkyl or lower alkoxy; $r_3$ represents lower alkyl or the like; $x_1$ and $x_2$ represent each independently O or S; $a_1$ represents CH or N; $y_1$, $y_2$ and $y_3$ represent each independently H or the like; and $b_1$ represents CH or N, have a herbicidal effect.

It is an object of the present invention to provide herbicides which can be easily produced in an industrial scale, safe and excellent in herbicidal activity at a lower dose, and have excellent selectivity to various agricultural and horticultural crops.

DISCLOSURE OF THE INVENTION

The present invention is directed to oxazole derivatives represented by a general formula [I];

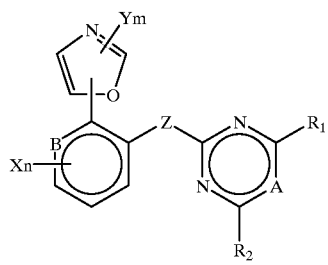

wherein A represents a nitrogen atom or a $R_3$-substituted carbon atom;

B represents a nitrogen atom, or an unsubstituted or X-substituted carbon atom;

Z represents an oxygen atom, sulfur, sulfinyl or sulfonyl;

$R_1$ and $R_2$ represent each independently hydrogen, $C_1$–$C_6$ alkyl, $C_1$–$C_6$ alkoxy, $C_1$–$C_6$ haloalkoxy, $C_1$–$C_6$ haloalkyl, $C_1$–$C_6$ alkylamino, di-($C_1$–$C_6$ alkylamino), $C_1$–$C_6$ alkylthio, halogen or cyano;

$R_3$ represents hydrogen, $C_1$–$C_6$ alkyl, halogen, nitro, formyl or acyl;

X represents hydrogen, $C_1$–$C_6$ alkyl, $C_3$–$C_7$ cycloalkyl, $C_2$–$C_6$ alkenyl, $C_3$–$C_6$ alkynyl, $C_1$–$C_6$ haloalkyl, benzyl optionally substituted with halogen, $C_1$–$C_6$ alkyl, halo $C_1$–$C_6$ alkyl, nitro, cyano, $C_1$–$C_6$ alkoxy, amino, $C_1$–$C_6$ alkylamino, di-($C_1$–$C_6$ alkylamino) or $C_1$–$C_6$ acyl; phenyl substituted with hydrogen, halogen, $C_1$–$C_6$ alkyl, halo $C_1$–$C_6$ alkyl, nitro, cyano, $C_1$–$C_6$ alkoxy, amino, $C_1$–$C_6$ alkylamino, di-($C_1$–$C_6$ alkylamino) or $C_1$–$C_6$ acyl; $C_1$–$C_6$ alkoxy $C_1$–$C_6$ alkyl, $C_1$–$C_6$ alkylthio $C_1$–$C_6$ alkyl, phenoxy $C_1$–$C_6$ alkyl, phenylthio $C_1$–$C_6$ alkyl, $C_1$–$C_6$ alkylsulfinyl $C_1$–$C_6$ alkyl, $C_1$–$C_6$ alkylsulfonyl $C_1$–$C_6$ alkyl, phenylsulfonyl $C_1$–$C_6$ alkyl, halo $C_1$–$C_6$ alkylsulfonyl $C_1$–$C_6$ alkyl, cyano $C_1$–$C_6$ alkyl, halogen, nitro, amino, $C_1$–$C_6$ alkylamino, di-($C_1$–$C_6$ alkylamino), acylamino, $C_1$–$C_6$ alkylsulfonylamino, formyl, $C_1$–$C_6$ acyl, cyano, carboxyl, hydroxyl, $C_1$–$C_6$ alkoxycarbonyl, $C_1$–$C_6$ alkylthiocarbonyl, $C_1$–$C_6$ acyl $C_1$–$C_6$ alkoxymoyl, $C_1$–$C_6$ acylimidoyl, carbamoyl, $C_1$–$C_6$ alkoxy, $C_2$–$C_6$ alkenyloxy, $C_3$–$C_6$ alkynyloxy, $C_1$–$C_6$ alkoxy $C_1$–$C_6$ alkoxy, halo $C_1$–$C_6$ alkoxy, $C_1$–$C_6$ alkylthio $C_1$–$C_6$ alkoxy, $C_1$–$C_6$ alkylsulfonyloxy, halo $C_1$–$C_6$ alkylsulfonyloxy, $C_1$–$C_6$ alkoxy substituted with $C_1$–$C_6$ alkoxycarbonyl, thiol, $C_1$–$C_6$ alkylthio, $C_1$–$C_6$ alkylsulfonyl, $C_2$–$C_6$ alkenylthio, $C_3$–$C_6$ alkynylthio, acyloxy, carbamoyloxy, thiocarbamoyloxy, benzyloxy, phenoxy optionally substituted with halogen, $C_1$–$C_6$ alkyl, halo $C_1$–$C_6$ alkyl, nitro, cyano, $C_1$–$C_6$ alkoxy, amino, $C_1$–$C_6$ alkylamino, di-($C_1$–$C_6$ alkylamino) or $C_1$–$C_6$ acyl; phenylthio substituted with hydrogen, halogen, $C_1$–$C_6$ alkyl, halo $C_1$–$C_6$ alkyl, nitro, cyano, $C_1$–$C_6$ alkoxy, amino, $C_1$–$C_6$ alkylamino, di($C_1$–$C_6$ alkyl)amino or $C_1$–$C_6$ acyl; phenylsulfonyloxy, benzoyloxy, phenylsulfonyl, oxyheterocycle, thioheterocycle, benzoyl or heterocycle group, hydroxymoyl, hydroxy $C_1$–$C_6$ alkyl, halo $C_1$–$C_6$ alkylsulfonyloxy or carbohydrazonoyl;

or two groups represented by X may combine to form a saturated or unsaturated carbon ring or heterocycle, Y represents hydrogen, $C_1$–$C_6$ alkyl, $C_3$–$C_7$ cycloalkyl, $C_2$–$C_6$ alkenyl, $C_3$–$C_6$ alkynyl, $C_1$–$C_6$ haloalkyl, benzyl optionally substituted with halogen, $C_1$–$C_6$ alkyl, $C_1$–$C_6$ haloalkyl, nitro, cyano, $C_1$–$C_6$ alkoxy, amino, $C_1$–$C_6$ alkylamino, di($C_1$–$C_6$ alkyl)amino or $C_1$–$C_6$ acyl; phenyl optionally substituted with halogen, $C_1$–$C_6$ alkyl, halo $C_1$–$C_6$ alkyl, nitro, cyano, $C_1$–$C_6$ alkoxy, amino, $C_1$–$C_6$ alkylamino, di($C_1$–$C_6$ alkyl) amino or $C_1$–$C_6$ acyl; $C_1$–$C_6$ alkoxy $C_1$–$C_6$ alkyl, $C_1$–$C_6$ alkylthio $C_1$–$C_6$ alkyl, phenoxy $C_1$–$C_6$ alkyl, phenylthio $C_1$–$C_6$ alkyl, $C_1$–$C_6$ alkylsulfinyl $C_1$–$C_6$ alkyl, $C_1$–$C_6$ alkylsulfonyl $C_1$–$C_6$ alkyl, phenylsulfonyl $C_1$–$C_6$ alkyl, $C_1$–$C_6$ acyl, cyano $C_1$–$C_6$ alkyl, halogen, nitro, amino, $C_1$–$C_6$ alkylamino, di($C_1$–$C_6$ alkyl) amino, acylamino, $C_1$–$C_6$ alkylsulfonylamino, formyl, $C_1$–$C_6$ acyl, cyano, carboxyl, hydroxyl, $C_1$–$C_6$ alkoxycarbonyl, $C_1$–$C_6$ alkylthiocarbonyl, $C_1$–$C_6$ acyl $C_1$–$C_6$ alkoxymoyl, $C_1$–$C_6$ acylimidoyl, carbamoyl, $C_1$–$C_6$ alkoxy, $C_2$–$C_6$ alkenyloxy, $C_3$–$C_6$ alkynyloxy, $C_1$–$C_6$ alkoxy $C_1$–$C_6$ alkoxy, $C_1$–$C_6$ alkylthio $C_1$–$C_6$ alkoxy, $C_1$–$C_6$ alkylsulfonyl $C_1$–$C_6$ alkoxy, $C_1$–$C_6$ alkoxy substituted with $C_1$–$C_6$ alkoxycarbonyl, $C_1$–$C_6$ alkylsulfonyloxy, mercapt, $C_1$–$C_6$ alkylthio, $C_1$–$C_6$ alkylsulfonyl, $C_2$–$C_6$ alkenylthio, $C_3$–$C_6$ alkynylthio, acyloxy, carbamoyloxy, thiocarbamoyloxy, benzyloxy, phenoxy substituted with hydrogen, halogen, $C_1$–$C_6$ alkyl, halo $C_1$–$C_6$ alkyl, nitro, cyano, $C_1$–$C_6$ alkoxy, amino, $C_1$–$C_6$ alkylamino, di($C_1$–$C_6$ alkyl)amino or $C_1$–$C_6$ acyl; phenylthio substituted with hydrogen, halogen, $C_1$–$C_6$ alkyl, halo $C_1$–$C_6$ alkyl, nitro, cyano, $C_1$–$C_6$ alkoxy, amino, $C_1$–$C_6$ alkylamino, di($C_1$–$C_6$ alkyl)amino or $C_1$–$C_6$ acyl; phenylsulfonyloxy, benzoyloxy, phenylsulfonyl, oxyheterocycle, thioheterocycle, benzoyl, heterocyclic group, hydroxymoyl, oxyheterocycle $C_1$–$C_6$ alkyl, thioheterocycle $C_1$–$C_6$ alkyl, hydroxy $C_1$–$C_6$ alkyl, halo $C_1$–$C_6$ alkylsulfonyloxy or carbohydrazonoyl;

or, two groups represented by Y bonding to 4- and 5-positions of oxazole ring, respectively, may combine to form a saturated or unsaturated carbon cycle or heterocycle;

m represents an integar of 1 or 2; and n represents an integar of 1, 2, 3 or 4, the salts thereof, methods for producing the derivatives and the salts thereof, and herbicides comprising one or more of such derivatives and/or such salts.

Now, the present invention is described in detail.

In the general formula [I] shown above, A represents a nitrogen atom or a $R_3$-substituted carbon atom; $R_3$ represents hydrogen, $C_1$–$C_6$ alkyl, such as methyl and ethyl, halogen, such as fluorine, chlorine and bromine, nitro, formyl or acyl, such as acetyl, however, hydrogen and methyl can be given as an preferable example.

Z represents an oxygen atom, sulfur, sulfinyl or sulfonyl, and oxygen and sulfur can be given as an preferable example.

$R_1$ and $R_2$ represent each independently hydrogen, $C_1$–$C_6$ alkyl, such as methyl, ethyl and isopropyl, $C_1$–$C_6$ alkoxy, such as methoxy, ethoxy and isopropoxy, $C_1$–$C_6$ haloalkoxy, such as trifluoromethoxy, $C_1$–$C_6$ haloalkyl, such as trifluoromethyl, $C_1$–$C_6$ alkylamino, such as methylamino and ethylamino, di($C_1$–$C_6$ alkyl)amino, such as diethylamino, $C_1$–$C_6$ alkylthio, such as methylthio, halogen, such as fluorine and chlorine, or cyano, and among them, lower alkyl, such as methyl, lower alkoxy, such as methoxy, lower haloalkyl, such as trifluoromethyl, lower haloalkoxy, such as trifluoromethoxy, and halogen, such as chlorine, can be given as an preferable example.

B represents a nitrogen atom or a carbon atom substituted with either of hydrogen or X.

X represents hydrogen, halogen, such as fluorine, chlorine and bromine, $C_1$–$C_6$ alkyl, such as methyl, ethyl and propyl, $C_3$–$C_7$ cycloalkyl, such as cyclopropyl, cyclopentyl and cyclohexyl, $C_2$–$C_6$ alkenyl, such as vinyl and allyl, $C_3$–$C_6$ alkynyl, ethynyl and propagyl, $C_1$–$C_6$ haloalkyl, such as chloromethyl and trifluoromethyl, benzyl substituted with hydrogen, halogen, $C_1$–$C_6$ alkyl, halo $C_1$–$C_6$ alkyl, nitro, cyano, $C_1$–$C_6$ alkoxy, amino, $C_1$–$C_6$ alkylamino, di($C_1$–$C_6$ alkyl)amino, or $C_1$–$C_6$ acyl; phenyl substituted with hydrogen, $C_1$–$C_6$ alkyl, halo $C_1$–$C_6$ alkyl, nitro, cyano, $C_1$–$C_6$ alkoxy, amino, $C_1$–$C_6$ alkylamino, di($C_1$–$C_6$ alkyl) amino, or $C_1$–$C_6$ acyl; $C_1$–$C_6$ alkoxy $C_1$–$C_6$ alkyl, such as methoxymethyl, ethoxymethyl, methoxyethyl and ethoxyethyl, $C_1$–$C_6$ alkylthio $C_1$–$C_6$ alkyl, such as methylthiomethyl, ethylthiomethyl, ethylthiomethyl and ethylthioethyl, phenoxy $C_1$–$C_6$ alkyl, such as phenoxymethyl, phenylthio $C_1$–$C_6$ alkyl, such as phenylthiomethyl, $C_1$–$C_6$ alkylsulfinyl $C_1$–$C_6$ alkyl, such as methylsulfinylmethyl, $C_1$–$C_6$ alkylsulfonyl $C_1$–$C_6$ alkyl, such as methylsulfonylmethyl, phenylsulfonyl $C_1$–$C_6$ alkyl, such as phenylsulfonylmethyl, halo $C_1$–$C_6$ alkylsulfonyl $C_1$–$C_6$ alkyl, such as trifluoromethylsulfonylmethyl, cyano $C_1$–$C_6$ alkyl, such as cyanomethyl, nitro, amino, $C_1$–$C_6$ alkylamino, such as methylamino, di($C_1$–$C_6$ alkyl)amino, such as dimethylamino and ethylmethylamino, acylamino, such as acetylamino and benzoylamino, $C_1$–$C_6$ alkylsulfonylamino, such as methylsulfonylamino, formyl, $C_1$–$C_6$ acyl, cyano, carboxyl, hydroxyl, $C_1$–$C_6$ alkoxycarbonyl, such as methoxycarbonyl and ethoxycarbonyl, $C_1$–$C_6$ alkylcarbonyl, such as acetyl and propionyl, $C_1$–$C_6$ acyl $C_1$–$C_6$ alkoxymoyl, $C_1$–$C_6$ acylimidoyl, carbamoyl, $C_1$–$C_6$ alkoxy, such as methoxy, ethoxy and isopropoxy, $C_2$–$C_6$ alkenyloxy, such as allyloxy, $C_3$–$C_6$ alkynyloxy, such as propagyloxy, $C_1$–$C_6$ alkoxy $C_1$–$C_6$ alkoxy, such as methoxymethoxy and ethoxyethoxy, halo $C_1$–$C_6$ alkoxy, such as trifluoromethyl, $C_1$–$C_6$ alkylthio $C_1$–$C_6$ alkoxy, such as methylthiomethyl, $C_1$–$C_6$ alkylsulfonyloxy, halo $C_1$–$C_6$ alkylsulfonyloxy, $C_1$–$C_6$ alkoxy substituted with $C_1$–$C_6$ alkoxycarbonyl, $C_1$–$C_6$ alkylsulfonyloxy, $C_1$–$C_6$ alkylthio, such as mercapto, methylthio and ethylthio, $C_1$–$C_6$ alkylsulfonyl, such as methanesulfonyl, $C_2$–$C_6$ alkenylthio, $C_3$–$C_6$ alkynylthio, acyloxy, such as acetoxy, carbamoyloxy, thiocarbamoyloxy, benzyloxy, phenoxy substituted with hydrogen, $C_1$–$C_6$ alkyl, halo $C_1$–$C_6$ alkyl, nitro, cyano, $C_1$–$C_6$ alkoxy, amino, $C_1$–$C_6$ alkylamino, di($C_1$–$C_6$ alkyl)amino or $C_1$–$C_6$ acyl; phenylthio substituted with hydrogen, $C_1$–$C_6$ alkyl, halo $C_1$–$C_6$ alkyl, nitro, cyano, $C_1$–$C_6$ alkoxy, amino, $C_1$–$C_6$ alkylamino, di($C_1$–$C_6$ alkyl)amino or $C_1$–$C_6$ acyl; phenylsulfonyloxy, benzoyloxy, phenylsulfonyl, oxyheterocycle, thioheterocycle, benzoyl or heterocycle group, or, two of X-groups may combine to form a saturated or unsaturated carbon cycle or heterocycle.

Y represents hydrogen, halogen, such as fluorine, chlorine and bromine, $C_1$–$C_6$ alkyl, such as methyl and ethyl, $C_3$–$C_7$ cycloalkyl, such as cyclopropyl, cyclopentyl and cyclohexyl, $C_2$–$C_6$ alkenyl, such as vinyl and allyl, $C_3$–$C_6$ alkynyl, such as ethynyl and propagyl, $C_1$–$C_6$ haloalkyl, such as chloroethyl and trifluoromethyl, benzyl optionally substituted with, $C_1$–$C_6$ alkyl, halo $C_1$–$C_6$ alkyl, nitro, cyano, $C_1$–$C_6$ alkoxy, amino, $C_1$–$C_6$ alkylamino, di($C_1$–$C_6$ alkyl)amino, or $C_1$–$C_6$ acyl; phenyl optionally substituted with $C_1$–$C_6$ alkyl, halo $C_1$–$C_6$ alkyl, nitro, cyano, $C_1$–$C_6$ alkoxy, amino, $C_1$–$C_6$ alkylamino, di($C_1$–$C_6$ alkyl)amino or $C_1$–$C_6$ acyl; $C_1$–$C_6$ alkoxy $C_1$–$C_6$ alkyl, $C_1$–$C_6$ alkylthio $C_1$–$C_6$ alkyl, phenoxy $C_1$–$C_6$ alkyl, phenylthio $C_1$–$C_6$ alkyl, $C_1$–$C_6$ alkylsulfinyl $C_1$–$C_6$ alkyl, $C_1$–$C_6$ alkylsulfonyl $C_1$–$C_6$ alkyl, phenylsulfonyl $C_1$–$C_6$ alkyl, cyano $C_1$–$C_6$ alkyl, nitro, amino, $C_1$–$C_6$ alkylamino, di($C_1$–$C_6$ alkyl) amino, acylamino, $C_1$–$C_6$ alkylsulfonylamino, formyl, $C_1$–$C_6$ acyl, cyano, carboxyl, hydroxyl, $C_1$–$C_6$ alkoxycarbonyl, such as methoxycarbonyl and ethoxycarbonyl, $C_1$–$C_6$ alkylthiocarbonyl, $C_1$–$C_6$ acyl $C_1$–$C_6$ alkoxymoyl, $C_1$–$C_6$ acylimidoyl, carbamoyl, $C_1$–$C_6$ alkoxy, such as methoxy, ethoxy and isopropoxy, $C_2$–$C_6$ alkenyloxy, $C_3$–$C_6$ alkynyloxy, $C_1$–$C_6$ alkoxy $C_1$–$C_6$ alkoxy, $C_1$–$C_6$ alkylthio $C_1$–$C_6$ alkoxy, $C_1$–$C_6$ alkylsulfonyl $C_1$–$C_6$ alkoxy, $C_1$–$C_6$ alkoxy substituted with $C_1$–$C_6$ alkoxycarbonyl, $C_1$–$C_6$ alkylsulfonyloxy, $C_1$–$C_6$ alkylthio, such as mercapto and methylthio, $C_1$–$C_6$ alkylsulfonyl, such as methanesulfonyl, $C_2$–$C_6$ alkenylthio, $C_3$–$C_6$ alkynylthio, acyloxy, carbamoyloxy, thiocarbamoyloxy, benzyloxy, phenyl substituted with hydrogen, $C_1$–$C_6$ alkyl, halo $C_1$–$C_6$ alkyl, nitro, cyano, $C_1$–$C_6$ alkoxy, amino, $C_1$–$C_6$ alkylamino, di($C_1$–$C_6$ alkyl)amino or $C_1$–$C_6$ acyl; phenoxy substituted with hydrogen, $C_1$–$C_6$ alkyl, halo $C_1$–$C_6$ alkyl, nitro, cyano, $C_1$–$C_6$ alkoxy, amino, $C_1$–$C_6$ alkylamino, di($C_1$–$C_6$ alkyl)amino, or $C_1$–$C_6$ acyl; phenylthio, phenylsulfonyloxy, benzoyloxy, phenylsulfonyl, oxyheterocycle, thioheterocycle, benzoyl or heterocycle.

Further, two groups represented by Y bonding to 4- and 5-positions of oxazole cycle, respectively, may combine to form a saturated or unsaturated 5 to 6-membered carbon ring or heterocycle.

And, m represents an integar of 1 or 2, and n represents an integar of 1, 2, 3, or 4.

In the general formula [I] shown above, a saturated or unsaturated oxazole-2-yl group, a saturated or unsaturated oxazole-4-yl group, a saturated or unsaturated oxazole-5-yl group and a tetrahydrobenzoxazole-2-yl group are given as the example for the oxazole ring bonding to a benzene ring, and, in particular, an oxazole-2-yl group or a tetrahydrobenzoxazole-2-yl group optionally-substituted with a lower alkyl, halogen, or phenyl substituted with any of hydrogen, $C_1$–$C_6$ alkyl, halo $C_1$–$C_6$ alkyl, nitro, cyano, $C_1$–$C_6$ alkoxy, amino, $C_1$–$C_6$ alkylamino, di($C_1$–$C_6$ alkyl) amino and $C_1$–$C_6$ acyl, can be given as an preferable example.

As preferable examples for the compounds represented by the general formula [I], compounds represented by the following chemical formulas [I-1] and [I-2] are given.

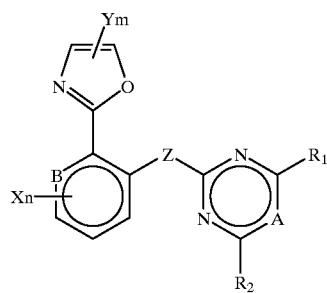

(I-I)

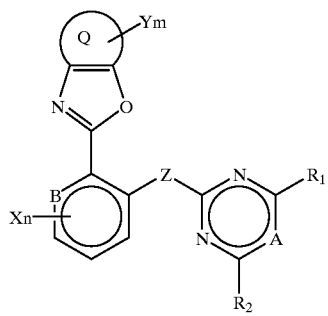

(I-II)

In the general formulas [I-1] and [I-II], A, $R_3$, B, Z, $R_1$, $R_2$, $R_3$, X, m and n are described above, Q represents a 5 to 8-membered ring which may contain one or two oxygen atoms, sulfur atoms, nitrogen atoms, silicon atoms or phosphorus atoms, Y represents hydrogen, $C_1$–$C_6$ alkyl, $C_3$–$C_7$ cycloalkyl, $C_2$–$C_6$ alkenyl, $C_3$–$C_6$ alkynyl, $C_1$–$C_6$ halo alkyl, optionally substituted-benzyl, optionally substituted-phenyl, $C_1$–$C_6$ alkoxy $C_1$–$C_6$ alkyl, $C_1$–$C_6$ alkylthio $C_1$–$C_6$ alkyl, optionally substituted-phenoxy $C_1$–$C_6$ alkyl, phenylthio $C_1$–$C_6$ alkyl, $C_1$–$C_6$ alkylsulfinyl $C_1$–$C_6$ alkyl, $C_1$–$C_6$ alkylsulfonyl $C_1$–$C_6$ alkyl, phenylsulfonyl $C_1$–$C_6$ alkyl, cyano $C_1$–$C_6$ alkyl, halogen, nitro, amino, $C_1$–$C_6$ alkylamino, di($C_1$–$C_6$ alkyl)amino, acylamino, $C_1$–$C_6$ alkylsulfonylamino, formyl, $C_1$–$C_6$ acyl, cyano, carboxyl, hydroxyl, optionally substituted $C_1$–$C_6$ alkoxycarbonyl, optionally substituted $C_1$–$C_6$ alkylthiocarbonyl, $C_1$–$C_6$ acyl $C_1$–$C_6$ alkoxymoyl, $C_1$–$C_6$ acylimidoyl, carbamoyl, $C_1$–$C_6$ alkoxy, $C_2$–$C_6$ alkenyloxy, $C_3$–$C_6$ alkynyloxy, $C_1$–$C_6$ alkoxy $C_1$–$C_6$ alkoxy, $C_1$–$C_6$ alkylthio $C_1$–$C_6$ alkoxy, $C_1$–$C_6$ alkylsulfonyl $C_1$–$C_6$ alkoxy, $C_1$–$C_6$ alkoxy substituted with $C_1$–$C_6$ alkoxycarbonyl, $C_1$–$C_6$ alkylsulfonyloxy, thiol, $C_1$–$C_6$ alkylthio, $C_1$–$C_6$ alkylsulfonyl, $C_2$–$C_6$ alkenylthio, $C_3$–$C_6$ alkynylthio, acyloxy, carbamoyloxy, thiocarbamoyloxy, optionally substituted benzyloxy, optionally substituted phenoxy, optionally substituted phenylthio, optionally substituted phenylsulfonyloxy, optionally substituted benzoyloxy, optionally substituted phenylsulfonyl, optionally substituted oxyheterocycle, optionally substituted thioheterocycle, optionally substituted benzoyl, optionally substituted heterocycle, oxo, ketal, hydroxymoyl, oxyheterocycle $C_1$–$C_6$ alkyl, thioheterocycle $C_1$–$C_6$ alkyl, halo $C_1$–$C_6$ alkylsulfonyloxy, carbohydrazonoyl or imino.

And, ketone and hetero atoms, which constitute Q structure, may adjoin to form either lactone or lactam, or, two groups represented by X or Y may be linked to form a saturated or unsaturated carbon ring or heterocycle.

The compounds specified in the present invention and the salts thereof show to have a high herbicidal activity in both manners of soil application and foliar application when these are used in the fields of upland crops.

Preparation of Compounds

The compounds specified in the present invention can be prepared according to the following method.

(Method for Preparation—1)

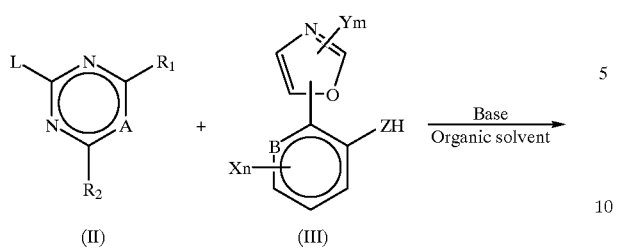
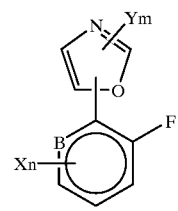

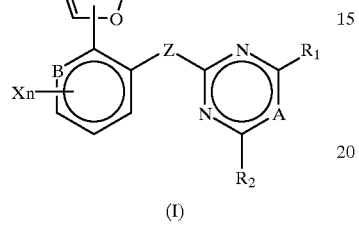

A compound represented by a general formula [II] shown above, wherein $R_1$, $R_2$ and A are as described above and L represents halogen, $C_1$–$C_6$ alkylsulfonyl or optionally substituted benzenesulfonyl, is subjected to a coupling reaction with a compound represented by a general formula [III], wherein B, X, Y, Z, m and n are as described above, in an organic solvent in the presence of a base.

As the base to be used for the reaction described above, an alkali metal hydride, a carbonate of an alkali metal, an organic base, such as triethylamine and the like can be used, for example. And, as the solvent to be used in the reaction, N,N-dimethylformamide (DMF), N,N-dimethylsulfoxide (DMSO), tetrahydrofuran (THF), 1,2-dimethoxyethane (DME) and the like can be used, for example.

The reaction proceeds smoothly at a temperature range of from 0 to 60° C., or around 90° C. in particular cases.

(Method for Preparation—2)

Compounds represented by a general formula [III] shown above, wherein B, X, Y, Z, m, and n are as described above, can be prepared from a compound represented by a general formula [III'];

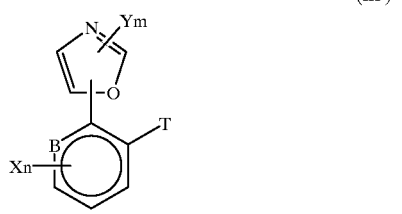

wherein B, X, Y, m and n are as described above and T represents halogen, nitro, $C_1$–$C_6$ alkoxy or benzyloxy, according to a known method disclosed in the references, such method as substitution reaction, deblocking, etc.

A derivation from a fluoro compound represented by a general formula [III'a];

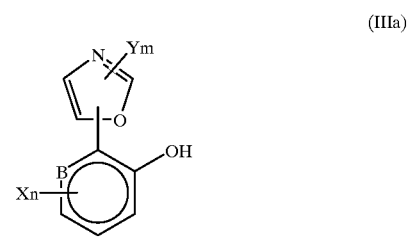

wherein B, X, Y, m and n are as described above, to a phenol compound represented by a general formula [IIIa];

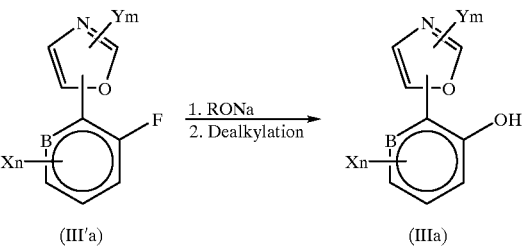

wherein B, X, Y, m and n are as described above, is described hereinbelow as an example.

In this reaction, a compound represented by a general formula [III'a], wherein B, X, Y, m and n are as described above, is subjected to a reaction with alkoxide in an appropriate solvent for a period of from 1 to 24 hours at a temperature of from room temperature to a temperature lower than a boiling point of the solvent used to thereby obtain an alkoxy compound as an intermediate.

As the solvent to be used in the reaction, DMF, DMSO, THF, DME or the like can be used. By the completion of the reaction, the mixture is stirred at a temperature of from 0 to 60° C., or 90° C. when appropriate.

Also, an alkoxy compound as an intermediate can be derived to a compound represented by a general formula [III'a], wherein B, X, Y, m and n are as described above, according to a method described in a published reference, such as T. W. Greene et al, "Protective Groups in Organic Synthesis", John Wiley & Sons Inc., 1991.

(Method for Preparation—3)

Compounds represented by a general formula [III'], wherein B, T, X, Y, m and n are as described above, can be prepared according to a method for synthesizing oxazoles, which is described in the reference, for example, I. J. Turchi, "The Chemistry of Heterocyclic Compounds", Vol. 45, John Wiley & Sons Inc., 1986.

In case of 5-phenyl oxazole represented by a general formula [III"];

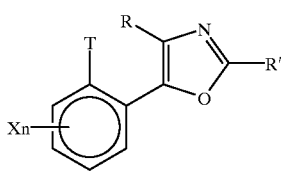

(III″)

wherein X, T and n are as described above, and R and R' represent each independently hydrogen, $C_1$–$C_6$ alkyl, $C_3$–$C_7$ cycloalkyl, $C_2$–$C_6$ alkenyl, $C_3$–$C_6$ alkynyl, $C_1$–$C_6$ haloalkyl, optionally substituted benzyl, optionally substituted phenyl, $C_1$–$C_6$ alkoxy $C_1$–$C_6$ alkyl, $C_1$–$C_6$ alkylthio $C_1$–$C_6$ alkyl, optionally substituted phenoxy $C_1$–$C_6$ alkyl, phenylthio $C_1$–$C_6$ alkyl, $C_1$–$C_6$ alkylsulfinyl $C_1$–$C_6$ alkyl, $C_1$–$C_6$ alkylsulfonyl $C_1$–$C_6$ alkyl, phenylsulfonyl $C_1$–$C_6$ alkyl, cyano $C_1$–$C_6$ alkyl, formyl, cyano, optionally substituted $C_1$–$C_6$ alkoxycarbonyl, optionally substituted $C_1$–$C_6$ alkylthiocarbonyl, $C_1$–$C_6$ acylalkoxymoyl, $C_1$–$C_6$ acylimidoyl, carbamoyl, $C_1$–$C_6$ alkoxy, $C_2$–$C_6$ alkenyloxy, $C_3$–$C_6$ alkynyloxy, $C_1$–$C_6$ alkoxy $C_1$–$C_6$ alkoxy, halo $C_1$–$C_6$ alkoxy, $C_1$–$C_6$ alkylthio $C_1$–$C_6$ alkoxy, $C_1$–$C_6$ alkoxy substituted with $C_1$–$C_6$ alkoxycarbonyl, $C_1$–$C_6$ alkylthio, $C_1$–$C_6$ alkylsulfonyl, $C_2$–$C_6$ alkenylthio, $C_3$–$C_6$ alkynylthio, optionally substituted benzyloxy, optionally substituted phenoxy, optionally substituted phenylthio, optionally substituted phenylsulfonyl, optionally substituted oxyheterocycle, optionally substituted thioheterocycle, optionally substituted benzoyl or optionally substituted heterocycle, the following methods from A through G can be employed as methods for preparing the said compound.

(Method A)

5-phenyl oxazole represented by the general formula [III″] can be prepared by subjecting a compound represented by a general formula [IV], wherein R, R', T, X and n are as described above, to a reaction with a dehydrating and condensing agent either in an appropriate solvent or no solvent system at a temperature range of from room temperature to a temperature lower than a boiling point of the solvent used for a period of from 1 to 24 hours. Alternatively, the said reaction can be proceeded in the presence of an appropriate base.

As examples of the dehydrating and condensing agent to be used in the reaction described above, phosphorus pentachloride, phosphorus oxychloride, polyphosphoric acid, phosphorus pentaoxide, triphenylphosphine-carbon tetrachloride, etc. can be given.

As examples of the solvent to be used in the reaction described above, aromatic hydrocarbons, such as benzene and toluene, and halogenated hydrocarbons, such as dichloro methane and chloroform, can be given.

Also, as examples of the base to be used in the reaction described above, organic bases, such as triethylamine and DBU, can be given.

As a preferable example for a combination of a dehydrating and condensing agent, a base and a solvent, phosphorus oxychloride, an organic base, such as triethylamine, and an halogenated hydrocarbon, such as chloroform, can be given.

(Method B)

5-phenyl oxazole represented by the general formula [III″] can be prepared by subjecting a compound represented by a general formula [V], wherein R' is as described above, to a reaction with α-azide ketone represented by a general formula [VI], wherein X, T, X and n are as described above, in an appropriate solvent in the presence of triphenylsulfone

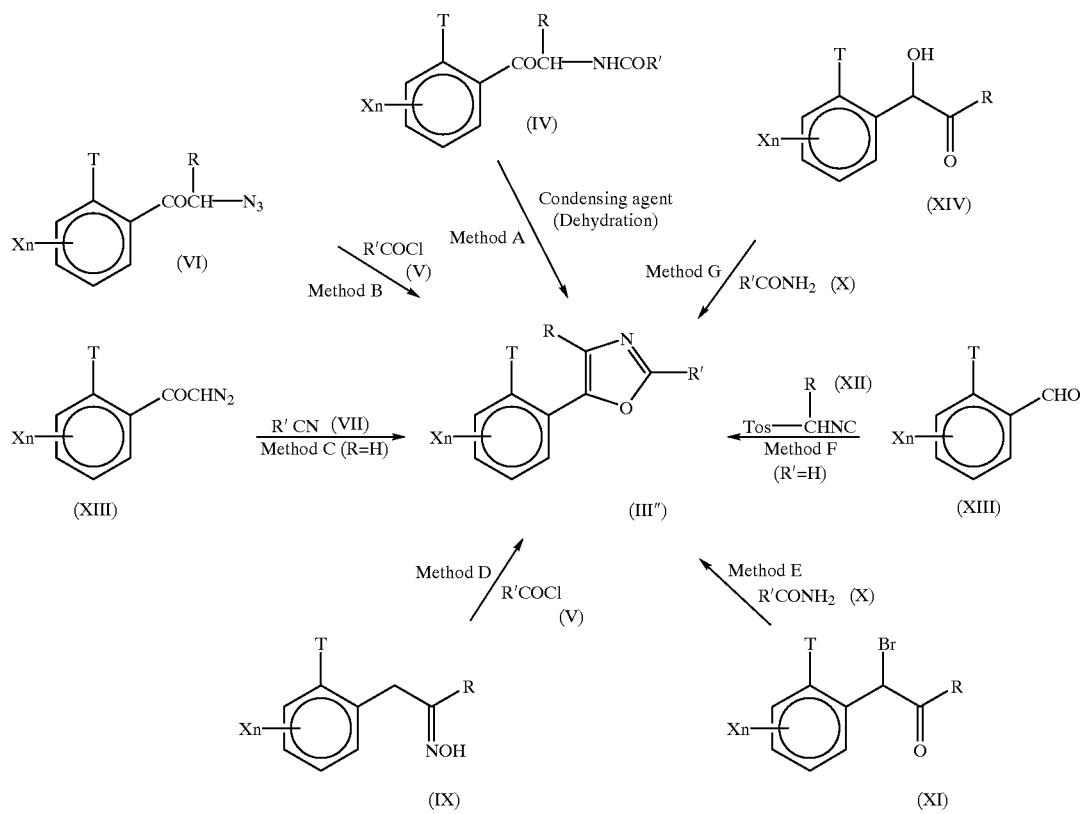

or the like at a temperature ranging from room temperature to a temperature lower than a boiling point of the solvent used for a period of from 1 to 24 hours, according to a publicly-known method disclosed in the references.

As preferable examples for the solvent to be used in this reaction, aromatic hydrocarbon, such as benzene and toluene, can be given.

(Method C)

5-phenyl oxazole represented by the general formula [III"] can be prepared by subjecting a compound represented by a general formula [VII], wherein R' is as described above, to a reaction with a diazo ketone derivative represented by a general formula [VIII], wherein T, X and n are as described above, in an appropriate solvent in the presence of a Louis acid, such as $BF_3$, $Et_2O$ and chloride tungstate, and a base at a temperature ranging from room temperature to a temperature lower than a boiling point of the solvent used for a period of from 1 to 24 hours, according to a publicly-known method disclosed in the references.

As examples for the solvent to be used in this reaction, aromatic hydrocarbon, such as benzene and toluene, and halogenated hydrocarbons, such as dichiromethane and chloroform, can be given. Also, by means of using excess dose of the compound [VII], the objective compound can be prepared in no solvent system as well. As examples for the base to be used in this reaction, organic bases, such as triethylamine and DBU, and the like can be given.

(Method D)

5-phenyl oxazole represented by the general formula [III"] can be prepared by subjecting a compound represented by a general formula [V], wherein R' is as described above, to a reaction with an oxime derivative represented by a general formula [IX], wherein R, T, X and n are as described above, in an appropriate solvent in the presence of an acid at a temperature ranging from room temperature to a temperature lower than the boiling point of the solvent used for a period of from 1 to 24 hours, according to a publicly-known method disclosed in the references.

As examples for the solvent to be used in this reaction, aromatic hydrocarbons, such as benzene and toluene, halogenated hydrocarbons, such as dichloromethane and chloroform, organic acids, such as acetic acid, acid anhydrides, such as acetic anhydride, and the like can be given. Also, by means of using excess dose of the compound [V], the objective compound can be prepared without solvent as well.

Further, as examples for the acid to be used in this reaction, inorganic acids, such as hydrochloric acid and sulfuric acid, and organic acids, such as para-toluene sulfonic acid, can be given.

(Method E)

5-phenyl oxazole represented by the general formula [III"] can be prepared by subjecting a compound represented by a general formula [X], wherein R' is as described above, to a reaction with an α-halo ketone derivative represented by a general formula [XI], wherein R, T, X and n are as described above, either in an appropriate solvent or no solvent system and either in the presence of a base or without bases at a temperature ranging from room temperature to a boiling point of the solvent used for a period of from 1 to 24 hours, according to a publicly-known method disclosed in the references.

As examples for the solvent to be used in this reaction, aromatic hydrocarbon, such as benzene and toluene, halogenated hydrocarbons, such as dichloromethane and chloroform, and the like can be given.

Further, as examples for the base to he used in this reaction, hydrogenated alkali metals, alkali metal carbonates and organic bases, such as triethylamine, can be given.

(Method F)

5-phenyl oxazole represented by the general formula [III"] can be prepared by subjecting a compound represented by a general formula [XIII], wherein T, X and n are as described above, to a reaction with an isonitrile derivative represented by a general formula [XII], wherein R is as described above, in an appropriate solvent in the presence of an appropriate base or without bases at a temperature ranging from room temperature to a temperature lower than a boiling point of the solvent used for a period of from 1 to 24 hours, according to a publicly-known method disclosed in the references.

As examples for the solvent to be used in this reaction, alcohols, such as methanol and ethanol, aromatic hydrocarbons, such as benzene and toluene, ethers, such as THF and DME, DMF, DMSO and the like can be given.

Further, as examples for the base to be used in this reaction, hydrogenated alkali metals, alkali metal carbonates and organic bases, such as triethylamine, can be given.

(Method G)

5-phenyl oxazole represented by the general formula [III"] can be prepared by subjecting a compound represented by a general formula [X], wherein R' is as described above, to a reaction with an α-hydroxy ketone derivative represented by a general formula [XIV], wherein R, T, X and n are as described above, in an appropriate solvent in the presence of an acid at a temperature ranging from room temperature to a temperature lower than a boiling point of the solvent used for a period of from 1 to 24 hours, according to a publicly-known method disclosed in the references.

As examples for the solvent to be used in this reaction, aromatic hydrocarbons, such as benzene and toluene, halogenated hydrocarbons, such as dichloromethane and chloroform, organic acids, such as acetic acid, acid anhydrides, such as acetic anhydride, and the like can be given. Also, by means of using excess dose of the compound [V], the objective compound can be prepared without solvent as well.

Further, as examples for the acid to be used in this reaction, inorganic acids, such as hydrochloric acid and sulfuric acid, can be given.

(Method for Preparation—4)

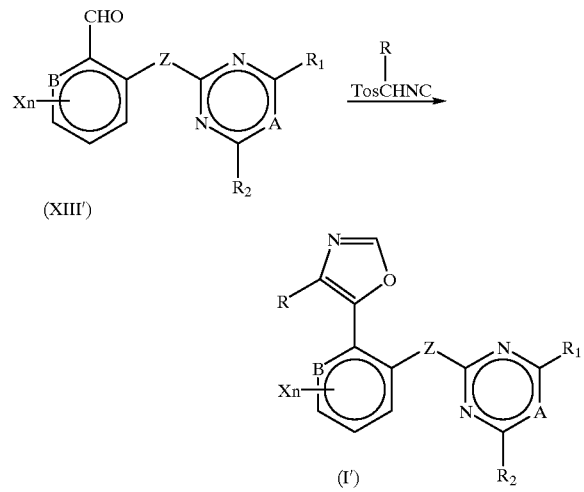

Compounds represented by the general formula [III] can be prepared by proceeding a reaction of a compound represented by a general formula [XIII'], wherein $R_1$, $R_2$, A, B, Z, X and n are as described above, and an isocyanide compound represented by a general formula [XII], wherein R is as described above, in an appropriate solvent in the presence of an appropriate base at a temperature ranging from room temperature to a boiling point of the solvent used for a period of from 1 to 24 hours, according to a publicly-known method disclosed in the references.

As the solvent to be used in this reaction, alcohols, such as methanol, ethanol and isopropanol, aromatic hydrocarbons, such as benzene and toluene, halogenated hydrocarbons, such as dichloromethane and chloroform, ethers, such as diethyl ether and THF, ketones, such as acetone, and methyl ethyl ketone (MEK), esters, such as methyl acetate and ethyl acetate, aprotic polar solvent, such as DMF and DMSO, acetonitrile and water can be given, for examples.

As the base to be used in this reaction, carbonates, such as sodium carbonate and potassium carbonate, metal hydroxides, such as potassium hydroxide, metal alcoholates, sodium methylate and sodium ethylate, metal hydrides, such as sodium hydride and potassium hydride, lithium amides, such as lithium diisopropylamide and lithium bis-trimethylsilylamide, and organic bases, such as triethylamine, DBU and pyridine, can be given, for examples.

As preferable examples for a combination of a base and a solvent, the following can be given.

1) Cabonates, such as sodium carbonate and potassium carbonate, and alcohols, such as methanol, ethanol and isopropanol.
2) Ethers, such as diethyl ether and THF, or aprotic polar solvent, such as DMF and DMSO, and metal hydrides, such as sodium hydride and potassium hydride, or lithium amides, such as lithium diisopropylamide and lithium bis-trimethylsilylamide.

(Method for Preparation—5)

(Method for Preparation - 5)

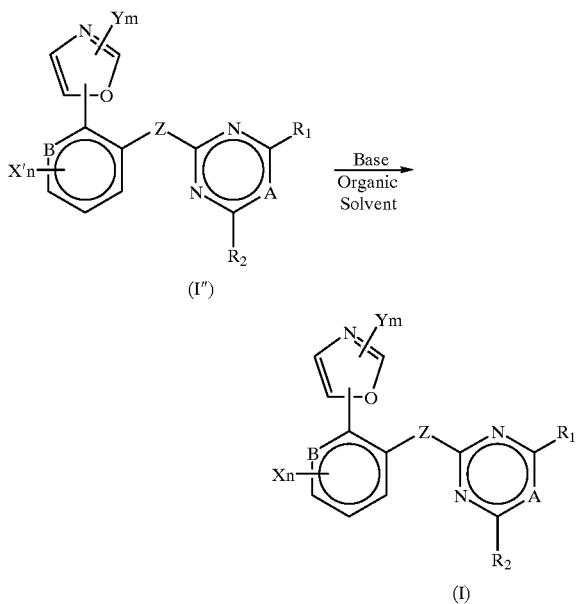

Compounds represented by the general formula [III] can be prepared by proceeding a reaction of a compound represented by the general formula [I"], wherein $R_1$, $R_2$, A, B, Z, m and n are as described above and, X' and Y' are same to X and Y, respectively, and a protective agent, such as acyl halide, isocyanate, isothiocyanate, acid anhydride, alkyl halide and halo formate, to be used for alcohols, thiols, phenols, amides, etc., in an appropriate solvent in the presence of an appropriate base at a temperature ranging from room temperature to the one lower than a boiling point of the solvent used for a period of from 1 to 24 hours, according to a publicly-known method disclosed in the references, for example, T. W. Greene et al., "Protective Groups in Organic Synthesis", John Wiley & Sons, Inc., 1991.

As the solvent to be used in this reaction, alcohols, such as methanol, ethanol and isopropanol, aromatic hydrocarbons, such as benzene and toluene, halogenated hydrocarbons, such as dichloromethiane and chloroform, ethers, such as diethyl ether and THF, kotones, such as acetone and MEK, esters, such as methyl acetate and ethyl acetate, aprotic polar solvent, such as DMF and DMSO, acetonitrile and water can be given, for examples.

As the base to be used in this reaction, carbonates, such as sodium carbonate and potassium carbonate, metal hydroxides, such as potassium hydroxide, metal alcoholates, sodium methylate and sodium ethylate, metal hydrides, such as sodium hydride and potassium hydride, lithium amides, such as lithium diisopropylanide and lithium bis-trimethylsilylamide, and organic bases, such as triethylamine, DBU and pyridine, can be given, for examples.

As preferable examples for a combination of a base and a solvent, the following can be given.

1) Cabonates, such as sodium carbonate and potassium carbonate, and alcohols, such as methanol, ethanol and isopropanol.
2) Ethers, such as diethyl ether and THF, or aprotic polar solvent, such as DMF and DMSO, and metal hydrides, such as sodium hydride and potassium hydride, or lithium amides, such as lithium diisopropylamide and lithium bistrimethylamide.

Alternatively, the compounds represented by the general formula [III'] can be also prepared by proceeding a cross-coupling reaction of a compound represented by the general formula [I"], wherein $R_1$, $R_2$, A, B, Z, m and n are as described above and X' and Y' represent each independently halogen, triflate, etc., and any of phenyl borates according to a publicly-known method.

As the salts of the compounds represented by the general formula [I], environmentally-acceptable salts, for examples, inorganic acid salts, such as hydrochlorides and hydrobromides, organic acid salts, such as acetate, oxalate and formate, alkali metals, alkaline earth metals, ammonium salts, etc., can be given.

These salts can be prepared according to any of publicly-known methods.

(Method for Preparation—6)

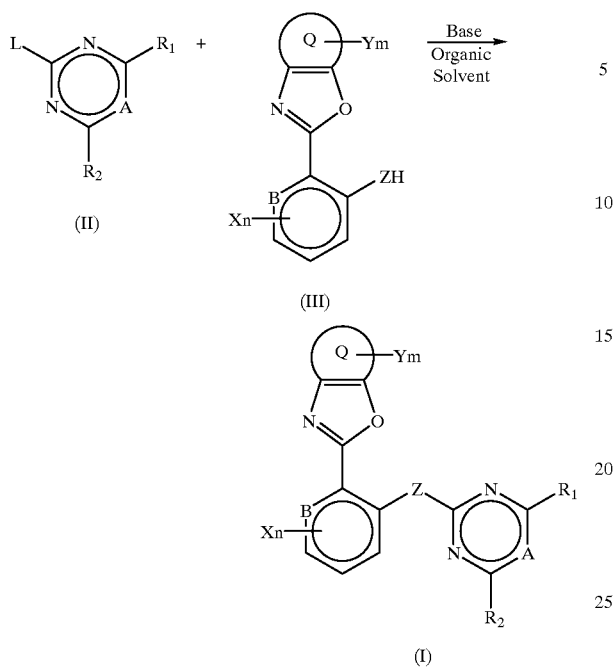

A compound represented by the general formula [II], wherein $R_1$, $R_2$ and A are as described above and L represents halogen, $C_1$–$C_6$ alkylsulfonyl or optionally substituted benzenesulfonyl, is subjected to a coupling reaction with a compound represented by a general formula [III], wherein B, Q, X, Y, Z, m and n are as described above, in an organic solvent in the presence of a base.

As the base described above, carbonates of alkali metal hydrides and alkali metal, and organic bases, such as triethylamine, can be used. Whereas, as the solvent described above, N,N-dimethylformamide (DMF), N,N-dimethylsulfoxide (DMSO), tetrahydrofuran (THF), 1,2-dimethoxy ethane (DME), and the like can be used. The mixture prepared for the reaction described above was subjected to stirring at a temperature of from 0 to 60° C., or at 90° C. when appropriate, till the end of the reaction.

(Method for Preparation—7)

Compounds represented by a general formula [III], wherein B, Q, X, Y, Z, m and n are as described above, can be prepared by using a compound represented by a general formula [III'],

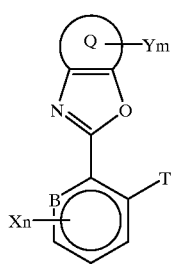

wherein B, Q, X, Y, Z, m and n are as described above and T represents halogen, nitro, $C_1$–$C_6$ alkoxy or benzyloxy, according to a publicly-known method (any of substitution reaction, deblocking, etc.) disclosed in the references.

For example, a process which derives a fluoro compound represented by a general formula [III'a];

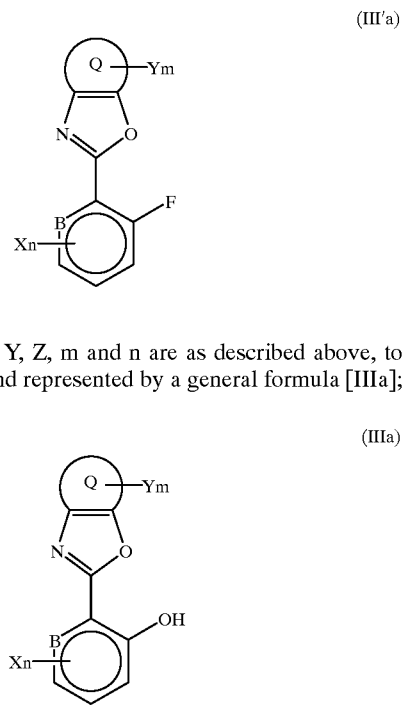

wherein B, Q, X, Y, Z, m and n are as described above, to a phenol compound represented by a general formula [IIIa];

(IIIa)

wherein B, Q, X, Y, Z, m and n are as described above, can be shown hereinbelow.

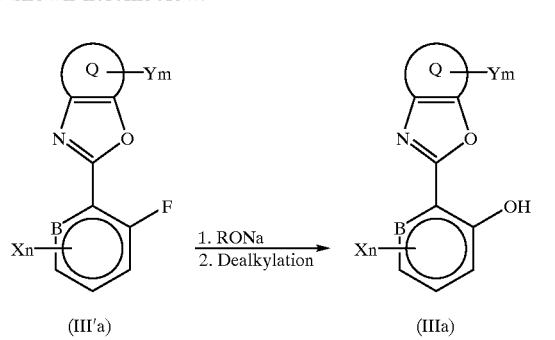

In the above-described derivation reaction, a compound represented by a general formula [III' a], wherein B, Q, X, Y, Z, m and n are as described above, is subjected to a reaction with an alkoxide in an appropriate solvent at a temperature ranging from room temperature to a boiling point of the solvent used for a period of from 1 to 24 hours, to thereby obtain an alkoxy compound as an intermediate.

As the solvent to be used in this reaction, any of DMF, DMSO, THF, DME and the like can be used. The mixture prepared for the reaction described above was subjected to stirring at a temperature of from 0 to 60° C., or at 90° C. when appropriate, till the completion of the reaction.

The alkoxy compound obtained as the intermediate can be derived to a compound represented by the general formula [IIIa], wherein B, Q, X, Y, Z, m and n are as described above, according to a publicly-known method disclosed in the reference, for example, T. W. Greene et al., "Protective Groups in Organic Synthesis", John Wiley & Sons, Inc., 1991.

(Method for Preparation—8)

Compounds represented by a general formula [III'], wherein B, Q, X, Y, m and n are as described above, can be prepared according to a method similar to a method for synthesizing oxazole compounds which is disclosed in the reference, I. J. Turchi, "The Chemistry of Heterocyclic Compounds", vol. 45, John Wiley & Sons, Inc., 1986.

above, to a reaction with α-azide ketone represented by the general formula [VI], wherein Q, Y and m are as described above, in an appropriate solvent in the presence of triphenylphosphine or the like at a temperature ranging from room temperature to a boiling point of the solvent used for a period of from 1 to 24 hours, according to a publicly-known method disclosed in the references.

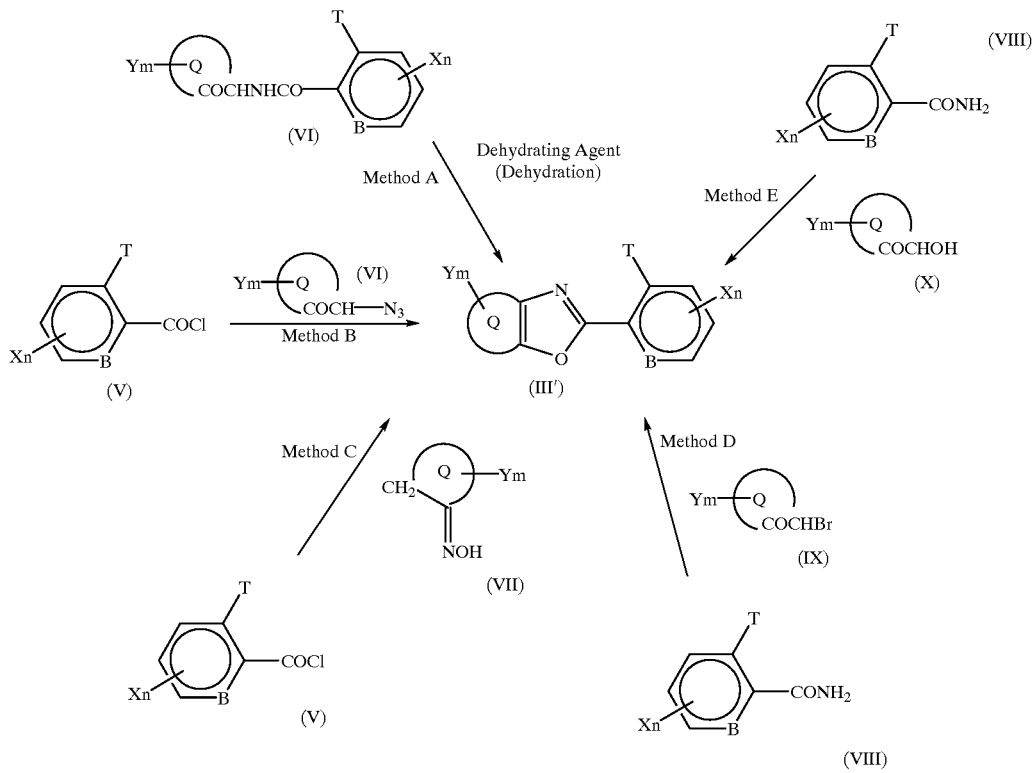

(Method A)

The compounds represented by the general formula [III'], can be prepared by subjecting a compound represented by a general formula [IV], wherein B, Q, X, Y, m and n are as described above, to a reaction with a dehydrating and condensing agent either in an appropriate solvent or no solvent system at a temperature ranging from room temperature to a boiling point of the solvent used for a period of from 1 to 24 hours. The reaction can be also proceeded in the presence of an appropriate base.

As examples for the dehydrating and condensing agent to be used in the reaction described above, phosphorus pentachloride, phosphorus oxychloride, polyphosphoric acid, phosphorus pentaoxide, triphlenylphosphine-carbon tetrachloride, etc. can be given.

As examples for the solvent to be used in the reaction described above, aromatic hydrocarbons, such as benzene and toluene, and halogenated hydrocarbons, such as dichloro methane and chloroform, can be given.

Also, as examples for the base to be used in the reaction described above, organic bases, such as triethylamine and DBU, can be given.

(Method B)

The compounds represented by the general formula [III'] can be prepared by subjecting a compound represented by a general formula [V], wherein B, T, X and n are as described As examples for the solvents to be used in this reaction, aromatic hydrocarbon, such as benzene and toluene, can be given.

(Method C)

The compounds represented by the general formula [III'] can be prepared by subjecting a compound represented by a general formula [V], wherein B, T, X and n are as described above, to a reaction with an oxime derivative represented by a general formula [VII], wherein Q, Y and m are as described above, in an appropriate solvent in the presence of an acid at a temperature ranging from room temperature to a boiling point of the solvent used for a Period of from 1 to 24 hours, according to a publicly-known method disclosed in the references.

As examples for the solvent to be used in this reaction, aromatic hydrocarbons, such as benzene and toluene, halogenated hydrocarbons, such as dichloromethane and chloroform, organic acids, such as acetic acid, and acid anhydrides, such as acetic anhydride, can be given. Also, by means of using excess dose of the compound [V], the objective compound can be prepared in no solvent system as well.

Further, as examples for the acid to be used in this reaction, inorganic acid, such as hydrochloric acid and sulfuric acid, and organic acids, such as paratoluene sulfonic acid, can be given.

(Method D)

The compounds represented by the general formula [III'] can be prepared by subjecting a compound represented by a general formula [VIII], wherein B, T, X, and n are as described above, to a reaction with an α-haloketone derivative represented by a general formula [IX], wherein Q, Y and m are as described above, either in an appropriate solvent or no solvent system, and in the presence of an appropriate base or without base, at a temperature ranging from room temperature to a boiling point of the solvent used for a period of from 1 to 24 hours, according to a publicly-known method disclosed in the references.

As examples for the solvent to be used in this reaction, aromatic hydrocarbons, such as benzene and toluene, and halogenated hydrocarbons, such as dichloromethane and chloroform, can be given.

Further, as examples for the base to be used in this reaction, carbonates of alkali metal hydrides and alkali metals, and organic bases, such as triethylamine, DBU and pyridine, can be given.

(Method E)

The compounds represented by the general formula [III'] can be prepared by subjecting a compound represented by a general formula [XIII], wherein B, T, X and n are as described above, to a reaction with an α-hydroxy ketone derivative represented by a general formula [X], wherein Q, Y and m are as described above, in an appropriate solvent in the presence of an acid at a temperature ranging from room temperature to a boiling point of the solvent used for a period of from 1 to 24 hours, according to a publicly-known method disclosed in the references.

As examples for the solvent to be used in this reaction, aromatic hydrocarbons, such as benzene and toluene, halogenated hydrocarbons, such as dichloromethane and chloroform, organic acids, such as acetic acid, acid anhydrides, such as acetic anhydride, and the like can be given.

Further, as examples for the acid to be used in this reaction, inorganic acids, such as hydrochloric acid and sulfuric acid, can be given.

As examples for the salts represented by the general formula [I], environmentally-acceptable salts, for examples, inorganic salts, such as hydrochlorides and hydrobromides, organic salts, such as acetates, oxalates and formates, alkali metals, alkali earth metals, ammonium salts and the like, can be given. These salts can be prepared according to customarily-employed methods.

The chemical structures of the compounds specified in the present invention were determined by using IR, NMR, MS, etc.

BEST MODE FOR CARRYING OUT THE INVENTION

Now, the present invention is further described in detail with referring examples.

EXAMPLE 1

Synthesis of 4-(2-propyl)-5-ethoxy-2-(2-chloro-6-fluorophenyl)oxazole

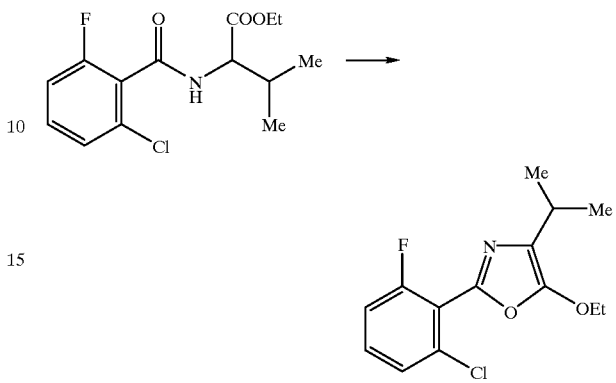

4.7 g of ethyl 2-(2-chloro-6-fluorobenzoylamino)-3-methylbutylate, chloroform solution of 3.6 g phosphorus oxychloride and 302 g triethylamine were mixed and were then subjected to reflux under heating for 15 hours. After completing the reaction, the reaction mixture was poured into ice water and then extracted with chloroform. The organic layer was washed with aqueous sodium hydrogencarbonate, water and saturated saline solution in turn and was dried by anhydrous magnesium sulfate, then the solvent was removed by distillation under reduced pressure, affording the objective oily substance in an amount of 4.3 g.

EXAMPLE 2

Synthesis of 4-(2-propyl)-5-ethoxy-2-(2-benzyloxy-6-chlorophenyl)oxazole

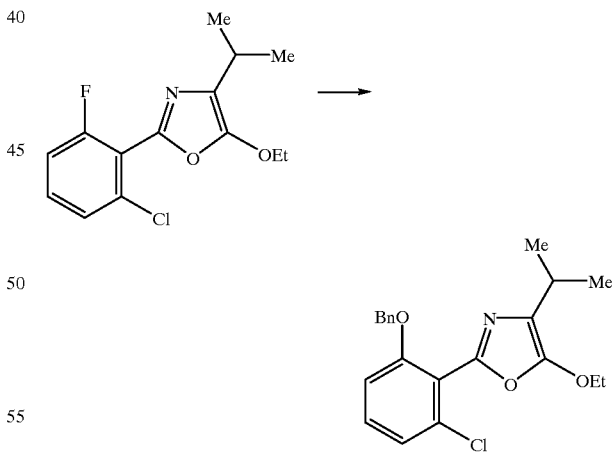

To 20 ml DMF solution containing 0.39 g benzyl alcohol, was added 60% sodium hydride in an amount of 0.16 g. After the end of hydrogen gas generation, DMF solution containing 1.0 g 4-(2-propyl)-5-ethoxy-2-(chloro-6-fluorophenyl)oxazole was added to the solution while keeping at −10° C. The solution reacted was heated up to 70° C. and then stirred for 5 hours. After completing the reaction, the solution reacted was poured into ice water and then extracted with ethyl acetate. The organic layer obtained was washed with water and saturated saline solution in turn, then dried by using anhydrous magnesium sulfate, and the solvent used was removed by distillation under reduced pressure. The residue obtained was purified by using silica gel column chromatography, affording the objective substance in an amount of 0.82 g.

EXAMPLE 3

Synthesis of 4-(2-propyl)-5-ethoxy-2-(2-chloro-6-hydroxyphenyl)oxazole

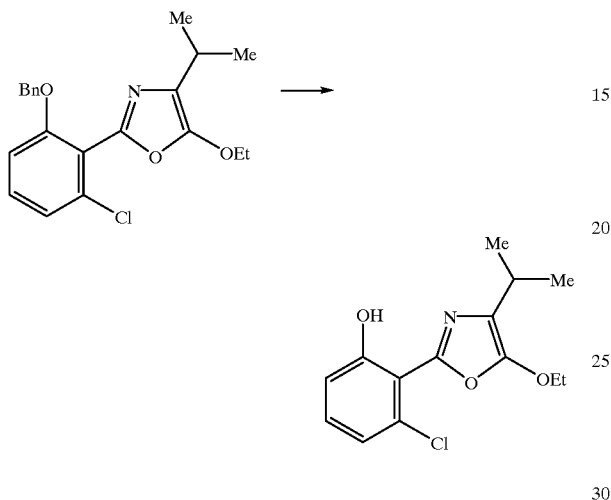

0.4 g 4-(2-propyl)-5-ethoxy-2-(2-benzyloxy-6-chlorophenyl)oxazole was dissolved in 10 ml ethyl acetate. To the solution, 5% palladium/carbon in an amount of 0.11 g was further added, and the solution was stirred under hydrogen atmosphere for 15–30 min. at room temperature. The solution reacted was filtrated, then the filtrate was condensed under reduced pressure, affording the objective substance in an amount of 0.28 g.

EXAMPLE 4

Synthesis of 4-(2-propyl)-5-ethoxy-2-[2-chloro-6-(4,6-dimethoxypyrimidine-2-yloxy)phenyl]oxazole
(Compound No. 1-45)

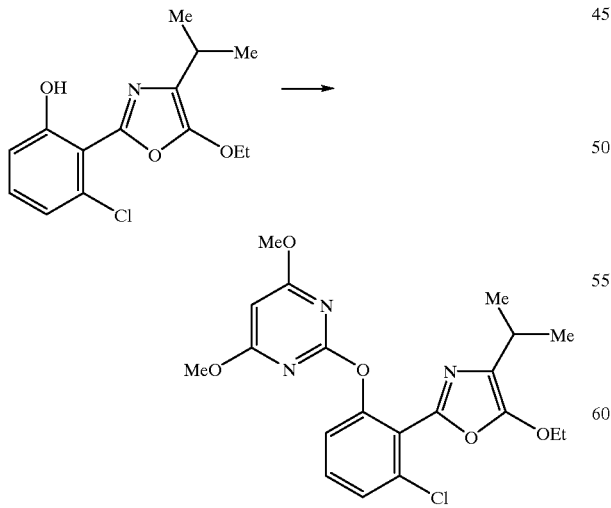

5 ml DMF solution containing 0.27 g 4-(2-propyl)-5-ethoxy-2-(2-chloro-6-hydroxyphenyl)oxazole, 0.20 g 2-methanesulfonyl-4,6-dimethoxypyrimidine and 0.41 g pottasium carbonate was stirred for 3 hours at 60° C. After completing the reaction, the solution reacted was poured into ice water and then extracted with ethyl acetate. The organic layer obtained was washed with water and saturated saline solution in turn and was then dried by using anhydrous magnesium sulfate, and the solvent used was removed by distillation under reduced pressure. The residue obtained was purified by using silica gel column chromatography, affording the objective oily substance in an amount of 0.3 g.

EXAMPLE 5

Synthesis of 5-[2-(4-chlorophenyl)-6-(4,6-dimethoxypyrimidine-2-yloxy)phenyl]oxazole
(Compound No. 3-175)

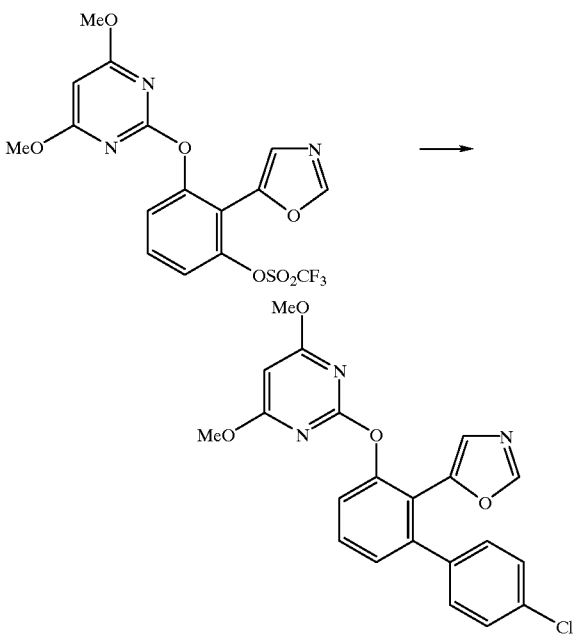

To dimethoxy ethane solution of 0.66 g 5-[2-(4,6-dimethoxypyrimidine-2-yloxy)-6-trifluoromethanesulfonyloxy]phenyl oxazole, were added 0.46 g 4-chlorophenyl boric acid, 0.94 g pottasium phosphate and 128 mg tetrakis(triphenylphosphine)palladium at room temperature. The mixture was then subjected to reflux under heating for 26 hours. After completing the reaction, the solution reacted was poured into water and then extracted with ethyl acetate. The substance obtained was washed with saturated saline solution. The organic layer obtained was dried by using anhydrous magnesium sulfate, and the solvent used was removed by distillation under reduced pressure. The residue obtained was purified by using silica gel column chromatography, affording the objective substance in an amount of 0.39 g.

EXAMPLE 6

Synthesis of 2-methyl-5-[2-fluoro-6-(4,6-dimethoxypyrimidine-2-yloxy)phenyl]oxazole (Compound No. 3-94)

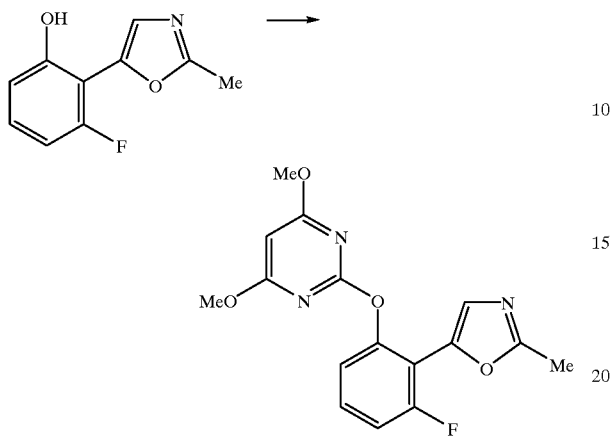

4 ml DMF solution containing 0.12 g 2-(2-methyloxazole-5-yl)-3-fluorophenol, 0.12 g 2-methanesulfonyl-4,6-dimethoxypyrimidine and 0.18 g pottasium carbonate was stirred for 14 hours at 50° C. After completing the reaction, the solution reacted was poured into ice water and then extracted with ethyl acetate. The organic layer obtained was washed with water and then dried by using anhydrous magnesium sulfate. After filtration, the solvent used was removed by distillation under reduced pressure, and the residue obtained was treated with petroleum ether, affording the objective substance in an amount of 0.1 g.

EXAMPLE 7

Synthesis of 2-[2-(4,6-dimethoxypyrimidine-2-yloxy)phenyl]oxazole (Compound No. 3-11)

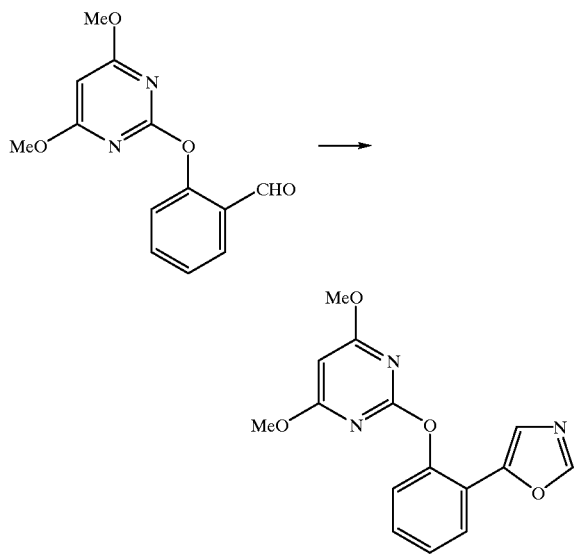

To 10 ml methanol, were added 0.52 g 2-(2-formylphenoxy)-4,6-dimethoxypyrimidine), 0.49 g p-toluenesulfonylmethylisocyanide and 0.69 g pottasium carbonate, and the mixture was subjected to reflux with stirring during 15 min. The solution reacted was added with ice, and solid substance precipitated was filtrated. The solid substance obtained was dissolved in ethyl acetate, and the resulting solution was then dried by using anhydrous magnesium sulfate. Then, the solvent used was removed by distillation under reduced pressure, affording the objective substance in an amount of 0.54 g.

EXAMPLE 8

Synthesis of 5-[2-(4,6-dimethoxypyrimidine-2-yloxy)-6-(4,6-dimethoxytriazine-2-yloxy)phenyl]oxazole (Compound No. 5-14)

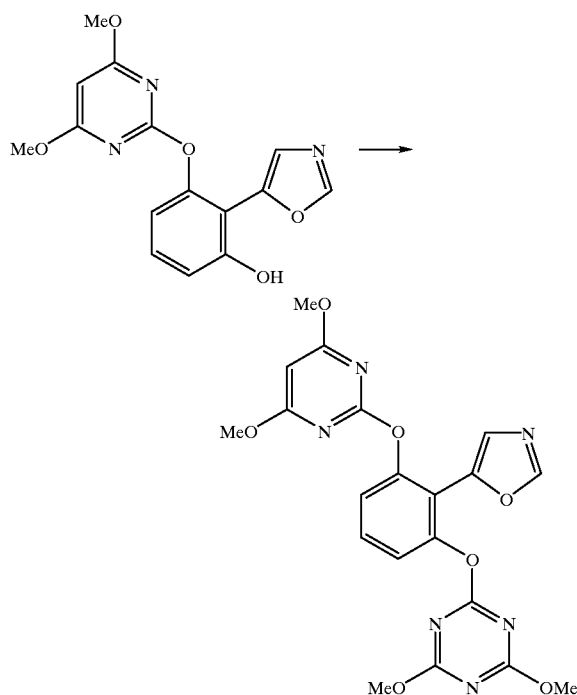

To DMF solution containing 0.14 g pottasium carbonate and 0.15 g 5-[2-(4,6-dimethoxypyrimidine-2-yloxy)-6-hydroxyphenyl]oxazole, was added at once DMF solution containing 0.13 g 2-chloro-4,6-dimethoxytriazine. The solution reacted was stirred for a night at room temperature. After completing the reaction, the solution reacted was poured into ice water and then extracted with ethyl acetate. The organic layer obtained was washed with water and saturated saline solution in turn and was then dried by using anhydrous magnesium sulfate. The solvent used was removed by distillation under reduced pressure, affording the objective substance in an amount of 0.22 g.

EXAMPLE 9

Synthesis of 5-[2-(4,6-dimethoxypyrimidine-2-yloxy)-6-(N-cyclohexylcarbamoyloxy)phenyl]oxazole (Compound No. 3-162)

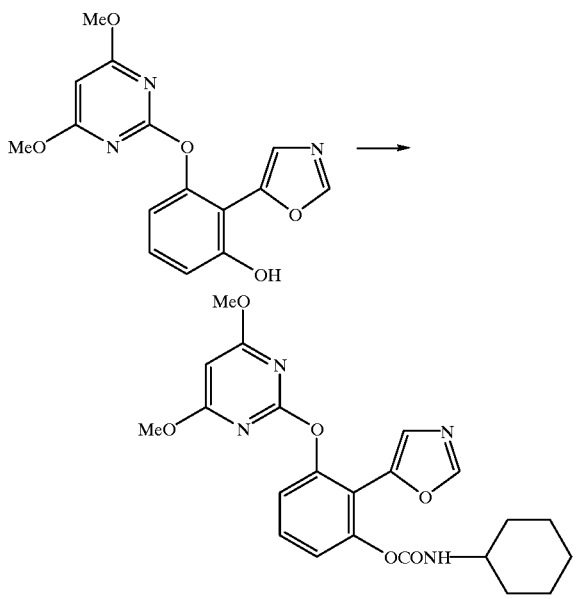

To methylene chloride solution containing 0.15 g 5-[2-(4,6-dimethoxypyrimidine-2-yloxy)-6-hydroxyphenyl]oxazole, was added 0.07 g triethylamine. The solution reacted was stirred at room temperature for 15 min., then 0.08 g cyclohexyl isocyanate was added thereto. The solution was further stirred for 1.5 hours, and the solution reacted was then added with water and extracted with ethyl acetate. The organic layer obtained was washed with water and saturated saline solution in turn and then dried by using anhydrous magnesium sulfate. The solvent used was removed by distillation under reduced pressure, and the oily substance obtained was recrystallized in a mixed-solvent consisting of n-hexane and diethyl ether, affording the objective substance in an amount of 0.17 g.

EXAMPLE 10

Synthesis of 5-[2-(4,6-dimethoxypyrimidine-2-yloxy)-6-phenoxy]phenyloxazole (Compound No. 4-34)

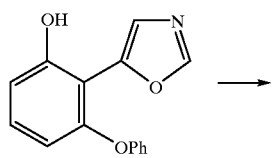

-continued

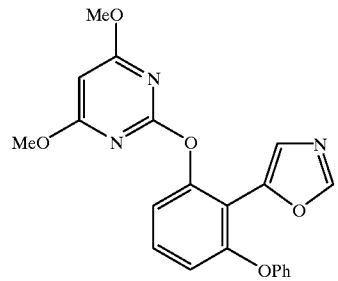

0.43 g 2-(oxazole-5-yl)-3-phenoxyphenol and 0.47 g pottasium carbonate were suspended in DMF, then the suspension was stirred for 30 min. at 30–40° C. The suspension was then added with 0.36 g 4,6-dimethoxy-2-methanesulfonylpyrimidine, then the mixture resulted was stirred for a night at 50° C. After completing the reaction, the solution reacted was poured into ice water and then extracted with ethyl acetate. The organic layer obtained was washed with water and saturated saline solution in turn and was then dried by using anhydrous magnesium sulfate. The solvent used was removed by distillation under reduced pressure, affording the objective substance in an amount of 0.39 g.

EXAMPLE 11

Synthesis of 4-carboxyl-5-(2-(4,6-dimethoxypyrimidine-2-yloxy)phenyl)oxazole (Compound No. 3-15)

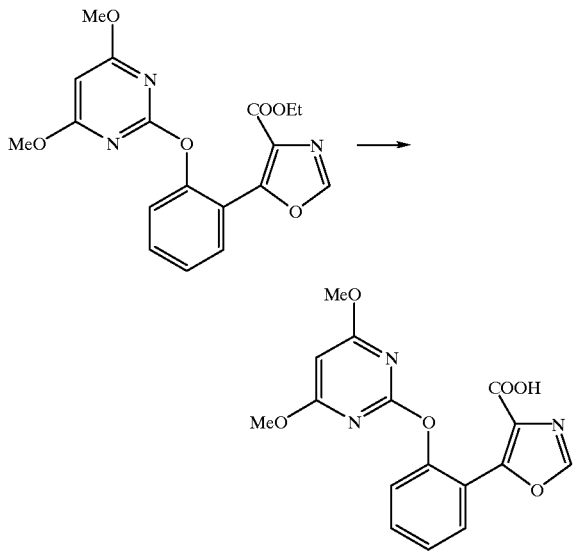

0.69 g 4-ethoxycarbonyl-5-(2-(4,6-dimethoxypyrimidine-2-yloxy)phenyl)oxazole was dissolved in TMF. To the solution, 10% aqueous solution of sodium hydroxide was fed dropwise for 15 min. at 15° C. under stirring, and the resulting solution was stirred for 2 hours at 40° C. After completing the reaction, 3N aqueous solution of hydrogen chloride was added to the reacted-solution to adjust the acidity to an acidic range, and the solution was extracted with ethyl acetate. The organic layer obtained was washed with water and saturated saline solution in turn and was dried by using anhydrous magnesium sulfate, and the solvent used was removed by distillation under reduced pressure. The residue obtained was washed with ether, affording the objective substance in an amount of 0.4 g.

EXAMPLE 12

Synthesis of 4-ethoxycarbonyl-5-(2-(4,6-dimethoxypyrimidine-2-ylthio)phenyl)oxazole (Compound No. 3-12)

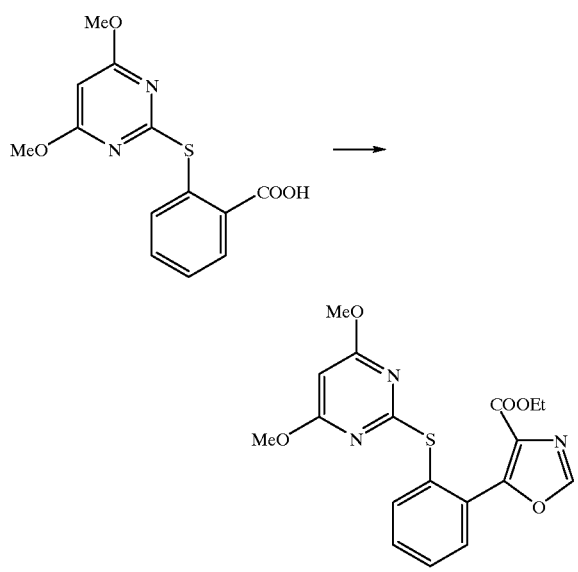

2 g (4,6-dimethoxypyrimidine-2-ylthio)benzoic acid was dissolved in THF, and the solution was added while stirring with 1.22 g N,N'-carbonyldiimidazole at room temperature. The mixture was them stirred for 50 min. at 40–50° C. The solution reacted was fed dropwise while stirring into THF solution of 1.55 g isocyanoethyl acetate at −5° C., immediately after dropping of 2 g DBU at −15° C., and the resulting solution was stirred for two nights at room temperature. After completing the reaction, the solution reacted was poured into ice water, stirred for 30 min. and then extracted with a mixed-solvent consisting of ether and ethyl acetate. The organic layer obtained was washed with water and saturated saline solution in turn and was then dried by using anhydrous magnesium sulfate, and then, the solvent used was removed by distillation under reduced pressure. The residue obtained was purified by using silica gel column chromatography, affording the objective substance in an amount of 1.36 g.

EXAMPLE 13

Synthesis of 5-[2-amino-6-(4,6-dimethoxypyrimidine-2-yloxy)phenyl]oxazole (Compound No. 3-147)

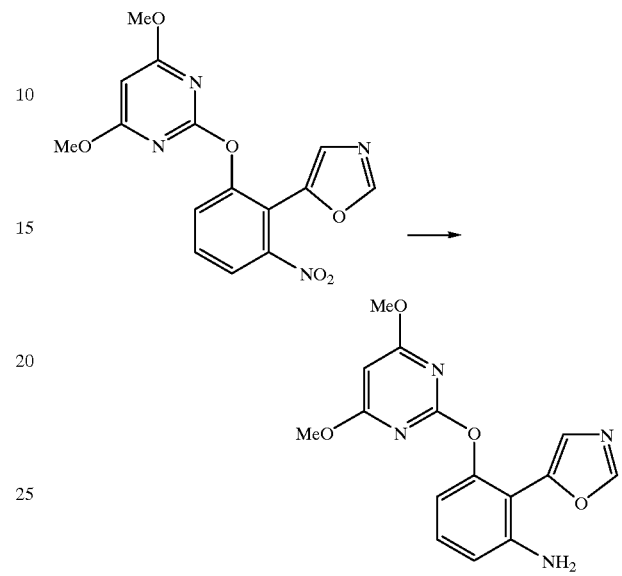

0.24 g silver powder was suspended in 60% aqueous solution of acetic acid in a volume of 3.2 ml, and MEK solution of 0.6 g 5-[2-(4,6-dimethoxypyrimidine-2-yloxy)-6-nitrophenyl]oxazole was fed dropwise thereto at 50° C. while stirring, then the resulting solution was further stirred for 2 hours at 60–70° C. After completing the reaction, the solution reacted was added with ethyl acetate and was filtrated. The filtrate was washed with water and saturated saline solution in turn and was then dried by using anhydrous magnesium sulfate, and the solvent used was removed by distillation under reduced pressure. The residue obtained was purified by using silica gel column chromatography, affording the objective substance in an amount of 0.45 g.

EXAMPLE 14

Synthesis of 4-methyl-5-[2-chloro-6-(4,6-dimethoxypyrimidine-2-yloxy)phenyl]oxazole (Compound No. 3-72)

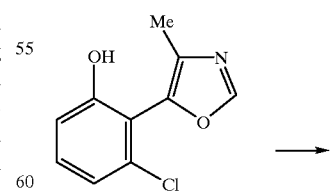

29
-continued

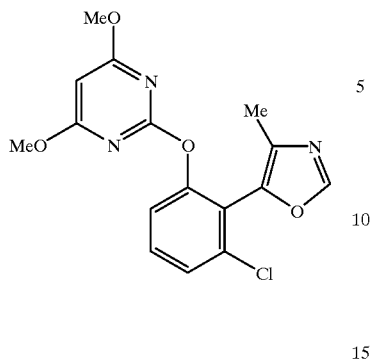

5 ml DMF solution containing 0.25 g 2-(4-methyloxazole-5-yl)-3-chlorophenol, 0.19 g 2-methanesulfonyl-4,6-dimethoxypyrimidine and 0.42 g pottasium carbonate was stirred for 14 hours at 50° C. After completing the reaction, the solution reacted was poured into ice water and then extracted with ethyl acetate. The organic layer obtained was washed with water and then dried by using anhydrous magnesium sulfate. After filtration, the solvent used was removed by distillation under reduced pressure, affording the objective substance in an amount of 0.34 g.

EXAMPLE 15

Synthesis of 2-propyl-4-methyl-5-(2-chloro-6-fluorophenyl)oxazole

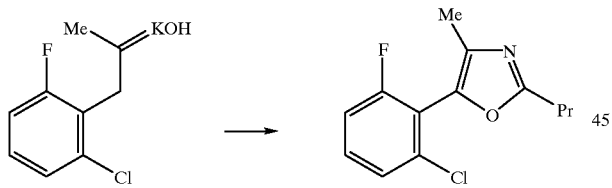

A mixed-solvent consisting of 3.0 g 2-chloro-6-fluorophenylacetoneoxime and 4.7 ml propionic chloride was stirred for 22 hours at 140° C. After completing the reaction, the solution reacted was poured into ice water and was then extracted with ethyl acetate. The organic layer obtained was washed with diluted alkaline water, water and saturated saline solution in turn and was then dried by using anhydrous magnesium sulfate. After filtration, the solvent used was removed by distillation under reduce pressure. The residue obtained was purified by using silica gel column chromatography, where hexane-ethyl acetate solution in a mixing ratio of 8:1 is used, affording the objective substance in an amount of 1.9 g.

30
EXAMPLE 16

Synthesis of 2-propyl-4-methyl-5-(2-chloro-6-(4,6-dimethoxypyrimidine-2-yloxy)phenyl)oxazole
(Compound No. 3-118)

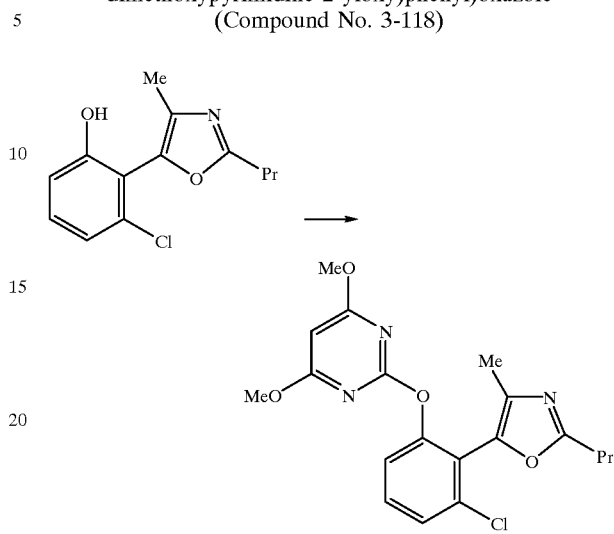

2 ml DMF solution containing 0.24 g 2-propyl-4-methyl-5-(2-chloro-6-hydroxyphenyl)oxazole, 0.2 g 2-methanesulfonyl-4,6-dimethoxypyrimidine and 0.26 g pottasium carbonate was stirred for 14 hours at 60° C. After completing the reaction, the solution reacted was poured into ice water and was then extracted with ethyl acetate. The organic layer obtained was washed with water and was then dried by using anhydrous magnesium sulfate. After filtration, the solvent used was removed by distillation under reduce pressure. The residue obtained was purified by using silica gel column chromatography, where hexane-ethyl acetate solution in a mixing ratio of 4:1 is used, affording the objective substance in an amount of 0.26 g.

EXAMPLE 17

Synthesis of 2-isobutyl-5-(2-chloro-6-fluorophenyl) oxazole

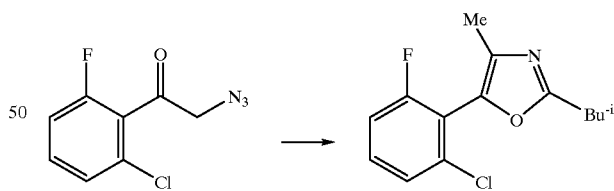

To 100 ml toluene solution of 3.4 g isovaleric chloride and 7.4 g triphenyl phosphine, 40 ml toluene solution of 6.0 g azidemethyl(2-chloro-6-fluorophenyl)ketone was fed dropwise at room temperature. After the dropping, the solution resulted was stirred for 30 min. at the same temperature and was subsequently subjected to reflux under heating for 30 min. After completing the reaction, the solution reacted was poured into ice water and was then extracted with ethyl acetate. The organic layer obtained was washed with diluted alkaline water, water and saturated saline solution in turn and was then dried by using anhydrous magnesium sulfate.

After filtration, the solvent used was removed by distillation under reduce pressure. The residue obtained was purified by using silica gel column chromatography, where hexane-ethyl acetate solution in a mixing ratio of 6:1 is used, affording the objective substance in an amount of 4.8 g.

EXAMPLE 18

Synthesis of 2-isobutyl-5-(2-chloro-6-(4,6-dimethoxypyrimidine-2-yloxy)phenyl)oxazole (Compound No. 3-116)

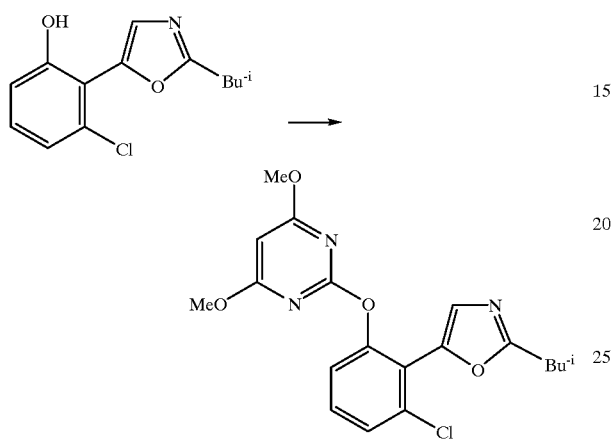

2 ml DMF solution containing 0.5 g 2-isobutyl-5-(2-chloro-6-hydroxyphenyl)oxazole, 0.41 g 2-methanesulfonyl-4,6-dimethoxypyrimidine and 0.55 g pottasium sulfate was stirred for 14 hours at 60° C. After completing the reaction, the solution reacted was poured into ice water and was then extracted with ethyl acetate. The organic layer obtained was washed with water and was then dried by using anhydrous magnesium sulfate. After filtration, the solvent used was removed by distillation under reduce pressure. The residue obtained was purified by using silica gel column chromatography, where hexane-ethyl acetate solution in a mixing ratio of 6:1 is used, affording the objective substance in an amount of 0.64 g.

EXAMPLE 19

Synthesis of 2-phenyl-4-(2,6-difluorophenyl)oxazole

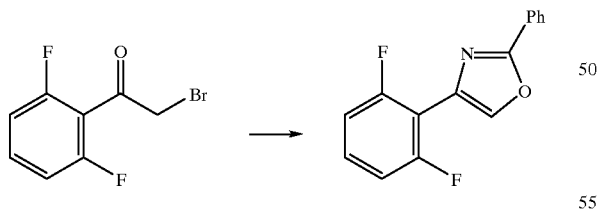

5.7 g 2,6-difluorophenacyl bromide and 3.63 g benzamide were suspended in 20 ml o-xylene, and the suspension was subjected to reflux under heating for 1.5 hours. After completing the reaction, the suspension reacted was added with water, then extracted with ethyl acetate and further washed with saturated saline solution. The organic layer obtained was dried with anhydrous magnesium sulfate, and the solvent used was removed by distillation under reduced pressure. Out of 7.6 g residue obtained, 1.0 g thereof was purified by using silica gel column chromatography, affording the objective substance in an amount of 0.6 g.

EXAMPLE 20

Synthesis of 2-phenyl-4-[2-fluoro-6-dimethoxypyrimidine-2-yloxy)phenyl]oxazole (Compound No. 3-131)

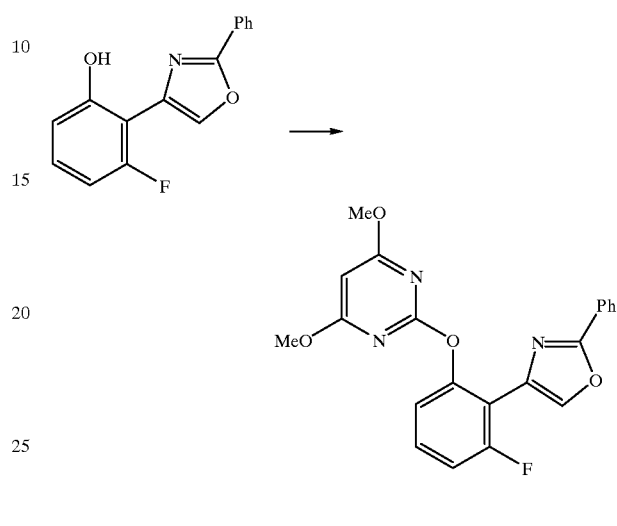

0.2 g 2-phenyl-4-[2-fluoro-6-hydroxyphenyl)oxazole, 0.17 g 2-methanesulfonyl-4,6-dimethoxypyrimidine and 0.22 g pottasium carbonate were suspended in 4 ml DMF, and the suspension was subjected to a reaction for 1.5 hours at 60° C. After completing the reaction, the suspension reacted was added with water and then extracted with ethyl acetate. The organic layer obtained was washed with water and saturated saline solution in turn. After drying the organic layer with anhydrous magnesium sulfate, the solvent used was removed by distillation under reduced pressure. The residue obtained was purified by using silica gel column chromatography, affording the objective substance in an amount of 3.0 g.

EXAMPLE 21

Synthesis of 3-[2-chloro-6-(4,6-dimethoxypyrimidine-2-yloxy)phenyl]-2-oxa-4-azabicyclo[3,3,0]octa-1,3-diene (Compound No. 2-2)

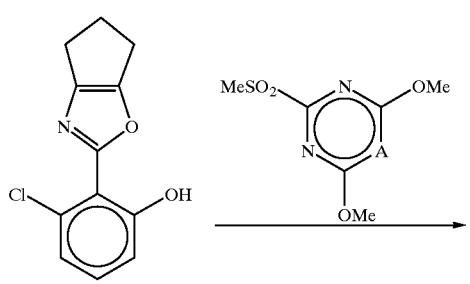

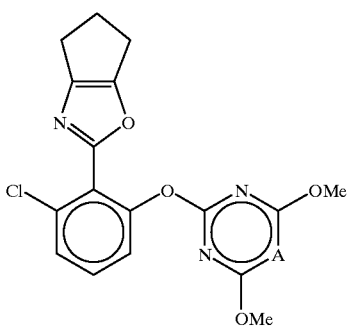

0.3 g 3-(2-chloro-6-hydroxyphenyl)-2-oxa-4-azabicyclo[3,3,0]octa-1,3-diene, 0.28 g 2-methanesulfonyl-4,6-dimethloxypyrimidine and 0.41 g pottasium carbonate were suspended in 5 ml DMF, and the resulting suspension was stirred for 2 hours at 55° C. After completing the reaction, the suspension reacted was added with water and then extracted with ethyl acetate. The extract was then washed with saturated saline solution. The organic layer obtained was dried with anhydrous magnesium sulfate, and the solvent used was then removed by distillation under reduced pressure. The residue obtained was purified by using silica gel column chromatography, affording the objective substance in an amount of 0.44 g.

EXAMPLE 22

Synthesis of 2-[3-(4,6-dimethoxypyrimidine-2-yloxy)-2-pyridyl]-4,5,6,7-tetrahydrobenzoxazole (Compound No. 4-1)

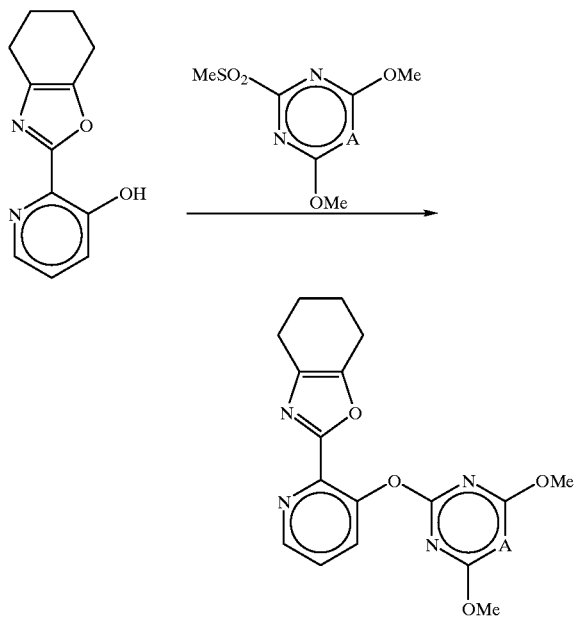

0.12 g 2-(3-hydroxy-2-pyridyl)-4,5,6,7-tetrahydrobenzoxazole, 0.12 g 2-methanesulfonyl-4,6-dimethoxypyrimidine and 0.21 g pottasium carbonate were suspended in 3 ml DMF, and the resulting suspension was subjected to a reaction for 2 hours at 60° C. After completing the reaction, the suspension reacted was added with water and then extracted with ethyl acetate. The extract was then washed with saturated saline solution. The organic layer obtained was dried with anhydrous magnesium sulfate, and the solvent used was removed by distillation under reduced pressure. The residue obtained was purified by using silica gel column chromatography, affording the objective substance in an amount of 0.18 g.

EXAMPLE 23

Synthesis of 2-(3-benzyloxy-2-pyridyl)-4,5,6,7-tetrahydrobenzoxazole

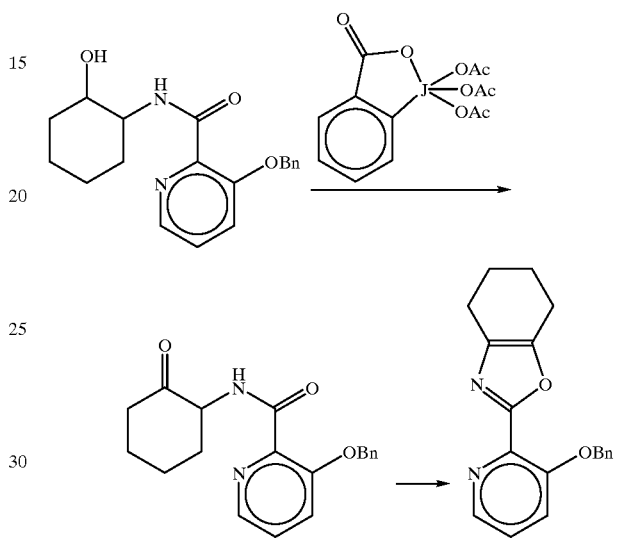

To 20 ml dichloromethane solution of 3.4 g 1,1,1-tris(acetoxy)-1,1-dihydro-1,2-benziodoxole-3(1H)-one, was added 20 ml dichloromethane solution of 1.3 g N-(2-hydroxycyclohexyl)-3-benzyloxypicolinic amide at room temperature. After stirring the solution for 2 hours, the solution reacted was poured into 80 ml diethyl ether, and 2N-aqueous solution of sodium hydroxide and ice were added to the resulting solution. The organic layer obtained was washed with aqueous solution of sodium hydrogencarbonate, water and saturated saline solution in turn and was then dried by using anhydrous magnesium sulfate. The solvent used was removed by distillation under reduced pressure, affording oily substance, N-(2-oxocyclohexyl)-3-benzyloxypicolinic amide in an amount of 1.18 g.

Further, crude amide described above was dissolved in 5 ml chloroform, and 0.2 ml phosphorus oxychloride and 0.4 ml triethylamine were added to the solution in turn. After 3 hours reflux of the solution under heating, the solution reacted was diluted with 80 ml diethyl ether and washed with water, 1N-aqueous solution of sodium hydroxide and saturated saline solution in turn. The organic layer obtained was dried by using anhydrous magnesium sulfate, and the solvent used was then removed by distillation under reduce pressure. The residue obtained was purified by using silica gel column chromatography, affording the objective substance in an amount of 0.3 g.

The representative examples for the compounds specified in the present invention are given in the following Tables 1 through 10, where the compounds described in the examples described above are also included.

TABLE 1

[Structure: oxazole ring with Y19, Y20 substituents connected to benzene ring (positions 1-6) with Xn at position 4, linked via Z to a pyrimidine ring with R1, R2, and A (CR3)]

| No. | Xn *2 | R₁ | R₂ | R₃ | R₁₉ | Y₂₀ | A | Z | Physical Data *3 |
|---|---|---|---|---|---|---|---|---|---|
| 1-1 | H | OMe | OMe | H | H | H | CR₃ | O | |
| 1-2 | 6-Cl | OMe | OMe | H | H | H | CR₃ | O | 87–89 |
| 1-3 | 6-O-Ph | OMe | OMe | H | H | H | CR₃ | O | 112–115 |
| 1-4 | 6-*1 | OMe | OMe | H | H | H | CR₃ | O | 133–134 |
| 1-5 | H | OMe | OMe | H | CH₂OPh-2-Cl-4-Cl | H | CR₃ | O | 92–93.5 |
| 1-6 | 6-F | OMe | OMe | H | H | H | CR₃ | O | |
| 1-7 | 6-Cl | OMe | OMe | H | H | H | CR₃ | O | |
| 1-8 | H | OMe | OMe | H | —(CH)₄— | | CR₃ | O | 88–90 |
| 1-9 | H | OMe | OMe | H | H | H | CR₃ | S | |
| 1-10 | H | OMe | OMe | H | H | Me | CR₃ | O | |
| 1-11 | 6-*1 | OMe | OMe | H | H | Me | CR₃ | O | Gum |
| 1-12 | 6-Cl | OMe | OMe | H | H | CH₂OMe | CR₃ | O | Gum |
| 1-13 | 6-*1 | OMe | OMe | H | H | CH₂OMe | CR₃ | O | Gum |
| 1-14 | 6-*1 | OMe | OMe | H | H | CH₂OPh-2-Cl-4-Cl | CR₃ | O | 159–160 |
| 1-15 | 6-F | OMe | OMe | H | H | CH₂OPh-2-Cl-4-Cl | CR₃ | O | 1.5692 (25.5) |
| 1-16 | 6-Cl | OMe | OMe | H | H | CH₂OPh | CR₃ | O | 1.5678 (25.5) |
| 1-17 | 6-Cl | OMe | OMe | H | H | CH₂OPr-i | CR₃ | O | Gum |
| 1-18 | 6-Cl | OMe | OMe | H | H | CH₂OC₅H₁₁ | CR₃ | O | 1.5402 (26.3) |
| 1-19 | 6-OPr-i | OMe | OMe | H | H | CH₂OPr-i | CR₃ | O | Gum |
| 1-20 | 6-*1 | OMe | OMe | H | H | CH₂OPr-i | CR₃ | O | Gum |
| 1-21 | 6-F | OMe | OMe | H | H | CH₂OPr-i | CR₃ | O | 1.5212 (25.5) |
| 1-22 | H | OMe | OMe | H | H | Ph | CR₃ | O | |
| 1-23 | 6-Cl | OMe | OMe | H | H | Ph | CR₃ | O | 1.6132 (24) |
| 1-24 | 6-Cl | OMe | OMe | H | H | CH₂SMe | CR₃ | O | Gum |
| 1-25 | 6-Cl | OMe | OMe | H | H | CH₂OC₂H₄OMe | CR₃ | O | Gum |
| 1-26 | 6-F | OMe | OMe | H | CF₃ | H | CR₃ | O | |
| 1-27 | H | OMe | OMe | H | Me | H | CR₃ | O | 1.528 (25) |
| 1-28 | 6-F | OMe | OMe | H | Me | H | CR₃ | O | 38–40 |
| 1-29 | 6-O-Ph | OMe | OMe | H | Me | H | CR₃ | O | 79–81 |
| 1-30 | 6-O-Ph | OMe | OMe | H | Me | Br | CR₃ | O | 1.5910 (29) |
| 1-31 | 6-Cl | OMe | OMe | H | Me | H | CR₃ | O | 74–75 |
| 1-32 | 6-OBn | OMe | OMe | H | Me | H | CR₃ | O | 148.5–149 |
| 1-33 | 6-*1 | OMe | OMe | H | Me | H | CR₃ | O | 78–80 |
| 1-34 | 6-*1 | OMe | OMe | H | Me | Ph-4-OMe | CR₃ | O | 136–139 |
| 1-35 | 6-O-Ph | OMe | OMe | H | Me | Ph-4-OMe | CR₃ | O | Gum |
| 1-36 | H | OMe | OMe | H | Et | H | CR₃ | O | |
| 1-37 | H | OMe | OMe | H | Ph | H | CR₃ | O | |
| 1-38 | 6-F | OMe | OMe | H | Me | Me | CR₃ | O | |
| 1-39 | H | OMe | OMe | H | Me | Me | CR₃ | O | |
| 1-40 | H | OMe | OMe | H | Et | Me | CR₃ | O | |
| 1-41 | H | OMe | OMe | H | Ph | Me | CR₃ | O | |
| 1-42 | 6-Cl | OMe | OMe | H | Me | Me | CR₃ | O | |
| 1-43 | 6-Br | OMe | OMe | H | Me | Me | CR₃ | O | |
| 1-44 | 6-I | OMe | OMe | H | Me | Me | CR₃ | O | |
| 1-45 | *6-Cl | OMe | OMe | H | Pr-i | OBt | CR₃ | O | 1.569 (26) |
| 1-46 | 6-Cl | OMe | OMe | H | Pr-i | Bn | CR₃ | O | 1.5832 (25.8) |
| 1-47 | 6-Cl | OMe | OMe | H | H | CH₂SEt | CR₃ | O | 1.5813 (24.5) |
| 1-48 | 6-Cl | OMe | OMe | H | H | CH₂SO₂Et | CR₃ | O | 118–119 |
| 1-49 | 6-Cl | OMe | OMe | H | CH₂OCOMe | Ph | CR₃ | O | Gum |
| 1-50 | 6-Cl | OMe | OMe | H | CH₃OCOMe | Me | CR₃ | O | 78–81 |
| 1-51 | 6-Cl | OMe | OMe | H | CH₂OH | Ph | CR₃ | O | 58–61 |
| 1-52 | 6-Cl | OMe | OMe | H | CH₂OSO₂MNe₂ | Ph | CR₃ | O | powder |
| 1-53 | 6-Cl | OMe | OMe | H | CH₂OCHO | Ph | CR₃ | O | 152–154 |
| 1-54 | 6-Cl | OMe | OMe | H | CH₂OCONHEt | Ph | CR₃ | O | Gum |
| 1-55 | 6-Cl | OMe | OMe | H | CH₂OCOCH₂Cl | Ph | CR₃ | O | Gum |
| 1-56 | 6-Cl | OMe | OMe | H | CH₂OCONHPh-3-Cl | Ph | CR₃ | O | 54–57 |
| 1-57 | 6-Cl | OMe | OMe | H | CH₂OSO₂Me | Ph | CR₃ | O | Gum |
| 1-58 | 6-Cl | OMe | OMe | H | CH₂OCONHPh-4-Br | Ph | CR₃ | O | 58–61 |
| 1-59 | 6-Cl | OMe | OMe | H | CH₂OCONH-Hex-c | Ph | CR₃ | O | 98–100 |
| 1-60 | 6-Cl | OMe | OMe | H | CH₂OCONHPh-3-Cl | Ph | CR₃ | O | 114–116 |
| 1-61 | 6-Cl | OMe | OMe | H | CH₂OCONHPh-2,4-Cl₂ | Ph | CR₃ | O | 59–62 |

TABLE 1-continued

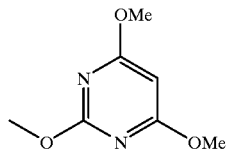

| No. | Xn *2 | R₁ | R₂ | R₃ | R₁₉ | Y₂₀ | A | Z | Physical Data *3 |
|---|---|---|---|---|---|---|---|---|---|
| 1-62 | 6-Cl | OMe | OMe | H | CH₂OCONHPh-4-OMe | Ph | CR₃ | O | 62–64 |
| 1-63 | 6-Cl | OMe | OMe | H | CH₂OCONH-α-naphthyl | Ph | CR₃ | O | 57–59 |
| 1-64 | 6-Cl | OMe | OMe | H | —(CH₂)₅— | | CR₃ | O | 1.5670 (23.5) |
| 1-65 | *1 | OMe | OMe | H | —(CH₂)₅— | | CR₃ | O | 129–131 |
| 1-66 | 6-Cl | OMe | OMe | H | —(CH₂)₆— | | CR₃ | O | 104–106 |
| 1-67 | *1 | OMe | OMe | H | —(CH₂)₆— | | CR₃ | O | 140–141 |

*1

*2 H represents that all Xn are hydrogen. If any position is specially indicated, other positions are bonded with hydrogen. (The same can be applied for Tables 2 onward.)
*3 Physical data represent either a melting point or a refractive index.

TABLE 2

| No. | Xn | R₁ | R₂ | R₃ | R₂₁ | Y₂₂ | A | Z | Physical Data |
|---|---|---|---|---|---|---|---|---|---|
| 2-1 | 6-F | OMe | OMe | H | Me | COOH | CR₃ | O | |
| 2-2 | 6-F | OMe | OMe | H | Me | COOMe | CR₃ | O | |
| 2-3 | 6-F | OMe | OMe | H | Me | Et | CR₃ | O | |
| 2-4 | 6-Cl | OMe | OMe | H | H | H | CR₃ | S | |
| 2-5 | 6-F | OMe | OMe | H | H | H | CR₃ | O | |
| 2-6 | H | OMe | OMe | H | H | H | CR₃ | O | |
| 2-7 | H | OMe | OMe | H | Me | H | CR₃ | O | |
| 2-8 | 6-Cl | OMe | OMe | H | Ph | H | CR₃ | O | |
| 2-9 | 6-F | OMe | OMe | H | Ph | H | CR₃ | O | 1.594 (25) |
| 2-10 | 6-1 | OMe | OMe | H | Ph | H | CR₃ | O | |
| 2-11 | 6-F | OMe | OMe | H | Me | H | CR₃ | O | 81–83 |
| 2-12 | 6-F | OMe | OMe | H | Me | Me | CR₃ | O | |
| 2-13 | 6-F | OMe | OMe | H | Me | Ph | CR₃ | O | |

TABLE 3

| No. | Xn | R₁ | R₂ | R₃ | A | Y₂₃ | Y₂₄ | Z | Physical Data |
|---|---|---|---|---|---|---|---|---|---|
| 3-1 | 5-Cl | OMe | OMe | H | CR₃ | H | H | O | 151–152 |
| 3-2 | 4-Cl | OMe | OMe | H | CR₃ | H | H | O | 125–128 |
| 3-3 | 3-Cl | OMe | OMe | H | CR₃ | H | H | O | 125–127 |
| 3-4 | 2-Cl-4-Cl | OMe | OMe | H | CR₃ | H | H | O | 101–104 |
| 3-5 | 4-Cl-5-Me | OMe | OMe | H | CR₃ | H | H | O | 158–160 |
| 3-6 | 4-Cl-6-Cl | OMe | —OCH₂CH₂— | | CR₃ | H | H | O | |
| 3-7 | 4-COOMe | OMe | OMe | H | CR₃ | H | H | O | 172 |
| 3-8 | 5-Et | OMe | OMe | H | CR₃ | H | H | O | 87–89 |
| 3-9 | 3-F | OMe | OMe | H | CR₃ | H | H | O | 141–142 |
| 3-10 | 3-F | Me | OMe | H | CR₃ | H | H | S | |
| 3-11 | H | OMe | OMe | H | CR₃ | H | H | O | 65–67 |
| 3-12 | H | OMe | OMe | H | CR₃ | H | COOEt | O | 1.553 (23.5) |
| 3-13 | H | OMe | OMe | H | CR₃ | H | COOMe | O | 91–93 |
| 3-14 | H | OMe | OMe | H | CR₃ | H | p-TS | O | 136–138 |
| 3-15 | H | OMe | OMe | H | CR₃ | H | COOH | O | 164–166 |
| 3-16 | H | OMe | OMe | H | CR₃ | H | COOPr-i | O | 111–113 |
| 3-17 | H | CF₃ | —OCH₂CH₂— | H | CR₃ | H | H | O | |
| 3-18 | H | Cl | Cl | H | CR₃ | H | H | O | |
| 3-19 | H | OCF₂H | OCF₂H | H | CR₃ | H | H | O | |
| 3-20 | H | Me | OMe | H | CR₃ | H | H | O | |
| 3-21 | H | Me | OMe | H | CR₃ | H | H | S | |
| 3-22 | H | CF₃ | OMe | H | CR₃ | H | H | O | |
| 3-23 | H | CF₃ | OMe | H | CR₃ | H | H | S | |
| 3-24 | H | OMe | OMe | H | N | H | H | O | |
| 3-25 | H | Me | OMe | H | N | H | H | O | |
| 3-26 | H | OMe | OMe | H | CR₃ | Me | H | O | |
| 3-27 | H | OMe | OMe | H | CR₃ | H | Me | O | |
| 3-28 | H | OMe | OMe | H | CR₃ | Me | Me | O | |
| 3-29 | H | OMe | —OCH₂CH₂— | | CR₃ | H | H | O | |
| 3-30 | H | OMe | —OCH₂CH₂— | | CR₃ | H | H | S | |
| 3-31 | H | Me | —OCH₂CH₂— | | CR₃ | H | H | O | |
| 3-32 | H | Me | —OCH₂CH₂— | | CR₃ | H | H | S | |
| 3-33 | H | CF₃ | —OCH₂CH₂— | | CR₃ | H | H | S | |
| 3-34 | H | OMe | OMe | H | CR₃ | H | H | S | |
| 3-35 | 5-i-Pr | OMe | OMe | H | CR₃ | H | H | O | 1.425 (25) |
| 3-36 | 5-Me | OMe | OMe | H | CR₃ | H | H | O | 115–116 |
| 3-37 | 3-Me-4-OMe | OMe | OMe | H | CR₃ | H | H | O | 147–150 |
| 3-38 | 4-Me-5-Me | OMe | OMe | H | CR₃ | H | H | O | 115–116 |
| 3-39 | 5-Me-6-Cl | OMe | OMe | H | CR₃ | H | H | O | 95–97 |
| 3-40 | 5-Me-6-Me | OMe | OMe | H | CR₃ | H | H | O | 92–94 |
| 3-41 | 4-OMe | OMe | OMe | H | CR₃ | H | H | O | 92–94 |
| 3-42 | 3-OMe | OMe | OMe | H | CR₃ | H | H | O | 148–149 |
| 3-43 | 3-OMe | Me | OMe | H | CR₃ | H | H | O | |
| 3-44 | 3-OMe | CF₃ | OMe | H | CR₃ | H | H | O | |
| 3-45 | 4-OMe | Me | OMe | H | CR₃ | H | H | O | |
| 3-46 | 4-OMe | CF₃ | OMe | H | CR₃ | H | H | O | |
| 3-47 | 4-OMe | OMe | —OCH₂CH₂— | | CR₃ | H | H | O | |
| 3-48 | 5-OMe | Me | OMe | H | CR₃ | H | H | O | |
| 3-49 | *1 | OMe | OMe | H | CR₃ | H | H | O | 130–132 |
| 3-50 | 6-(3,5-Dimethoxybenzoyloxy) | OMe | OMe | H | CR₃ | H | H | O | 139–140 |
| 3-51 | 6-(3,5-Dimethoxybenzyloxy) | OMe | OMe | H | CR₃ | H | H | O | 130–131 |
| 3-52 | 6-(4-Chlorobenzoyloxy) | OMe | OMe | H | CR₃ | H | H | O | |
| 3-53 | 6-Br | OMe | OMe | H | CR₃ | H | H | O | 117–120 |
| 3-54 | 6-Br | OMe | OMe | H | CR₃ | H | Me | O | |
| 3-55 | 6-Br | OMe | OMe | H | CR₃ | Me | H | O | |
| 3-56 | 6-Br | OMe | OMe | H | CR₃ | Me | Me | O | |
| 3-57 | 6-CF₃ | OMe | OMe | H | CR₃ | H | H | O | 100–102 |
| 3-58 | 6-CF₃ | OMe | OMe | H | CR₃ | H | H | S | |
| 3-59 | 6-CH₂Br | OMe | OMe | H | CR₃ | H | H | O | |
| 3-60 | 6-CH₂CN | OMe | OMe | H | CR₃ | H | H | O | |
| 3-61 | 6-CH₂Me | OMe | OMe | H | CR₃ | H | H | O | |
| 3-62 | 6-CH₂SMe | OMe | OMe | H | CR₃ | H | H | O | |

TABLE 3-continued

| No. | Xn | R₁ | R₂ | R₃ | A | Y₂₃ | Y₂₄ | Z | Physical Data |
|---|---|---|---|---|---|---|---|---|---|
| 3-63 | 6-CH₂SO₂Me | OMe | OMe | H | CR₃ | H | H | O | |
| 3-64 | 6-CH₂SO₂Ph | OMe | OMe | H | CR₃ | H | H | O | |
| 3-65 | 6-CH₂SOMe | OMe | OMe | H | CR₃ | H | H | O | |
| 3-66 | 6-CH₂SPh | OMe | OMe | H | CR₃ | H | H | O | |
| 3-67 | 6-Cl | OMe | OMe | H | CR₃ | H | H | O | 112–113 |
| 3-68 | 6-Cl | Me | OMe | H | CR₃ | H | H | O | Gum |
| 3-69 | 6-Cl | Me | OMe | H | CR₃ | H | H | O | 78–80 |
| 3-70 | 6-Cl | CF₃ | —OCH₂CH₂— | | CR₃ | H | H | O | 125–130 |
| 3-71 | 6-Cl | OMe | OMe | H | N | H | H | O | 164–165 |
| 3-72 | 6-Cl | OMe | OMe | H | CR₃ | H | Me | O | Gum |
| 3-73 | 6-Cl | OMe | OMe | H | CR₃ | H | Et | O | 83–86 |
| 3-74 | 6-Cl | OMe | OMe | H | CR₃ | H | Bn | O | 1.67 (25) |
| 3-75 | 6-Cl | OMe | OMe | H | CR₃ | H | H | S | |
| 3-76 | 6-Cl | Me | OMe | H | CR₃ | H | H | S | |
| 3-77 | 6-Cl | CF₃ | OMe | H | CR₃ | H | H | O | |
| 3-78 | 6-Cl | CF₃ | OMe | H | CR₃ | H | H | S | |
| 3-79 | 6-Cl | OMe | OMe | H | CR₃ | H | COOEt | S | |
| 3-80 | 6-Cl | OMe | OMe | H | CR₃ | H | COOH | S | |
| 3-81 | 6-Cl | OMe | OMe | H | CR₃ | Me | H | O | |
| 3-82 | 6-Cl | OMe | OMe | H | CR₃ | Me | Me | O | Gum |
| 3-83 | 6-Cl | OMe | —OCH₂CH₂— | | CR₃ | H | H | O | |
| 3-84 | 6-Cl | OMe | —OCH₂CH₂— | | CR₃ | H | H | S | |
| 3-85 | 6-Cl | Me | —OCH₂CH₂— | | CR₃ | H | H | O | |
| 3-86 | 6-Cl | Me | —OCH₂CH₂— | | CR₃ | H | H | S | |
| 3-87 | 6-Cl | CF₃ | —OCH₂CH₂— | | CR₃ | H | H | S | |
| 3-88 | 6-CN | OMe | OMe | H | CR₃ | H | H | O | |
| 3-89 | 6-COOH | OMe | OMe | H | CR₃ | H | H | O | 76–80 |
| 3-90 | 6-COOMe | OMe | OMe | H | CR₃ | H | H | O | 112–113 |
| 3-91 | 6-Et | OMe | OMe | H | CR₃ | H | H | O | |
| 3-92 | 6-F | OMe | OMe | H | CR₃ | H | H | O | 77–78 |
| 3-93 | 6-F | OMe | OMe | H | CR₃ | H | Me | O | 1.474 (25) |
| 3-94 | 6-F | OMe | OMe | H | CR₃ | Me | H | O | 121–123 |
| 3-95 | 6-F | OMe | OMe | H | CR₃ | H | H | S | |
| 3-96 | 6-F | Me | OMe | H | CR₃ | H | H | O | |
| 3-97 | 6-F | Me | OMe | H | CR₃ | H | H | S | |
| 3-98 | 6-F | CF₃ | OMe | H | CR₃ | H | H | O | |
| 3-99 | 6-F | CF₃ | OMe | H | CR₃ | H | H | S | |
| 3-100 | 6-F | OMe | OMe | H | CR₃ | Me | Me | O | |
| 3-101 | 6-F | OMe | —OCH₂CH₂— | | CR₃ | H | H | O | |
| 3-102 | 6-F | OMe | —OCH₂CH₂— | | CR₃ | H | H | S | |
| 3-103 | 5-OMe | OMe | OMe | H | CR₃ | H | H | O | 123–125 |
| 3-104 | 5-OMe | CF₃ | OMe | H | CR₃ | H | H | O | |
| 3-105 | 5-t-Bu | OMe | OMe | H | CR₃ | H | H | O | Gum |
| 3-106 | 6-(p-Toluenesulfonyloxy) | OMe | OMe | H | CR₃ | H | H | O | 111–112 |
| 3-107 | 6-Cl | OMe | OMe | H | CR₃ | Me | H | O | 95–96 |
| 3-108 | 6-Cl | OMe | OMe | H | CR₃ | H | CONMe₂ | O | 162–165 |
| 3-109 | 6-Cl | OMe | OMe | H | CR₃ | H | COOEt | O | 77–79 |
| 3-110 | 6-Cl | OMe | OMe | H | CR₃ | Ph | H | O | 92–96 |
| 3-111 | 6-Cl | OMe | OMe | H | CR₃ | Et | H | O | 1.569 (25.5) |
| 3-112 | 6-Cl | OMe | OMe | H | CR₃ | Ph-4-Cl | H | O | 128–130 |
| 3-113 | 6-Cl | OMe | OMe | H | CR₃ | Me | Me | O | Gum |
| 3-114 | 6-Cl | OMe | OMe | H | CR₃ | H | CH₂OAc | O | 198–199 |
| 3-115 | 6-Cl | OMe | OMe | H | CR₃ | CH₂OMe | H | O | 1.566 (23.5) |
| 3-116 | 6-Cl | OMe | OMe | H | CR₃ | Bu-i | H | O | 1.559 (23.5) |
| 3-117 | 6-Cl | OMe | OMe | H | CR₃ | Ph-2-OH-4-Cl | H | O | 154–157 |
| 3-118 | 6-Cl | OMe | OMe | H | CR₃ | Pr | Me | O | 1.5535 (24) |
| 3-119 | 6-Cl | OMe | OMe | H | CR₃ | Ph-4-Cl | Me | O | Gum |
| 3-120 | 6-Cl | OMe | OMe | H | CR₃ | CH(SMe)Pr-i | H | O | 1.5788(25) |
| 3-121 | 6-*1 | OMe | OMe | H | CR₃ | H | H | O | 225–227 |
| 3-122 | 6-COOEt | OMe | OMe | H | CR₃ | H | Me | O | 1.5545 (26) |
| 3-123 | 6-COOMe | OMe | OMe | H | CR₃ | H | Me | O | 78–81 |
| 3-124 | 6-COOPr-i | OMe | OMe | H | CR₃ | H | H | O | Oil |

TABLE 3-continued

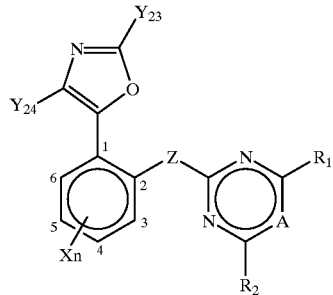

| No. | Xn | $R_1$ | $R_2$ | $R_3$ | A | $Y_{23}$ | $Y_{24}$ | Z | Physical Data |
|---|---|---|---|---|---|---|---|---|---|
| 3-125 | 6-F | Me | —OCH$_2$CH$_2$— | | CR$_3$ | H | H | O | |
| 3-126 | 6-F | Me | —OCH$_2$CH$_2$— | | CR$_3$ | H | H | S | |
| 3-127 | 6-F | CF$_3$ | —OCH$_2$CH$_2$— | | CR$_3$ | H | H | O | |
| 3-128 | 6-F | CF$_3$ | —OCH$_2$CH$_2$— | | CR$_3$ | H | H | S | |
| 3-129 | 6-F | OMe | OMe | H | CR$_3$ | CH$_2$CH$_2$Ph | H | O | 1.578 (26) |
| 3-130 | 6-F | OMe | OMe | H | CR$_3$ | Et | H | O | 65–68 |
| 3-131 | 6-F | OMe | OMe | H | CR$_3$ | Ph | H | O | 87–89 |
| 3-132 | 6-F | OMe | OMe | H | CR$_3$ | H | Br | O | 88–92 |
| 3-133 | 6-F | OMe | OMe | H | CR$_3$ | Me | CH$_2$OBn | O | 56–57 |
| 3-134 | 6-F | OMe | OMe | H | CR$_3$ | H | CH$_2$OMe | O | 84–87 |
| 3-135 | 6-F | OMe | OMe | H | CR$_3$ | Me | Me | O | 1.549 (25) |
| 3-136 | H | OMe | OMe | H | CR$_3$ | H | COOEt | S | 79–82 |
| 3-137 | H | OMe | OMe | H | CR$_3$ | Ph | Me | O | |
| 3-138 | 6-H | OMe | OMe | H | CR$_3$ | Me | Me | O | 1.5678 (25.5) |
| 3-139 | 6-I | OMe | OMe | H | CR$_3$ | H | H | O | 128–130 |
| 3-140 | 6-I | OMe | OMe | H | CR$_3$ | H | Me | O | |
| 3-141 | 6-I | OMe | OMe | H | CR$_3$ | Me | H | O | |
| 3-142 | 6-I | OMe | OMe | H | CR$_3$ | Me | Me | O | |
| 3-143 | 6-i-Pr | OMe | OMe | H | CR$_3$ | H | H | O | |
| 3-144 | 6-Me | OMe | OMe | H | CR$_3$ | H | H | O | 125–128 |
| 3-145 | 6-Me | OMe | OMe | H | CR$_3$ | H | H | S | |
| 3-146 | 6-Me-4-Oe | OMe | OMe | H | CR$_3$ | H | H | O | 96–99 |
| 3-147 | 6-NH$_2$ | OMe | OMe | H | CR$_3$ | H | H | O | 95–97 |
| 3-148 | 6-NO$_2$ | OMe | OMe | H | CR$_3$ | H | H | O | 144–146 |
| 3-149 | 6-NO$_2$ | OMe | OMe | H | CR$_3$ | H | H | S | |
| 3-150 | 6-OAc | OMe | OMe | H | CR$_3$ | H | H | O | Gum |
| 3-151 | 6-OAllyl | OMe | OMe | H | CR$_3$ | H | H | O | 1.572 (25) |
| 3-152 | 6-OBn | OMe | OMe | H | CR$_3$ | H | H | O | 137–138 |
| 3-153 | 6-OC$_3$H$_6$COOEt | OMe | OMe | H | CR$_3$ | H | H | O | 1.551 (25) |
| 3-154 | 6-OC$_3$H$_6$COOH | OMe | OMe | H | CR$_3$ | H | H | O | 159–160 |
| 3-155 | 6-OC$_5$H$_{11}$-n | OMe | OMe | H | CR$_3$ | H | H | O | 1.532 (25) |
| 3-156 | 6-OCH$_2$C.CH | OMe | OMe | H | CR$_3$ | H | H | O | 120–121 |
| 3-157 | 6—OCH$_2$COOEt | OMe | OMe | H | CR$_3$ | H | H | O | 95–97 |
| 3-158 | 6—OCH$_2$OMe | OMe | OMe | H | CR$_3$ | H | H | O | 1.437 (25) |
| 3-159 | 6—OCH$_2$SMe | OMe | OMe | H | CR$_3$ | H | H | O | |
| 3-160 | 6—OCH$_2$SO$_2$Me | OMe | OMe | H | CR$_3$ | H | H | O | |
| 3-161 | 6-OCONHEt | OMe | OMe | H | CR$_3$ | H | H | O | 118–120 |
| 3-162 | 6-OCNHHex-c | OMe | OMe | H | CR$_3$ | H | H | O | 143–144 |
| 3-163 | 6-OCNHHex-n | OMe | OMe | H | CR$_3$ | H | H | O | 94 |
| 3-164 | 6-OCSNHCOOEt | OMe | OMe | H | CR$_3$ | H | H | O | Gum |
| 3-165 | 6-OEt | OMe | OMe | H | CR$_3$ | H | H | O | 87–88 |
| 3-166 | 6-OH | OMe | OMe | H | CR$_3$ | H | H | O | 45–48 |
| 3-167 | 6-OMe | OMe | OMe | H | CR$_3$ | H | H | O | 92–94 |
| 3-168 | 6-OMe | OMe | OMe | H | CR$_3$ | H | H | S | |
| 3-169 | 6-OMe | Me | OMe | H | CR$_3$ | H | H | O | |
| 3-170 | 6-OMe | CF$_3$ | OMe | H | CR$_3$ | H | H | O | |
| 3-171 | 6-OMe | OMe | —OCH$_2$CH$_2$— | | CR$_3$ | H | H | O | |
| 3-172 | 6-OPr-i | OMe | OMe | H | CR$_3$ | H | H | O | Gum |
| 3-173 | 6-Ph | OMe | OMe | H | CR$_3$ | H | H | O | 117–118 |
| 3-174 | 6-Ph-2-Me-4-Cl | OMe | OMe | H | CR$_3$ | H | H | O | Oil |
| 3-175 | 6-Ph-4-Cl | OMe | OMe | H | CR$_3$ | H | H | O | 108–110 |
| 3-176 | 6-Ph-4-Bt | OMe | OMe | H | CR$_3$ | H | H | O | Oil |
| 3-177 | 6-Ph-4-Pr-i | OMe | OMe | H | CR$_3$ | H | H | O | 1.5681 (25) |
| 3-178 | 6-SH | OMe | OMe | H | CR$_3$ | H | H | O | |
| 3-179 | 6-SMe | OMe | OMe | H | CR$_3$ | H | H | O | 89–90 |
| 3-180 | 6-SMe | OMe | OMe | H | CR$_3$ | H | H | S | |
| 3-181 | 6-SO$_2$Me | OMe | OMe | H | CR$_3$ | H | H | O | 171–173 |
| 3-182 | 6-SO$_2$Me | OMe | OMe | H | CR$_3$ | H | H | S | |
| 3-183 | 6-SO$_2$Ph | OMe | OMe | H | CR$_3$ | H | H | O | 142–145 |
| 3-184 | 6-SO$_2$Ph | OMe | OMe | H | CR$_3$ | H | H | S | |
| 3-185 | 6-SOMe | OMe | OMe | H | CR$_3$ | H | H | O | |
| 3-186 | 6-SOMe | OMe | OMe | H | CR$_3$ | H | H | S | |

TABLE 3-continued

| No. | Xn | $R_1$ | $R_2$ | $R_3$ | A | $Y_{23}$ | $Y_{24}$ | Z | Physical Data |
|---|---|---|---|---|---|---|---|---|---|
| 3-187 | 6-SOPh | OMe | OMe | H | $CR_3$ | H | H | O | |
| 3-188 | 6-SOPh | OMe | OMe | H | $CR_3$ | H | H | S | |
| 3-189 | 6-SPh | OMe | OMe | H | $CR_3$ | H | H | O | |
| 3-190 | 6-SPh | OMe | OMe | H | $CR_3$ | H | H | S | |
| 3-191 | 6-t-Bu | OMe | OMe | H | $CR_3$ | H | H | S | |
| 3-192 | 6-Cl | OMe | OMe | H | $CR_3$ | Et | Me | O | 1.5535 (24) |
| 3-193 | 4-Ph | OMe | OMe | H | $CR_3$ | H | Me | O | 84–86 |
| 3-194 | 6-Cl | OMe | OMe | H | $CR_3$ | Ph-4-OMe | Me | O | 119–121 |
| 3-195 | 6-F | OMe | OMe | H | $CR_3$ | SEt | Me | O | Gum |
| 3-196 | 6-*1 | OMe | OMe | H | $CR_3$ | Ph-4-OMe | Me | O | 150–153 |
| 3-197 | 6-Cl | OMe | OMe | H | $CR_3$ | CH=C(Me)$_2$ | Me | O | Gum |
| 3-198 | 6-Cl | OMe | OMe | H | $CR_3$ | CH$_2$Pr | Me | O | Gum |
| 3-199 | 6-*1 | OMe | OMe | H | $CR_3$ | Ph | Me | O | 149–151 |
| 3-200 | 6-Cl | OMe | OMe | H | $CR_3$ | Et | Me | O | 1.552 (23.2) |
| 3-201 | 6-Cl | OMe | OMe | H | $CR_3$ | Pr | H | O | 1.567 (23) |
| 3-202 | 6-Cl | OMe | OMe | H | $CR_3$ | Ph-3,4--(OMe)$_2$ | H | O | Gum |
| 3-203 | 6-Ph | OMe | OMe | H | $CR_3$ | Me | H | O | Gum |
| 3-204 | 6-Cl | OMe | OMe | H | $CR_3$ | 3-pyridyl | H | O | 105–108 |
| 3-205 | 6-Cl | OMe | OMe | H | $CR_3$ | Ph-4-NMe$_2$ | H | O | Gum |
| 3-206 | 6-Cl | OMe | OMe | H | $CR_3$ | C(Me)=CHEt | H | O | 86–88 |
| 3-207 | 6-Cl | OMe | OMe | H | $CR_3$ | Ph-4--NHCOCHCl$_2$ | H | O | 176–179 |
| 3-208 | 6-Cl | OMe | OMe | H | $CR_3$ | CH=NOMe | H | O | 1.401 (25) |
| 3-209 | 5,6-Cl$_2$ | OMe | OMe | H | $CR_3$ | H | H | O | 117–119 |
| 3-210 | 6-Cl | OMe | OMe | H | $CR_3$ | CH$_2$-*1 | H | O | Gum |
| 3-211 | 6-Cl | OMe | OMe | H | $CR_3$ | CH(OMe)$_2$ | H | O | 1.544 (23) |
| 3-212 | 6-Ph | OMe | OMe | H | $CR_3$ | CHO | H | O | 118–119 |
| 3-213 | 6-Cl | OMe | OMe | H | $CR_3$ | CH=CHPh | H | O | 1.6165 (25.5) |
| 3-214 | 6-Cl | OMe | OMe | H | $CR_3$ | CH=CHCO$_2$Et | H | O | 74–78 |
| 3-215 | 6-*2 | OMe | OMe | H | $CR_3$ | H | H | O | 124–125 |
| 3-216 | 6-Cl | OMe | OMe | H | $CR_3$ | CH=CHCN | H | O | 96–98 |
| 3-217 | 6-Cl | OMe | OMe | H | $CR_3$ | a-naphthyl | H | O | 1.6156 (27) |
| 3-218 | 6-Cl | OPr$^i$ | OPr$^i$ | H | $CR_3$ | a-naphthyl | H | O | 94–96 |
| 3-219 | 6-Cl | OMe | OMe | H | $CR_3$ | Ph-4-NH$_2$ | H | O | Gum |
| 3-220 | 6-Cl | OMe | OMe | H | $CR_3$ | CH$_2$OMe | H | O | 1.5432 (24) |
| 3-221 | 6-Cl | OMe | OMe | H | $CR_3$ | CH=CHCOMe | H | O | 95–100 |
| 3-222 | 6-Cl | OMe | OMe | H | $CR_3$ | Ph-2,6-Me$_2$ | H | O | 134–136 |
| 3-223 | 6-Cl | OMe | OMe | H | $CR_3$ | CH=NOEt | H | O | 1.5635 (26.5) |
| 3-224 | 5-NMe$_2$-6-F | OMe | OMe | H | $CR_3$ | H | H | O | 100–101 |
| 3-225 | 6-Cl | OMe | OMe | H | $CR_3$ | Ph-4-NHCOCH$_2$Cl | H | O | 136–141 |

*1

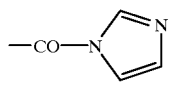

*1

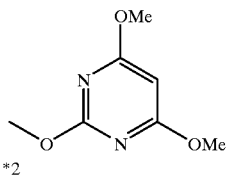

*2

TABLE 3-continued

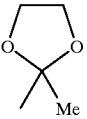

| No. | Xn | R₁ | R₂ | R₃ | A | Y₂₃ | Y₂₄ | Z | Physical Data |
|---|---|---|---|---|---|---|---|---|---|

TABLE 4

| No. | X'n | R₁ | R₂ | R₃ | A | Y₂₃ | Y₂₄ | Z | Physical Data |
|---|---|---|---|---|---|---|---|---|---|
| 4-1 | 2,3-Dimethyl | OMe | OMe | H | CR₃ | H | H | O | 80–82 |
| 4-2 | 2,4,6-Trimethyl | OMe | OMe | H | CR₃ | H | H | O | 163–165 |
| 4-3 | 2,4-Dimethyl | OMe | OMe | H | CR₃ | H | H | O | 99–102 |
| 4-4 | 2,5-Dimethyl | OMe | OMe | H | CR₃ | H | H | O | Gum |
| 4-5 | 2,6-Dimethyl | OMe | OMe | H | CR₃ | H | H | O | 141–143 |
| 4-6 | 2-(CH)4-3 | OMe | OMe | H | CR₃ | H | H | O | 89–92 |
| 4-7 | 2-Cl | OMe | OMe | H | CR₃ | H | H | O | |
| 4-8 | 2-CN | OMe | OMe | H | CR₃ | H | H | O | |
| 4-9 | 2-CONH₂ | OMe | OMe | H | CR₃ | H | H | O | |
| 4-10 | 2-F | OMe | OMe | H | CR₃ | H | H | O | |
| 4-11 | 2-Me | OMe | OMe | H | CR₃ | H | H | O | 130–132 |
| 4-12 | 2-NH₂-4-CF₃ | OMe | OMe | H | CR₃ | H | H | O | |
| 4-13 | 2-NO₂ | OMe | OMe | H | CR₃ | H | H | O | |
| 4-14 | 2-NO₂-CF₃ | OMe | OMe | H | CR₃ | H | H | O | 108–109 |
| 4-15 | 2-OMe | OMe | OMe | H | CR₃ | H | H | O | 120–122 |
| 4-16 | 2-Ph | OMe | OMe | H | CR₃ | H | H | O | 119–121 |
| 4-17 | 3,4-Dimethyl | OMe | OMe | H | CR₃ | H | H | O | Gum |
| 4-18 | 3,5-Dimethoxy | OMe | OMe | H | CR₃ | H | H | O | 107–110 |
| 4-19 | 3,5-Dimethyl | OMe | OMe | H | CR₃ | H | H | O | Gum |
| 4-20 | 3-Bu-t | OMe | OMe | H | CR₃ | H | H | O | 1.548 (25) |
| 4-21 | 3-Cl | OMe | OMe | H | CR₃ | H | H | O | 1.5924 (26.6) |
| 4-22 | 3-CN | OMe | OMe | H | CR₃ | H | H | O | |
| 4-23 | 3-F | OMe | OMe | H | CR₃ | H | H | O | |
| 4-24 | 3-Me | OMe | OMe | H | CR₃ | H | H | O | 70–72 |
| 4-25 | 3-NMe₂ | OMe | OMe | H | CR₃ | H | H | O | 1.594 (25) |
| 4-26 | 3-NO₂ | OMe | OMe | H | CR₃ | H | H | O | |
| 4-27 | 3-OMe | OMe | OMe | H | CR₃ | H | H | O | Gum |
| 4-28 | 4-Cl | OMe | OMe | H | CR₃ | H | H | O | 92–95 |
| 4-29 | 4-CN | OMe | OMe | H | CR₃ | H | H | O | Gum |
| 4-30 | 4-P | OMe | OMe | H | CR₃ | H | H | O | 73–75 |
| 4-31 | 4-Me | OMe | OMe | H | CR₃ | H | H | O | 125–127 |
| 4-32 | 4-NO₂ | OMe | OMe | H | CR₃ | H | H | O | |
| 4-33 | 4-OMe | OMe | OMe | H | CR₃ | H | H | O | 94–96 |
| 4-34 | H | OMe | OMe | H | CR₃ | H | H | O | 1.603 (25.5) |

TABLE 4-continued

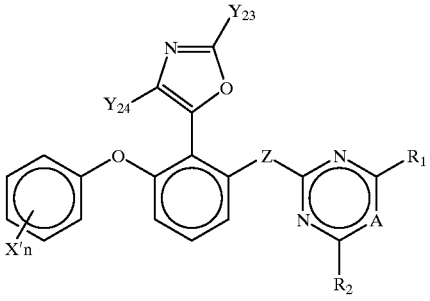

| No. | X' n | R₁ | R₂ | R₃ | A | Y₂₃ | Y₂₄ | Z | Physical Data |
|---|---|---|---|---|---|---|---|---|---|
| 4-35 | H | OMe | OMe | H | N | H | H | O | 97–99 |
| 4-36 | H | OMe | OMe | H | CR₃ | H | Me | O | 1.571 (25) |
| 4-37 | H | Me | Me | H | CR₃ | H | H | O | |
| 4-38 | H | OMe | OMe | H | CR₃ | H | Bn | O | |
| 4-39 | H | OMe | OMe | H | CR₃ | Me | Me | O | |
| 4-40 | H | OMe | OMe | H | CR₃ | Me | H | O | 1.5902 (26.5) |
| 4-41 | H | OMe | OMe | H | CR₃ | Ph | H | O | |
| 4-42 | H | OMe | OMe | H | CR₃ | Ph-4-OMe | H | O | |
| 4-43 | H | OMe | OMe | H | CR₃ | Ph | Me | O | |
| 4-44 | H | OMe | OMe | H | CR₃ | Ph-4-Cl | H | O | |
| 4-45 | H | OMe | OMe | H | CR₃ | Bu-i | H | O | |
| 4-46 | H | OMe | OMe | H | CR₃ | Pr | H | O | |
| 4-47 | H | OMe | OMe | H | CR₃ | Ph | Ph | O | |

TABLE 5

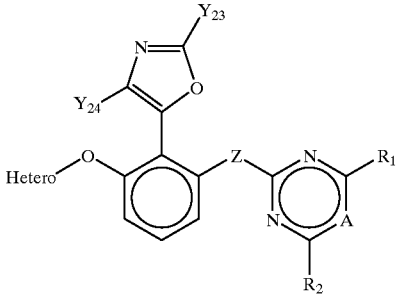

| No. | Hetero | R₁ | R₂ | R₃ | A | Y₂₃ | Y₂₄ | Z | Physical Data |
|---|---|---|---|---|---|---|---|---|---|
| 5-1 | 2-methanesulfonyl-6-methoxy-4-pyrimidyl | OMe | OMe | H | CR₃ | H | H | O | |
| 5-2 | 2-pyridyl | OMe | OMe | H | CR₃ | H | H | O | |
| 5-3 | 2-pyrimidyl | OMe | OMe | H | CR₃ | H | H | O | |
| 5-4 | 3,5-dichloro-2-pyridyl | OMe | OMe | H | CR₃ | H | H | O | |
| 5-5 | 3-chloro-5-trifluoromethyl-2-pyridyl | OMe | OMe | H | CR₃ | H | H | O | Gum |
| 5-6 | 3-pyridyl | OMe | OMe | H | CR₃ | H | H | O | 103–105 |
| 5-7 | 4,6-dimethoxy-2-pyrimidyl | OMe | OMe | H | CR₃ | H | CH₂OBn | O | 1.477 (26.4) |
| 5-8 | 4,6-dimethoxy-2-pyrimidyl | OMe | OMe | H | CR₃ | Me | Me | O | 137–138.5 |
| 5-9 | 4,6-dimethoxy-2-pyrimidyl | OMe | OMe | H | CR₃ | Bn | H | O | |
| 5-10 | 4,6-dimethoxy-2-pyrimidyl | OMe | OMe | H | CF₃ | Et | H | O | |
| 5-11 | 4,6-dimethoxy-2-pyrimidyl | OMe | OMe | H | CR₃ | H | H | O | |
| 5-12 | 4,6-dimethoxy-2-pyrimidyl | OMe | OMe | H | CR₃ | H | Me | O | 91–94 |
| 5-13 | 4,6-dimethoxy-2-pyrimidyl | OMe | OMe | H | CR₃ | Me | H | O | 120–122 |
| 5-14 | 4,6-dimethoxy-2-triazyl | OMe | OMe | H | CR₃ | H | H | O | Gum |
| 5-15 | 4,6-dimethoxy-2-triazyl | OMe | OMe | | N | H | H | O | |
| 5-16 | 4,6-dimethoxy-5-bromo-2-pyrimidyl | OMe | OMe | H | CR₃ | Me | H | O | 138–140 |
| 5-17 | 4,6-dimethyl-2-pyrimidyl | OMe | OMe | H | CR₃ | H | H | O | Gum |
| 5-18 | 4-chloro-6-methyl-2-pyrimidyl | OMe | OMe | H | CR₃ | H | H | O | |
| 5-19 | 4-methoxy-6-methyl-2-pyrimidyl | OMe | OMe | H | CR₃ | H | H | O | 142–143 |
| 5-20 | 4-methoxy-6-methyl-2-pyrimidyl | OMe | OMe | H | CR₃ | H | Me | O | |
| 5-21 | 4-methoxy-6-methyl-2-pyrimidyl | OMe | OMe | H | CR₃ | Me | H | O | |

TABLE 5-continued

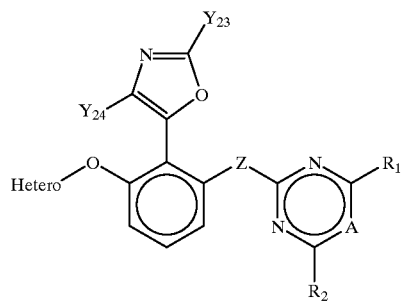

| No. | Hetero | $R_1$ | $R_2$ | $R_3$ | A | $Y_{23}$ | $Y_{24}$ | Z | Physical Data |
|---|---|---|---|---|---|---|---|---|---|
| 5-22 | 4-pyridyl | OMe | OMe | H | $CR_3$ | H | H | O | |
| 5-23 | 6-chloro-2-pyridyl | OMe | OMe | H | $CR_3$ | H | H | O | |
| 5-24 | 6-trifluoromethyl-2-pyridyl | OMe | OMe | H | $CR_3$ | H | H | O | |

TABLE 6

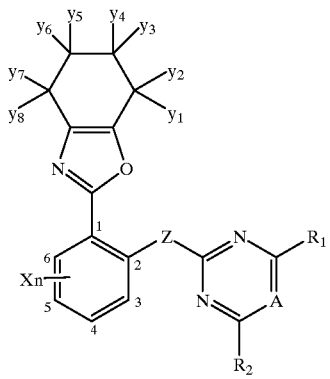

| No. | Xn *1 | $R_1$ | $R_2$ | $R_3$ | $y_1$ | $y_2$ | $y_3$ | $y_4$ | $y_5$ | $y_6$ | $y_7$ | $y_8$ | A | Z | Physical Data *2 |
|---|---|---|---|---|---|---|---|---|---|---|---|---|---|---|---|
| 6-1 | H | OMe | OMe | H | H | H | H | H | H | H | H | H | $CR_3$ | O | 90–92 |
| 6-2 | 6-Cl | OMe | OMe | H | H | H | H | H | H | H | H | H | $CR_3$ | O | 91–92 |
| 6-3 | 6-Cl | OMe | OMe | H | Me | H | H | H | H | H | H | H | $CR_3$ | O | |
| 6-4 | 6-Cl | OMe | OMe | H | H | H | Me | H | H | H | H | H | $CR_3$ | O | 1.5648 (27) |
| 6-5 | 6-Cl | OMe | OMe | H | H | H | H | H | Me | H | H | H | $CR_3$ | O | 1.5551 (22.5) |
| 6-6 | 6-Cl | OMe | OMe | H | H | H | H | H | H | H | Me | H | $CR_3$ | O | |
| 6-7 | 6-Cl | OMe | OMe | H | Me | Me | H | H | H | H | H | H | $CR_3$ | O | |
| 6-8 | 6-Cl | OMe | OMe | H | H | H | Me | Me | H | H | H | H | $CR_3$ | O | Gum |
| 6-9 | 6-Cl | OMe | OMe | H | H | H | H | H | Me | Me | H | H | $CR_3$ | O | |
| 6-10 | 6-Cl | OMe | OMe | H | H | H | H | H | H | H | Me | Me | $CR_3$ | O | |
| 6-11 | 6-Cl | OMe | OMe | H | Et | H | H | H | H | H | H | H | $CR_3$ | O | |
| 6-12 | 6-Cl | OMe | OMe | H | H | H | Et | H | H | H | H | H | $CR_3$ | O | 1.5618 (25) |
| 6-13 | 6-Cl | OMe | OMe | H | H | H | H | H | Et | H | H | H | $CR_3$ | O | 1.5581 (24.5) |
| 6-14 | 6-Cl | OMe | OMe | H | H | H | H | H | H | H | Et | H | $CR_3$ | O | |
| 6-15 | 6-Cl | OMe | OMe | H | i-Pr | H | H | H | H | H | H | H | $CR_3$ | O | |
| 6-16 | 6-Cl | OMe | OMe | H | H | H | i-Pr | H | H | H | H | H | $CR_3$ | O | |
| 6-17 | 6-Cl | OMe | OMe | H | H | H | H | H | i-Pr | R | H | H | $CR_3$ | O | |
| 6-18 | 6-Cl | OMe | OMe | H | | =O | H | H | H | H | H | H | $CR_3$ | O | |
| 6-19 | 6-Cl | OMe | OMe | H | H | H | | =O | H | H | H | H | $CR_3$ | O | |
| 6-20 | 6-Cl | OMe | OMe | H | H | H | H | H | | =O | H | H | $CR_3$ | O | |
| 6-21 | 6-Cl | OMe | OMe | H | H | H | H | H | H | H | | =O | $CR_3$ | O | |
| 6-22 | 6-Cl | OMe | OMe | H | | =O | H | H | Me | H | H | H | $CR_3$ | O | |
| 6-23 | 6-Cl | OMe | OMe | H | H | H | | =O | Me | H | H | H | $CR_3$ | O | |
| 6-24 | 6-Cl | OMe | OMe | H | H | H | H | H | | =O | Me | H | $CR_3$ | O | |
| 6-25 | 6-Cl | OMe | OMe | H | | =O | H | H | Me | Me | H | H | $CR_3$ | O | |
| 6-26 | 6-Cl | OMe | OMe | H | | =O | H | H | Me | Me | Me | H | $CR_3$ | O | |
| 6-27 | 6-F | OMe | OMe | H | H | H | H | H | H | H | H | H | $CR_3$ | O | 1.554 (27) |
| 6-28 | 6-F | OMe | OMe | H | Me | H | H | H | H | H | H | H | $CR_3$ | O | |
| 6-29 | 6-F | OMe | OMe | H | H | H | Me | H | H | H | H | H | $CR_3$ | O | |
| 6-30 | 6-F | OMe | OMe | H | H | H | H | H | Me | H | H | H | $CR_3$ | O | |
| 6-31 | 6-F | OMe | OMe | H | H | H | H | H | H | H | Me | H | $CR_3$ | O | |
| 6-32 | 6-Br | OMe | OMe | H | H | H | H | H | H | H | Me | H | $CR_3$ | O | |
| 6-33 | 6-I | OMe | OMe | H | H | H | H | H | H | H | H | H | $CR_3$ | O | |
| 6-34 | 6-OPn | OMe | OMe | H | H | H | H | H | H | H | H | H | $CR_3$ | O | 100–102 |

TABLE 6-continued

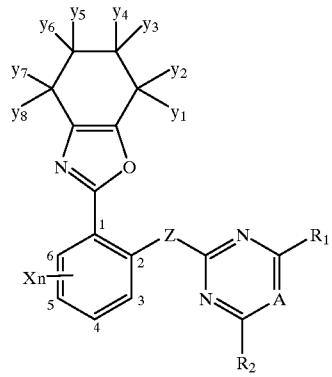

| No. | Xn *1 | R₁ | R₂ | R₃ | y₁ | y₂ | y₃ | y₄ | y₅ | y₆ | y₇ | y₈ | A | Z | Physical Data *2 |
|---|---|---|---|---|---|---|---|---|---|---|---|---|---|---|---|
| 6-35 | 6-Ph | OMe | OMe | H | H | H | H | H | H | H | H | H | CR₃ | O | Gum |
| 6-36 | 6-COOMe | OMe | OMe | H | H | H | H | H | H | H | H | H | CR₃ | O | |
| 6-37 | 6-OMe | OMe | OMe | H | H | H | H | H | H | H | H | H | CR₃ | O | Gum |
| 6-38 | 6-Me | OMe | OMe | H | H | H | H | H | H | H | H | H | CR₃ | O | |
| 6-39 | 6-C(=NOMe)Me | OMe | OMe | H | H | H | H | H | H | H | H | H | CR₃ | O | |
| 6-40 | 6-CH=CH₂ | OMe | OMe | H | H | H | H | H | H | H | H | H | CR₃ | O | Oil |
| 6-41 | 6-OBn | OMe | OMe | H | H | H | H | H | H | H | H | H | CR₃ | O | 102–103 |
| 6-42 | 6-O-c-C₅H₉ | OMe | OMe | H | H | H | H | H | H | H | H | H | CR₃ | O | 65–67 |
| 6-43 | 6-OCH₂CH=CHCl | OMe | OMe | H | H | H | H | H | H | H | H | H | CR₃ | O | 1.564 (27° C.) |
| 6-44 | 6-OH | OMe | OMe | H | H | H | H | H | H | H | H | H | CR₃ | O | 96–98 |
| 6-45 | 6-OSO₂CF₃ | OMe | OMe | H | H | H | H | H | H | H | H | H | CR₃ | O | 76–78 |
| 6-46 | 6-OPh(2-Me) | OMe | OMe | H | H | H | H | H | H | H | H | H | CR₃ | O | |
| 6-47 | 6-Cl | OMe | OMe | H | H | H | H | H | H | H | H | H | CR₃ | S | |
| 6-48 | 6-Cl | OMe | OMe | H | H | H | H | H | H | H | H | H | N | S | |
| 6-49 | 6-Cl | OMe | OMe | H | H | H | H | H | H | H | H | H | N | O | |
| 6-50 | 6-*3 | OMe | OMe | H | H | H | H | H | H | H | H | H | CR₃ | O | Gum |
| 6-51 | 6-I | OMe | OMe | H | H | H | H | H | Me | H | H | H | CR₃ | O | 142.5–143.5 |
| 6-52 | 6-Cl | OMe | OMe | H | H | H | H | H | Buᵗ | H | H | H | CR₃ | O | 129–131 |
| 6-53 | 6-*3 | OMe | OMe | H | H | H | Buᵗ | H | H | H | H | H | CR₃ | O | 1.5526 (25.5) |
| 6-54 | 6-Cl | OMe | OMe | H | H | H | H | H | H | H | H | H | CR₃ | O | Gum |
| 6-55 | 6-*3 | OMe | OMe | H | H | H | H | H | H | H | H | H | CR₃ | O | 1.5350 (27) |
| 6-56 | 6-*3 | OMe | OMe | H | H | H | H | H | H | H | H | H | CR₃ | O | 47–49 |
| 6-57 | 6-OPh(2-Me) | OMe | OMe | H | H | H | H | H | H | H | H | H | CR₃ | O | 1.5636 (22) |
| 6-58 | 6-CO₂Et | OMe | OMe | H | H | H | H | H | H | H | H | H | CR₃ | O | Gum |
| 6-59 | 6-CO₂Me | OMe | OMe | H | H | H | H | H | H | H | H | H | CR₃ | O | Gum |
| 6-60 | 6-CONH₂ | OMe | OMe | H | H | H | H | H | H | H | H | H | CR₃ | O | 185 (dec.) |
| 6-61 | 6-*3 | OMe | OMe | H | H | H | H | H | H | H | H | H | CR₃ | O | 1.5445 (26) |
| 6-62 | 6-CONMe₂ | OMe | OMe | H | H | H | H | H | H | H | H | H | CR₃ | C | 1.5594 (21) |
| 6-63 | 6-COOH | OMe | OMe | H | H | H | H | H | H | H | H | H | CR₃ | O | 186–187 |
| 6-64 | 6-Ph(4-F) | OMe | OMe | H | H | H | H | H | H | H | H | H | CR₃ | C | 1.5604 (26) |
| 6-65 | 6-COOBn | OMe | OMe | H | H | H | H | H | H | H | H | H | CR₃ | O | 1.5560 (21) |
| 6-66 | 6-CO₂CH₂C≡CH | OMe | OMe | H | H | H | H | H | H | H | H | H | CR₃ | O | Gum |
| 6-67 | 6-CONHPh | OMe | OMe | H | H | H | H | H | H | H | H | H | CR₃ | C | 68–70 |
| 6-68 | 6-Ph(4-Cl) | OMe | OMe | H | H | H | H | H | H | H | H | H | CR₃ | O | Gum |
| 6-69 | 6-Ph | OMe | OMe | H | H | H | H | H | H | H | H | H | CR₃ | C | 159–162 |
| 6-70 | 6-CHO | OMe | OMe | H | H | H | H | H | H | H | H | H | CR₃ | O | 123–125 |
| 6-71 | 6-CH=NOH | OMe | OMe | H | H | H | H | H | H | H | H | H | CR₃ | C | powder |
| 672 | 6-CH=NOMe | OMe | OMe | H | H | H | H | H | H | H | H | H | CR₃ | O | 1.5870 (25) |
| 6-73 | 6-CH=NOEt | OMe | OMe | H | H | H | H | H | H | H | H | H | CR₃ | O | 1.5729 (25) |
| 6-74 | 6-—CH=NOCH₂CH=CH₂ | OMe | OMe | H | H | H | H | H | H | H | H | H | CR₃ | O | 1.5656 (25) |
| 6-75 | 6CONEt₂ | OMe | OMe | H | H | H | H | H | H | H | H | H | CR₃ | C | Gum |
| 6-76 | 6-*4 | OMe | OMe | H | H | H | H | H | H | H | H | H | CR₃ | C | 63–65 |
| 6-77 | 6-CONPh₂ | OMe | OMe | H | H | H | H | H | H | H | H | H | CR₃ | O | 180–181 |
| 6-78 | 6-CN | OMe | OMe | H | H | H | H | H | H | H | H | H | CR₃ | C | 86–89 |
| 6-79 | 6-CH=CHCO₂Me | OMe | OMe | H | H | H | H | H | H | H | H | H | CR₃ | O | 137–139 |
| 6-80 | 6-COPh | OMe | OMe | H | H | H | H | H | H | H | H | H | CR₃ | O | 155–157 |
| 6-81 | 6-COMe | OMe | OMe | H | H | H | H | H | H | H | H | H | CR₃ | O | Gum |
| 6-82 | 6-CH=CHPh | OMe | OMe | H | H | H | H | H | H | H | H | H | CR₃ | O | 118–120 |
| 6-83 | 6-CH₂OH | OMe | OMe | H | H | H | H | H | H | H | H | H | CR₃ | O | 100–102 |
| 6-84 | 6-CH₂I | OMe | OMe | H | H | H | H | H | H | H | H | H | CR₃ | O | 95–98 |
| 6-85 | 6-CH₂-*3 | OMe | OMe | H | H | H | H | H | H | H | H | H | CR₃ | O | 90–92 |
| 6-86 | 6-CH=CHCN | OMe | OMe | H | H | H | H | H | H | H | H | H | CR₃ | O | Gum |
| 6-87 | 6-CH₂O—CH₂CH=CH₂Me | OMe | OMe | H | H | H | H | H | H | H | H | H | CR₃ | O | |
| 6-88 | 6-CH₂OMe | OMe | OMe | H | H | H | H | H | H | H | H | H | CR₃ | O | Gum |
| 6-89 | 6-CH₂Bn | OMe | OMe | H | H | H | H | H | H | H | H | H | CR₃ | O | Gum |
| 6-90 | 6-C(Me)=NOMe | OMe | OMe | H | H | H | H | H | H | H | H | H | CR₃ | O | Gum |
| 6-91 | 6-*5 | OMe | OMe | H | H | H | H | H | H | H | H | H | CR₃ | O | 118–120 |

TABLE 6-continued

| No. | Xn *1 | R₁ | R₂ | R₃ | y₁ | y₂ | y₃ | y₄ | y₅ | y₆ | y₇ | y₈ | A | Z | Physical Data *2 |
|---|---|---|---|---|---|---|---|---|---|---|---|---|---|---|---|
| 6-92 | 6-CH₂OCH₂C≡CH | OMe | OMe | H | H | H | H | H | H | H | H | H | CR₃ | O | Gum |
| 6-93 | 6-CH₂OCH₂Prᶜ | OMe | OMe | H | H | H | H | H | H | H | H | H | CR₃ | O | Gum |
| 6-94 | 6-CH(Cl)Et | OMe | OMe | H | H | H | H | H | H | H | H | H | CR₃ | O | Gum |
| 6-95 | 6-CH₂OCONHEt | OMe | OMe | H | H | H | H | H | H | H | H | H | CR₃ | O | 98–100 |
| 6-96 | 6-CH₂OCOPh | OMe | OMe | H | H | H | H | H | H | H | H | H | CR₃ | O | 107–110 |
| 6-97 | 6-Ph | OMe | OMe | H | H | H | H | H | H | H | H | H | CR₃ | O | 105–106 |
| 6-98 | 6-Ph | OMe | OMe | H | H | H | H | H | H | H | H | H | CR₃ | O | 1.5667 (26) |
| 6-99 | 6-COEt | OMe | OMe | H | H | H | H | H | H | H | H | H | CR₃ | O | Gum |
| 6-100 | 6-COCF₃ | OMe | OMe | H | H | H | H | H | H | H | H | H | CR₃ | O | Gum |
| 6-101 | 6-CH=NNMe₂ | OMe | OMe | H | H | H | H | H | H | H | H | H | CR₃ | O | 1.5438 (25) |
| 6-102 | 6-CH=NNHPh | OMe | OMe | H | H | H | H | H | H | H | H | H | CR₃ | O | 70–75 |
| 6-103 | 6-CH=NNHCOMe | OMe | OMe | H | H | H | H | H | H | H | H | H | CR₃ | O | 188–189 |
| 6-104 | 6-CH=NNHMe | OMe | OMe | H | H | H | H | H | H | H | H | H | CR₃ | O | 40 |
| 6-105 | 6-CH(F)Me) | OMe | OMe | H | H | H | H | H | H | H | H | H | CR₃ | O | 106–108 |
| 6-106 | 6-CF₂H | OMe | OMe | H | H | H | H | H | H | H | H | H | CR₃ | O | 125–128 |
| 6-107 | 6-thien-3-yl | OMe | OMe | H | H | H | H | H | H | H | H | H | CR₃ | O | 133–135 |
| 6-108 | 6-furan-2-yl | OMe | OMe | H | H | H | H | H | H | H | H | H | CR₃ | O | 141–143 |
| 6-109 | 6-thienyl | OMe | OMe | H | H | H | H | H | H | H | H | H | CR₃ | O | 149–151 |
| 6-110 | 6-oxazol-2-yl | OMe | OMe | H | H | H | H | H | H | H | H | H | CR₃ | O | 162–163 |
| 6-111 | 6-furyl | OMe | OMe | H | H | H | H | H | H | H | H | H | CR₃ | O | 121–123 |
| 6-112 | 6-thiazol--2-yl | OMe | OMe | H | H | H | H | H | H | H | H | H | CR₃ | O | 138–140 |
| 6-113 | 6-(3-Me--thienyl) | OMe | OMe | H | H | H | H | H | H | H | H | H | CR₃ | O | 66–68 |
| 6-114 | 6-(5-Me--thienyl) | OMe | OMe | H | H | H | H | H | H | H | H | H | CR₃ | O | 118–120 |
| 6-115 | 6-(3,5-Me₂--pyrazol-1-yl) | OMe | OMe | H | H | H | H | H | H | H | H | H | CR₃ | O | 112–114 |
| 6-116 | 6-(1-Me--pyrrol-2-yl) | OMe | OMe | H | H | H | H | H | H | H | H | H | CR₃ | O | 75–77 |
| 6-117 | 6-(4-CO₂Me--pyrrol-3-yl) | OMe | OMe | H | H | H | H | H | H | H | H | H | CR₃ | O | 182–184 |
| 6-118 | 6-imidazol--1-yl | OMe | OMe | H | H | H | H | H | H | H | H | H | CR₃ | O | 131–133 |
| 6-119 | 6-benzo--triazol-1-yl | OMe | OMe | H | H | H | H | H | H | H | H | H | CR₃ | O | 178–180 |
| 6-120 | 6-(2-Me--dioxolan-2-yl | OMe | OMe | H | H | H | H | H | H | H | H | H | CR₃ | O | Gum |

*1 H represents that all of Xn are hydrogen. If any position is specially indicated, other positions are bonded with hydrogen. (The same can be applied for Tables 2 onward.)
*2 Physical data represent either a melting point or a refractive index.
*3

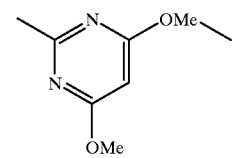

*4

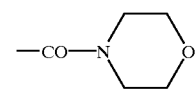

*3

TABLE 6-continued

[Structure: bicyclic tetrahydrobenzoxazole (with positions y1-y8) attached at position 1 of phenyl ring; phenyl has Xn substituents at positions 5,6 and position 3,4; position 2 connected via Z to a pyrimidine/triazine ring bearing R1, R2, with A in the ring]

| No. | Xn *1 | R₁ | R₂ | R₃ | y₁ | y₂ | y₃ | y₄ | y₅ | y₆ | y₇ | y₈ | A | Z | Physical Data *2 |
|---|---|---|---|---|---|---|---|---|---|---|---|---|---|---|---|

*5:
- pyrimidine with OMe, OMe substituents (2,4-dimethoxypyrimidin-6-yl via methyl linkage)
- pyridine with CF₃ and Cl substituents

TABLE 7

[Structure: cyclopentane-fused oxazole (with y1-y6) attached at position 1 of phenyl ring; phenyl has Xn; position 2 connected via Z to pyrimidine bearing R1, R2, A]

| No. | Xn | R₁ | R₂ | R₃ | y₁ | y₂ | y₃ | y₄ | y₅ | y₆ | A | Z | Physical Data |
|---|---|---|---|---|---|---|---|---|---|---|---|---|---|
| 7-1 | H | OMe | OMe | H | H | H | H | H | H | H | CR₃ | O | |
| 7-2 | 6-Cl | OMe | OMe | H | H | H | H | H | H | H | CR₃ | O | 143 |
| 7-3 | 6-Cl | OMe | OMe | H | Me | H | H | H | H | H | CR₃ | O | |
| 7-4 | 6-Cl | OMe | OMe | H | H | H | Me | H | H | H | CR₃ | O | |
| 7-5 | 6-Cl | OMe | OMe | H | H | H | H | H | Me | H | CR₃ | O | |
| 7-6 | 6-Cl | OMe | OMe | | H | H | H | H | H | H | N | O | |
| 7-7 | 6-Cl | OMe | OMe | H | Me | Me | H | H | H | H | CR₃ | O | |
| 7-8 | 6-Cl | OMe | OMe | H | H | H | Me | Me | H | H | CR₃ | O | |
| 7-9 | 6-Cl | OMe | OMe | H | H | H | H | H | Me | Me | CR₃ | O | |
| 7-10 | 6-Cl | OMe | OMe | | H | H | H | H | H | H | N | S | |
| 7-11 | 6-Cl | OMe | OMe | H | Et | H | H | H | H | H | CR₃ | O | |
| 7-12 | 6-Cl | OMe | OMe | H | H | H | Et | H | H | H | CR₃ | O | |
| 7-13 | 6-Cl | OMe | OMe | H | H | H | H | H | Et | H | CR₃ | O | |
| 7-14 | 6-Cl | OMe | OMe | H | n-Pr | H | H | H | H | H | CR₃ | O | |
| 7-15 | 6-Cl | OMe | OMe | H | i-Pr | H | H | H | H | H | CR₃ | O | |
| 7-16 | 6-Cl | OMe | OMe | H | H | H | i-Pr | H | H | H | CR₃ | O | |
| 7-17 | 6-Cl | OMe | OMe | H | H | H | H | H | i-Pr | H | CR₃ | O | |
| 7-18 | 6-Cl | OMe | OMe | H | =O | | H | H | H | H | CR₃ | O | |

TABLE 7-continued

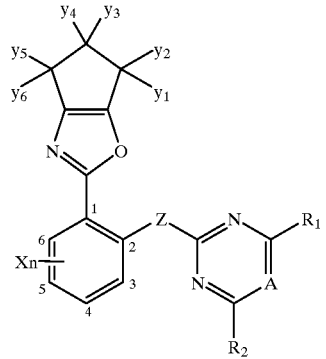

| No. | Xn | R₁ | R₂ | R₃ | y₁ | y₂ | y₃ | y₄ | y₅ | y₆ | A | Z | Physical Data |
|---|---|---|---|---|---|---|---|---|---|---|---|---|---|
| 7-19 | 6-Cl | OMe | OMe | H | H | H | =O | | H | H | CR₃ | O | |
| 7-20 | 6-Cl | OMe | OMe | H | H | H | H | H | =O | | CR₃ | O | |
| 7-21 | 6-Cl | OMe | OMe | H | H | H | H | H | H | H | CR₃ | S | |
| 7-22 | 6-Cl | OMe | OMe | H | =O | | H | H | Me | H | CR₃ | O | |
| 7-23 | 6-Cl | OMe | OMe | H | H | H | =O | | H | H | CR₃ | O | |
| 7-24 | 6-Cl | OMe | OMe | H | H | H | H | H | =O | | CR₃ | S | |
| 7-25 | 6-Cl | OMe | OMe | H | =O | | H | H | Me | Me | CR₃ | O | |
| 7-26 | 6-Cl | OMe | OMe | H | =O | | H | H | Me | Me | CR₃ | S | |
| 7-27 | 6-F | OMe | OMe | H | H | H | H | H | H | H | CR₃ | O | |
| 7-28 | 6-F | OMe | OMe | H | Me | H | H | H | H | H | CR₃ | O | |
| 7-29 | 6-F | OMe | OMe | H | H | H | Me | H | H | H | CR₃ | O | |
| 7-30 | 6-F | OMe | OMe | H | H | H | H | H | Me | H | CR₃ | O | |
| 7-31 | 6-F | OMe | OMe | H | H | H | H | H | H | H | CR₃ | S | |
| 7-32 | 6-Br | OMe | OMe | H | H | H | H | H | H | H | CR₃ | O | |
| 7-33 | 6-I | OMe | OMe | H | H | H | H | H | H | H | CR₃ | O | |
| 7-34 | 6-OPh | OMe | OMe | H | H | H | H | H | H | H | CR₃ | O | |
| 7-35 | 6-Ph | OMe | OMe | H | H | H | H | H | H | H | CR₃ | O | |
| 7-36 | 6-COOMe | OMe | OMe | H | H | H | H | H | H | H | CR₃ | O | |
| 7-37 | 6-OMe | OMe | OMe | H | H | H | H | H | H | H | CR₃ | O | |
| 7-38 | 6-Me | OMe | OMe | H | H | H | H | H | H | H | CR₃ | O | |
| 7-39 | 6-C(=NOMe)Me | OMe | OMe | H | H | H | H | H | H | H | CR₃ | O | |
| 7-40 | 6-CH=CH₂ | OMe | OMe | H | H | H | H | H | H | H | CR₃ | O | |
| 7-41 | 6-OBn | OMe | OMe | H | H | H | H | H | H | H | CR₃ | O | |
| 7-42 | 6-O-c-C₅H₉ | OMe | OMe | H | H | H | H | H | H | H | CR₃ | O | |
| 7-43 | 6-OCH₂CH=CHCl | OMe | OMe | H | H | H | H | H | H | H | CR₃ | O | |
| 7-44 | 6-OH | OMe | OMe | H | H | H | H | H | H | H | CR₃ | O | |
| 7-45 | 6-OSO₂CF₃ | OMe | OMe | H | H | H | H | H | H | H | CR₃ | O | |
| 7-46 | 6-OPh(2-Me) | OMe | OMe | H | H | H | H | H | H | H | CR₃ | O | |
| 7-47 | 6-Cl | OMe | OMe | H | H | H | H | H | H | H | CR₃ | O | |

TABLE 8

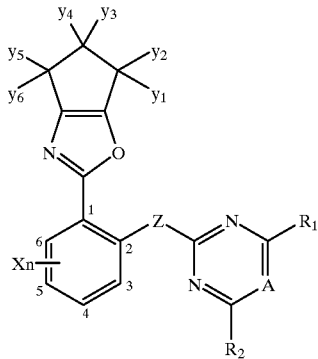

| No. | Xn | R₁ | R₂ | R₃ | y₁ | y₂ | y₃ | y₄ | y₅ | y₆ | A | Z | Physical Data |
|---|---|---|---|---|---|---|---|---|---|---|---|---|---|
| 8-1 | H | OMe | OMe | H | H | H | H | H | H | H | CR₃ | O | |
| 8-2 | H | OMe | OMe | H | H | H | H | H | H | H | CR₃ | O | |
| 8-3 | H | OMe | OMe | H | Me | H | H | H | H | H | CR₃ | O | |
| 8-4 | H | OMe | OMe | H | H | H | Me | H | H | H | CR₃ | O | |

TABLE 8-continued

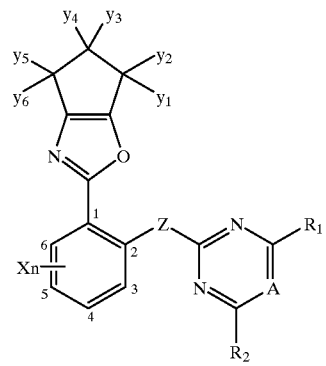

| No. | Xn | $R_1$ | $R_2$ | $R_3$ | $y_1$ | $y_2$ | $y_3$ | $y_4$ | $y_5$ | $y_6$ | A | Z | Physical Data |
|---|---|---|---|---|---|---|---|---|---|---|---|---|---|
| 8-5 | H | OMe | OMe | H | H | H | H | H | Me | H | $CR_3$ | O | |
| 8-6 | H | OMe | OMe | H | H | H | H | H | H | H | $CR_3$ | S | |
| 8-7 | H | OMe | OMe | H | Me | Me | H | H | H | H | $CR_3$ | O | |
| 8-8 | H | OMe | OMe | H | H | H | Me | Me | H | H | $CR_3$ | O | |
| 8-9 | H | OMe | OMe | H | H | H | H | H | Me | Me | $CR_3$ | O | |
| 8-10 | H | OMe | OMe | | H | H | H | H | H | H | N | O | |
| 8-11 | H | OMe | OMe | H | Et | H | H | H | H | H | $CR_3$ | O | |
| 8-12 | H | OMe | OMe | H | H | H | Et | H | H | H | $CR_3$ | O | |
| 8-13 | H | OMe | OMe | H | H | H | H | H | Et | H | $CR_3$ | O | |
| 8-14 | H | OMe | OMe | | H | H | H | H | H | H | N | S | |
| 8-15 | H | OMe | OMe | H | i-Pr | H | H | H | H | H | $CR_3$ | O | |
| 8-16 | H | OMe | OMe | H | H | H | i-Pr | H | H | H | $CR_3$ | O | |
| 8-17 | H | OMe | OMe | H | H | H | H | H | i-Pr | H | $CR_3$ | O | |
| 8-18 | H | OMe | OMe | H | =O | | H | H | H | H | $CR_3$ | O | |
| 8-19 | H | OMe | OMe | H | H | H | =O | | H | H | $CR_3$ | O | |
| 8-20 | H | OMe | OMe | H | H | H | H | H | =O | | $CR_3$ | O | |
| 8-21 | H | OMe | OMe | H | H | H | H | H | H | H | $CR_3$ | O | |
| 8-22 | H | OMe | OMe | H | =O | | H | H | Me | H | $CR_3$ | O | |
| 8-23 | H | OMe | OMe | H | H | H | =O | | H | H | $CR_3$ | S | |
| 8-24 | H | OMe | OMe | H | H | H | H | H | =O | | $CR_3$ | S | |
| 8-25 | H | OMe | OMe | H | =O | | H | H | Me | Me | $CR_3$ | O | |
| 8-26 | H | OMe | OMe | H | =O | | H | H | Me | Me | $CR_3$ | S | |
| 8-27 | 5-$NMe_2$ | OMe | OMe | H | H | H | H | H | H | H | $CR_3$ | O | |
| 8-28 | 5-$NMe_2$ | OMe | OMe | H | Me | H | H | H | H | H | $CR_3$ | O | |
| 8-29 | 5-$NMe_2$ | OMe | OMe | H | H | H | Me | H | H | H | $CR_3$ | O | |
| 8-30 | 5-$NMe_2$ | OMe | OMe | H | H | H | H | H | Me | H | $CR_3$ | O | |
| 8-31 | 5-$NMe_2$ | OMe | OMe | H | H | H | H | H | H | H | $CR_3$ | | S |
| 8-32 | 5-$NH_2$ | OMe | OMe | H | H | H | H | H | H | H | $CR_3$ | O | |
| 8-33 | 5-*1 | OMe | OMe | H | H | H | H | H | H | H | $CR_3$ | O | |
| 8-34 | 5-Br | OMe | OMe | H | H | H | H | H | H | H | $CR_3$ | O | |
| 8-35 | 5-Cl | OMe | OMe | H | H | H | H | H | H | H | $CR_3$ | O | |
| 8-36 | 5-COOMe | OMe | OMe | H | H | H | H | H | H | H | $CR_3$ | O | |
| 8-37 | 5-OMe | OMe | OMe | H | H | H | H | H | H | H | $CR_3$ | O | |
| 8-38 | 5-Me | OMe | OMe | H | H | H | H | H | H | H | $CR_3$ | O | |
| 8-39 | 5-CN | OMe | OMe | H | H | H | H | H | H | H | $CR_3$ | O | |
| 8-40 | 5-Ph | OMe | OMe | H | H | H | H | H | H | H | $CR_3$ | O | |
| 8-41 | 5-$CH_2$SMe | OMe | OMe | H | H | H | H | H | H | H | $CR_3$ | O | |
| 8-42 | 5-SMe | OMe | OMe | H | H | H | H | H | H | H | $CR_3$ | | O |
| 8-43 | 5-SEt | OMe | OMe | H | H | H | H | H | H | H | $CR_3$ | O | |
| 8-44 | 5-OAc | OMe | OMe | H | H | H | H | H | H | H | $CR_3$ | O | |
| 8-45 | 5-$OSO_2CF_3$ | OMe | OMe | H | H | H | H | H | H | H | $CR_3$ | O | |
| 8-46 | 5-NHMe | OMe | OMe | H | H | H | H | H | H | H | $CR_3$ | | O |
| 8-47 | 5-NHBn | OMe | OMe | H | H | H | H | H | H | H | $CR_3$ | O | |

*1

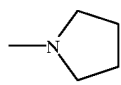

TABLE 9

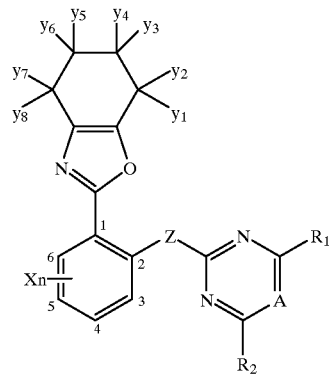

| No. | Xn | R₁ | R₂ | R₃ | y₁ | y₂ | y₃ | y₄ | y₅ | y₆ | y₇ | y₈ | A | Z | Physical Data |
|---|---|---|---|---|---|---|---|---|---|---|---|---|---|---|---|
| 9-1 | H | OMe | OMe | H | H | H | H | H | H | H | H | H | CR₃ | O | 107–108 |
| 9-2 | H | OMe | OMe | H | H | H | H | H | H | H | H | H | CR₃ | S | |
| 9-3 | H | OMe | OMe | H | Me | H | H | H | H | H | H | H | CR₃ | O | |
| 9-4 | H | OMe | OMe | H | H | H | Me | H | H | H | H | H | CR₃ | O | |
| 9-5 | H | OMe | OMe | H | H | H | H | H | Me | H | H | H | CR₃ | O | |
| 9-6 | H | OMe | OMe | H | H | H | H | H | H | H | Me | H | CR₃ | O | |
| 9-7 | H | OMe | OMe | H | Me | Me | H | H | H | H | H | H | CR₃ | O | |
| 9-8 | H | OMe | OMe | H | H | H | Me | Me | H | H | H | H | CR₃ | O | |
| 9-9 | H | OMe | OMe | H | H | H | H | H | Me | Me | H | H | CR₃ | O | |
| 9-10 | H | OMe | OMe | H | H | H | H | H | H | Me | Me | H | CR₃ | O | |
| 9-11 | H | OMe | OMe | H | Et | H | H | H | H | H | H | H | CR₃ | O | |
| 9-12 | H | OMe | OMe | H | H | H | Et | H | H | H | H | H | CR₃ | O | |
| 9-13 | H | OMe | OMe | H | H | H | H | H | Et | H | H | H | CR₃ | O | |
| 9-14 | H | OMe | OMe | H | H | H | H | H | H | H | Et | H | CR₃ | O | |
| 9-15 | H | OMe | OMe | H | i-Pr | H | H | H | H | H | H | H | CR₃ | O | |
| 9-16 | H | OMe | OMe | H | H | H | i-Pr | H | H | H | H | H | CR₃ | O | |
| 9-17 | H | OMe | OMe | H | H | H | H | H | i-Pr | H | H | H | CR₃ | O | |
| 9-18 | H | OMe | OMe | H | | =O | H | H | H | H | H | H | CR₃ | O | |
| 9-18 | H | OMe | OMe | H | | =O | H | H | H | H | H | H | CR₃ | O | |
| 9-19 | H | OMe | OMe | H | H | H | | =O | H | H | H | H | CR₃ | O | |
| 9-20 | H | OMe | OMe | H | H | H | H | H | | =O | H | H | CR₃ | O | |
| 9-21 | H | OMe | OMe | H | H | H | H | H | H | H | | =O | CR₃ | O | |
| 9-22 | H | OMe | OMe | H | | =O | H | H | Me | H | H | H | CR₃ | O | |
| 9-23 | H | OMe | OMe | H | H | H | | =O | H | H | H | H | CR₃ | S | |
| 9-24 | H | OMe | OMe | H | H | H | H | H | | =O | H | H | CR₃ | S | |
| 9-25 | H | OMe | OMe | H | | =O | H | H | Me | Me | H | H | CR₃ | O | |
| 9-26 | H | OMe | OMe | H | | =O | H | H | Me | Me | Me | H | CR₃ | O | |
| 9-27 | 5-NMe₂ | OMe | OMe | H | H | H | H | H | H | H | H | H | CR₃ | O | 125–129 |
| 9-28 | 5-NMe₂ | OMe | OMe | H | Me | H | H | H | H | H | H | H | CR₃ | O | |
| 9-29 | 5-NMe₂ | OMe | OMe | H | H | H | Me | H | H | H | H | H | CR₃ | O | |
| 9-30 | 5-NMe₂ | OMe | OMe | H | H | H | H | H | Me | H | H | H | CR₃ | O | |
| 9-31 | 5-NMe₂ | OMe | OMe | H | H | H | H | H | H | H | Me | H | CR₃ | O | |
| 9-32 | 5-NH₂ | OMe | OMe | H | H | H | H | H | H | Me | H | H | CR₃ | O | |
| 9-33 | 5-*1 | OMe | OMe | H | H | H | H | H | H | H | H | H | CR₃ | O | |
| 9-34 | 5-Br | OMe | OMe | H | H | H | H | H | H | H | H | H | CR₃ | O | |
| 9-35 | 5-Cl | OMe | OMe | H | H | H | H | H | H | H | H | H | CR₃ | O | 131–132.5 |
| 9-36 | 5-COOMe | OMe | OMe | H | H | H | H | H | H | H | H | H | CR₃ | O | |
| 9-37 | 5-OMe | OMe | OMe | H | H | H | H | H | H | H | H | H | CR₃ | O | |
| 9-38 | 5-Me | OMe | OMe | H | H | H | H | H | H | H | H | H | CR₃ | O | |
| 9-39 | 5-CN | OMe | OMe | H | H | H | H | H | H | H | H | H | CR₃ | O | |
| 9-40 | 5-Ph | OMe | OMe | H | H | H | H | H | H | H | H | H | CR₃ | O | |
| 9-41 | 5-CH₂SMe | OMe | OMe | H | H | H | H | H | H | H | H | H | CR₃ | O | |
| 9-42 | 5-SMe | OMe | OMe | H | H | H | H | H | H | H | H | H | CR₃ | O | |
| 9-43 | 5-SEt | OMe | OMe | H | H | H | H | H | H | H | H | H | CR₃ | O | |
| 9-44 | 5-OAc | OMe | OMe | H | H | H | H | H | H | H | H | H | CR₃ | O | |
| 9-45 | 5-OSO₂CF₃ | OMe | OMe | H | H | H | H | H | H | H | H | H | CR₃ | O | |
| 9-46 | 5-NHMe | OMe | OMe | H | H | H | H | H | H | H | H | H | CR₃ | O | |
| 9-47 | 5-NHBn | OMe | OMe | H | H | H | H | H | H | H | H | H | CR₃ | O | |
| 9-48 | 5-NEt₂ | OMe | OMe | H | H | H | H | H | H | H | H | H | CR₃ | O | Gum |
| 9-49 | 5-*2 | OMe | OMe | H | H | H | H | H | H | H | H | H | CR₃ | O | Gum |

*1

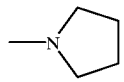

TABLE 9-continued

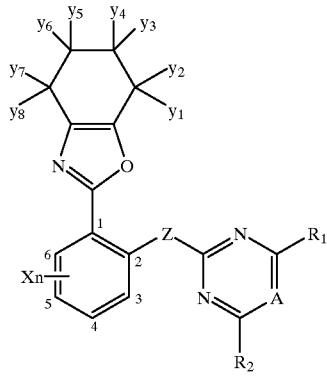

| No. | Xn | R₁ | R₂ | R₃ | y₁ | y₂ | y₃ | y₄ | y₅ | y₆ | y₇ | y₈ | A | Z | Physical Data |
|---|---|---|---|---|---|---|---|---|---|---|---|---|---|---|---|
| *2 | —N⟨morpholino⟩ | | | | | | | | | | | | | | |

TABLE 10

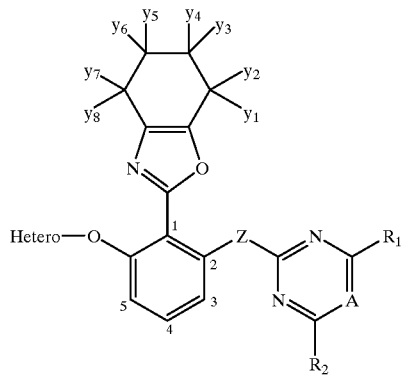

| No. | Hetero | R₁ | R₂ | R₃ | y₁ | y₂ | y₃ | y₄ | y₅ | y₆ | y₇ | y₈ | A | Z | Physical Data |
|---|---|---|---|---|---|---|---|---|---|---|---|---|---|---|---|
| 10-1 | 4,6-dimethoxy-2-pyrimidyl | OMe | OMe | H | H | H | H | H | H | H | H | H | CR₃ | O | 1.540 (27° C.) |
| 10-2 | 4,6-dimethoxy-2-triazyl | OMe | OMe | H | H | H | H | H | H | H | H | H | CR₃ | O | |
| 10-3 | 4,6-dimethoxy-2-pyrimidyl | OMe | OMe | H | Me | H | H | H | H | H | H | H | CR₃ | O | |
| 10-4 | 4,6-dimethoxy-2-pyrimidyl | OMe | OMe | H | H | H | Me | H | H | H | H | H | CR₃ | O | 115–116 |
| 10-5 | 4,6-dimethoxy-2-pyrimidyl | OMe | OMe | H | H | H | H | Me | H | H | H | H | CR₃ | O | |
| 10-6 | 4,6-dimethoxy-2-pyrimidyl | OMe | OMe | H | H | H | H | H | H | Me | H | H | CR₃ | O | |
| 10-7 | 4,6-dimethoxy-2-pyrimidyl | OMe | OMe | H | Me | Me | H | H | H | H | H | H | CR₃ | O | |
| 10-8 | 4,6-dimethoxy-2-pyrimidyl | OMe | OMe | H | H | H | Me | Me | H | H | H | H | CR₃ | O | |
| 10-9 | 4,6-dimethoxy-2-pyrimidyl | OMe | OMe | H | H | H | H | H | Me | Me | H | H | CR₃ | O | |
| 10-10 | 4,6-dimethoxy-2-pyrimidyl | OMe | OMe | H | H | H | H | H | H | Me | Me | H | CR₃ | O | |
| 10-11 | 4,6-dimethoxy-2-pyrimidyl | OMe | OMe | H | Et | H | H | H | H | H | H | H | CR₃ | O | |
| 10-12 | 4,6-dimethoxy-2-pyrimidyl | OMe | OMe | H | H | H | Et | H | H | H | H | H | CR₃ | O | |
| 10-13 | 4,6-dimethoxy-2-pyrimidyl | OMe | OMe | H | H | H | H | H | Et | H | H | H | CR₃ | O | |

TABLE 10-continued

| No. | Hetero | R₁ | R₂ | R₃ | y₁ | y₂ | y₃ | y₄ | y₅ | y₆ | y₇ | y₈ | A | Z | Physical Data |
|---|---|---|---|---|---|---|---|---|---|---|---|---|---|---|---|
| 10-14 | 4,6-dimethoxy-2-pyrimidyl | OMe | OMe | H | H | H | H | H | H | H | Et | H | CR₃ | O | |
| 10-15 | 4,6-dimethoxy-2-pyrimidyl | OMe | OMe | H | i-Pr | H | H | H | H | H | H | H | CR₃ | O | |
| 10-16 | 4,6-dimethoxy-2-pyrimidyl | OMe | OMe | H | H | H | i-Pr | H | H | H | H | H | CR₃ | O | |
| 10-17 | 4,6-dimethoxy-2-pyrimidyl | OMe | OMe | H | H | H | H | H | i-Pr | H | H | H | CR₃ | O | |
| 10-18 | 4,6-dimethoxy-2-pyrimidyl | OMe | OMe | H | =O | H | H | H | H | H | H | H | CR₃ | O | |
| 10-19 | 4,6-dimethoxy-2-pyrimidyl | OMe | OMe | H | H | H | =O | H | H | H | H | H | CR₃ | O | |
| 10-20 | 4,6-dimethoxy-2-pyrimidyl | OMe | OMe | H | H | H | H | H | =O | H | H | H | CR₃ | O | |
| 10-21 | 4,6-dimethoxy-2-pyrimidyl | OMe | OMe | H | H | H | H | H | H | H | =O | H | CR₃ | O | |
| 10-22 | 4,6-dimethoxy-2-pyrimidyl | OMe | OMe | H | =O | H | H | Me | H | H | H | H | CR₃ | O | |
| 10-23 | 4,6-dimethoxy-2-pyrimidyl | OMe | OMe | H | H | H | =O | H | H | H | H | H | CR₃ | S | |
| 10-24 | 4,6-dimethoxy-2-pyrimidyl | OMe | OMe | H | H | H | H | H | =O | H | H | H | CR₃ | S | |
| 10-25 | 4,6-dimethoxy-2-pyrimidyl | OMe | OMe | H | =O | H | H | Me | Me | H | H | H | CR₃ | O | |
| 10-26 | 4,6-dimethoxy-2-pyrimidyl | OMe | OMe | H | =O | H | H | Me | Me | Me | H | H | CR₃ | O | |
| 10-27 | 2-pyridyl | OMe | OMe | H | H | H | H | H | H | H | H | H | CR₃ | O | |
| 10-28 | 4,6-dimethoxy-2-triazyl | OMe | OMe | H | Me | H | H | H | H | H | H | H | CR₃ | O | |
| 10-29 | 4,6-dimethoxy-2-triazyl | OMe | OMe | H | H | H | Me | H | H | H | H | H | CR₃ | O | |
| 10-30 | 4,6-dimethoxy-2-triazyl | OMe | OMe | H | H | H | H | H | Me | H | H | H | CR₃ | O | |
| 10-31 | 4,6-dimethoxy-2-triazyl | OMe | OMe | H | H | H | H | H | H | H | Me | H | CR₃ | O | |
| 10-32 | 2-pyridyl | OMe | OMe | H | H | H | H | H | H | H | Me | H | CR₃ | O | |
| 10-33 | 3-pyridyl | OMe | OMe | H | H | H | H | H | H | H | H | H | CR₃ | O | |
| 10-34 | 3,5-dichloro-2-pyridyl | OMe | OMe | H | H | H | H | H | H | H | H | H | CR₃ | O | |
| 10-35 | 3-chloro-5-trifluoromethyl-2-pyridyl | OMe | OMe | H | H | H | H | H | H | H | H | H | CR₃ | O | |
| 10-36 | 2-pyrimidyl | OMe | OMe | H | H | H | H | H | H | H | H | H | CR₃ | O | |
| 10-37 | 4,6-dimethyl-2-pyrimidyl | OMe | OMe | H | H | H | H | H | H | H | H | H | CR₃ | O | |
| 10-38 | 4-chloro-6-methyl-2-pyrimidyl | OMe | OMe | H | H | H | H | H | H | H | H | H | CR₃ | O | |
| 10-39 | 4-methoxy-6-methyl-2-pyrimidyl | OMe | OMe | H | H | H | H | H | H | H | H | H | CR₃ | O | |
| 10-40 | 4-pyridyl | OMe | OMe | H | H | H | H | H | H | H | H | H | CR₃ | O | |
| 10-41 | 6-chloro-2-pyridyl | OMe | OMe | H | H | H | H | H | H | H | H | H | CR₃ | O | |
| 10-42 | 6-trifluoromethyl-2-pyridyl | OMe | OMe | H | H | H | H | H | H | H | H | H | CR₃ | O | |

| Compound No. | ¹H-NMR data (δ value by TMS standard) |
|---|---|
| 1-11 | 2.08 (s, 3H), 3.79 (s, 12H), 5.70 (s, 2H), 6.59 (s, 1H), 7.19–7.30 (m, 2H), 7.45–7.55 (m, 1H) |
| 1-12 | 3.30 (s, 3H), 3.80 (s, 6H), 4.40 (s, 2H), 5.70 (s, 1H), 7.10 (d, 1H), 7.20–7.28 (m, 1H), 7.38–7.49 (m, 2H) |
| 1-13 | 3.11 (s, 3H), 3.78 (s, 12H), 4.20 (d, 2H), 5.68 (s, 1H), 6.89 (s, 1H), 7.24 (d, 2H), 7.53 (t, 1H) |
| 1-17 | 1.10–1.19 (m, 6H), 3.55–3.68 (m, 1H), 3.79 (s, 6H), 4.45 (s, 2H), 5.71 (s, 1H), 7.09 (d, 1H), 7.19–7.28 (m, 1H), 7.38–7.48 (m, 2H) |
| 1-19 | 1.13 (d, 6H), 1.28 (d, 6H), 3.47–3.70 (m, 1H), 3.79 (s, 6H), 4.42 (s, 2H), 4.47–5.59 (m, 1H), 5.68 (s, 1H), 6.89 (d, 2H), 7.00 (d, 1H), 7.39 (t, 1H) |
| 1-20 | 1.07 (d, 6H), 3.39–3.52 (m, 1H), 3.79 (d, 12H), 4.23 (s, 2H), 5.68 (s, 2H), 6.88 (d, 1H), 7.23 (d, 2H), 7.52 (t, 1H) |
| 1-24 | 2.01 (s, 3H), 3.62 (s, 2H), 3.79 (s, 6H), 5.70 (s, 1H), 6.98 (s, 1H), 7.18–7.27 (m, 1H), 7.38–7.49 (m, 2H) |
| 1-25 | 3.36 (s, 3H), 3.45–3.56 (m, 4H), 3.79 (s, 6H), 4.52 (s, 2H), 5.70 (s, 1H), 7.10 (s, 1H), 7.18–7.27 (m, 1H), 7.36–7.49 (m, 2H) |
| 1-35 | 2.27 (s, 3H), 3.78 (s, 6H), 3.81 (s, 3H), 5.70 (s, 1H), 6.80–7.49 (m, 12H) |
| 1-49 | 2.11 (s, 3H), 3.73 (s, 6H), 5.18 (s, 2H), 5.71 (s, 1H), 7.25–7.51 (m, 8H) |
| 1-52 | 2.82 (s, 6H), 3.90 (s 6H), 5.55 (s, 2H), 5.75 (s, 1H), 7.26–7.59 (m, 8H) |
| 1-54 | 1.17 (t, 3H), 3.26 (q, 2H), 3.75 (s, 6H), 4.75–4.85 (m, 1H), 5.18 (s, 2H), 7.23–7.55 (m, 8H) |
| 1-55 | 3.71 (s, 6H), 4.12 (s, 2H), 5.30 (s, 2H), 5.72 (s, 1H), 7.25–7.56 (m, 8H) |
| 1-57 | 3.20 (s, 3H), 5.69 (s, 2H), 5.75 (s, 1H), 7.40–7.53 (m, 6H), 7.55 (d, 2H) |
| 3-82 | 2.01 (s, 3H), 2.34 (s, 3H), 3.79 (s, 6H), 5.70 (s, 1H), 7.18 (dd, 1H), 7.38–7.39 (m, 2H) |
| 3-119 | 2.16 (s, 3H), 3.72 (s, 6H), 5.71 (s, 1H), 7.22 (dd, 1H), 7.39 (d, 2H), 7.43 (d, 1H), 7.45 (d, 1H), 7.80 (d, 2H) |
| 3-174 | 2.00 (s, 3H), 3.82 (s, 6H), 5.72 (s, 1H), 6.75 (s, 1H), 7.00–7.60 (m, 7H) |
| 3-176 | 1.25 (t, 3H), 2.75 (q, 2H), 3.80 (s, 6H), 5.71 (s, 1H), 6.85 (s, 1H), 7.10–7.60 (m, 8H) |
| 3-195 | 1.35 (t, 3H), 3.10 (c, 2H), 3.8 (s, 6H), 5.76 (s, 1H), 7.03–7.11 (m, 2H), 7.32 (dd, 1H) 7.40 (d, 1H) |
| 3-197 | 1.90 (s, 3H), 2.09 (s, 6H), 3.78 (s, 6H), 5.70 (s, 1H), 6.00 (s, 1H), 7.18 (t, 1H), 7.39 (d, 2H) |
| 3-198 | 0.91 (d, 6H), 2.07 (s, 3H), 2.55 (d, 2H), 5.70 (s, 1H), 7.18 (t, 1H), 7.37–7.40 (m, 2H) |
| 3-202 | 3.78 (s, 6H), 3.92 (s, 6H), 5.72 (s, 1H), 6.88 (d, 1H), 7.2–7.4 (m, 5H), 7.50 (s, 1H) |
| 3-203 | 2.12 (s, 3H), 3.82 (s, 6H), 5.72 (s, 1H), 6.66 (s, 1H), 7.15–7.50 (m, 8H) |
| 3-205 | 3.00 (s, 6H), 3.75 (s, 6H), 5.72 (s, 1H), 6.68 (d, 2H), 7.18–7.43 (m, 4H), 7.74 (d, 2H) |
| 3-210 | 3.76 (s, 6H), 3.88 (s, 6H), 5.40 (s, 2H), 5.68 (s, 1H), 5.72 (s, 1H), 7.17 (q, 1H), 7.25 (d, 1H), 7.38 (m, 2H) |
| 3-219 | 3.72 (s, 6H), 3.90 (bs, 2H), 5.70 (s, 1H), 6.62 (d, 2H), 7.19 (d, 1H), 7.33 (t, 1H), 7.42 (d, 1H), 7.43 (s, 1H), 7.67 (d, 2H) |
| 6-8 | 0.95 (s, 6H), 1.08 (m, 1H), 1.50 (t, 2H), 2.29 (m, 2H), 2.50 (m, 2H), 3.80 (s, 6H), 5.68 (s, 1H), 7.18–7.40 (m, 3H) |
| 6-35 | 1.70 (m, 4H), 2.35 (m, 4H), 3.80 (s, 6H), 5.70 (s, 1H), 7.15–7.38 (m, 7H), 7.50 (t, 1H) |
| 6-40 | 1.75–190 (m, 4H), 2.45–2.55 (m, 1H), 3.80 (s, 6H), 5.33 (d, 1H), 5.70 (s, 1H), 5.78 (d, 1H), 7.06 (dd, 1H), 7.20 (d, 1H), 7.42 (t, 1H), 7.56 (d, 1H) |
| 6-54 | 0.95 (s, 9H), 1.26–1.60 (m, 3H), 1.90–2.80 (m, 4H), 3.80 (s, 6H), 5.80 (s, 4H), 7.19–7.45 (m, 3H) |
| 6-58 | 1.14 (t, 3H), 1.70–1.85 (m, 4H), 2.44–2.56 (m, 4H), 3.76 (s, 6H), 4.20 (q, 2H), 5.70 (s, 1H), 7.43 (d, 1H), 7.54 (t, 1H), 7.77 (d, 1H) |
| 6-59 | 1.70–1.85 (m, 4H), 2.44–2.56 (m, 4H), 3.78 (s, 9H), 5.70 (s, 1H), 7.43 (d, 1H), 7.53 (t, 1H), 7.73 (d, 1H) |
| 6-66 | 1.70–1.85 (m, 4H), 2.43–2.56 (m, 5H), 3.78 (s, 6H), 4.78 (d, 2H), 5.71 (s, 1H), 7.46 (d, 1H), 7.55 (t, 1H), 7.78 (d, 1H) |
| 6-68 | 1.70 (m, 4H), 2.35 (m, 4H), 3.82 (s, 6H), 5.72 (s, 1H), 7.13 (d, 2H), 7.30 (m, 4H), 7.50 (t, 1H) |
| 6-71 | 1.80 (m, 4H), 2.50 (m, 4H), 3.80 (s, 6H), 5.71 (s, 1H), 7.25–7.36 (m, 1H), 7.46 (t, 1H), 7.80 (m, 1H), 8.58 (s, 2H) |
| 6-75 | 1.04 (t, 3H), 1.25 (t, 3H), 1.71–1.89 (m, 4H), 2.42-2.55 (m, 4H), 3.10–3.30 (m, 4H), 3.85 (s, 6H), 5.78 (s, 1H), 7.28–7.40 (m, 2H), 7.63 (t, 1H) |
| 6-81 | 1.71–1.89 (m, 4H), 2.31 (s, 3H), 2.45–2.56 (m, 4H), 3.80 (s, 6H), 5.71 (s, 1H), 7.38–7.48 (m, 2H), 7.52 (t, 1H) |
| 6-87 | 1.70–1.87 (m, 4H), 2.42–257 (m, 4H), 3.79 (s, 6H), 4.02 (d, 2H), 4.80 (s, 2H), 5.12–5.22 (m, 2H), 5.70 (s,1H), 5.85–6.00 (m, 1H), 7.22 (d, 2H), 7.44–7.58 (m, 2H) |
| 6-88 | 1.72–1.85 (m, 4H), 2.44–2.55 (m, 4H), 3.40 (s, 3H), 3.79 (s, 6H), 4.73 (s, 2H), 5.70 (s, 1H), 7.21 (d, 1H), 7.44–7.52 (m, 2H) |
| 6-89 | 1.70–1.85 (m, 4H), 2.41–2.50 (m, 4H), 3.80 (s, 6H), 4.53 (s, 2H), 4.86 (s, 2H), 5.70 (s, 1H), 7.21–7.33 (m, 6H), 7.48 (t, H), 7.56 (d, 1H) |
| 6-90 | 1.70–1.85 (m, 4H), 1.85 (s, 3H), 2.44–2.56 (m, 4H), 3.79 (s, 6H), 3.91 (s, 3H), 5.70 (s, 1H), 7.29–7.49 (m, 3H) |
| 6-92 | 1.70–1.85 (m, 4H), 2.40 (t, 1H), 2.45–2.54 (m, 4H), 3.79 (s, 6H), 4.68 (s, 2H), 4.89 (s, 2H), 5.70 (s, 1H), 7.23 (d, 1H), 7.43–7.54 (m, 2H) |
| 6-93 | 0.19 (dd, 2H), 0.45–0.57 (m, 2H), 0.95–1.18 (m, 1H), 1.69–1.89 (m, 4H), 2.42–2.56 (m, 4H), 3.30 (d, 2H), 3.79 (s, 6H), 4.80 (s, 2H), 5.70 (s, 1H), 7.21 (d, 1H), 7.40–7.59 (m, 2H) |
| 6-94 | 1.02 (t, 3H), 1.70–1.85 (m, 4H), 2.02–2.11 (m, 2H), 2.43–2.52 (m, 4H), 3.78 (s, 6H), 5.48 (dd, 1H), 5.69 (s, 1H), 7.23 (t, 1H), 7.50 (t, 1H), 7.62 (d, 1H) |
| 6-99 | 1.13 (t, 3H), 1.78–1.85 (m, 4H), 2.41–2.53 (m, 4H), 2.55 (q, 2H), 3.78 (s, 6H), 5.72 (s, 1H) 7.30–7.41 (m, 2H), 7.50 (t, 1H) |
| 6-120 | 1.70–1.85 (m, 4H), 1.85(s, 3H), 2.40–2.59 (m, 4H), 3.59 (t, 2H), 3.79 (s, 6H), 3.85 (t, 2H), 5.68 (s, 1H), 7.21–7.28 (m, 1H), 7.44–7.57 (m, 2H) |
| 9-48 | 1.20 (t, 6H), 1.70–1.86 (m, 4H), 2.45–2.60 (m, 4H), 3.60 (q, 4H), 3.80 (s, 6H), 5.70 (s, 1H), 6.55 (d, 1H), 7.38 (d, 1H) |
| 9-49 | 1.70–1.88 (m, 4H), 2.47–2.61 (m, 4H), 3.6 (dt, 4H), 3.80 (s, 6H), 3.86 (dt, 4H), 5.73 (s, 1H), 6.75 (d, 1H), 7.48 (d, 1H) |
| 6-100 | 13C-NMR (TMS, CDCl3) δ 115.4 (JC-F = 289 Hz), 185.6(J CCF = 36 Hz) |

The compounds of the present invention have excellent herbicidal activity against weeds grown in upland crop fields either by soil application or foliar application method. In particular, the said compounds can demonstrate higher herbicidal activities on various weeds growing in upland crops, such as foxtails, an umbrella plant, a velvet-leaf and redroot Pigweed, by means of foliar application method, and wherein many compounds having a selectivity to maize, cereals, soybean, cotton, sunflower, etc. are contained.

In the compounds of the present invention, compounds which have a growth retarding activity against useful plants, such as field crops, vegetables, ornamentals and fruit trees, are contained as well.

Further, in the compounds of the present invention, compounds which have an excellent herbicidal activity against weeds grown in paddy rice fields, such as barnyardgrass, *Cyperus difformis, Sagittaria trifolia*, and *Scirpus juncoides*, and have a selectivity to rice plants, are also contained.

In addition, the compounds of the present invention can be applied for weed control in orchards, lawns, railways, vacant lands, etc.

Moreover, in the compounds of the present invention, compounds which have a plant growth regulating activity, a fungicidal activity, an insecticidal activity and an acaricidal activity, are also contained. Again, among the intermediates obtainable in the manufacturing of the compounds of the present invention, compounds having an herbicidal activity are also found.

Herbicides

The herbicides according to the present invention comprise one or more compounds of the present invention as the active ingredient(s). At practical application of the compounds of the present invention, the compounds can be applied alone without combining with other elements. Alternatively, the compounds of the present invent ion can be prepared into any of formulation types normally employed for plant protection chemicals, such as wettable powder, dust, emulsifiable concentrate, suspension and flowable formulation. As an additive or a filler to be used for such formulations, vegetable-origin powder, such as soybean powder and wheat flour, mineral fine powder, such as diatomaceous earth, apatite, gypsum, talc, bentonite, pyrophyllite and clay, and organic or inorganic materials, such as sodium benzoate, urea and Glauber's salt, can be used for a solid-type formulation. In case liquid-type formulations are required, a petroleum fraction, such as kerosine, xylene and solvent naphtha, cyclohexane, cyclohexanone, dimethylformamide, dimethylsulfoxide, alcohol, acetone, trichloroethylene, methylisobutyl ketone, mineral oil, vegetable oil, water, etc. can be used as a solvent. In order to assure uniform and stable physico-chemical properties of such formulations, a surface active agent may be used, if appropriate. As the surface active agent, any of nonionic, anionic, cationic and amphoteric surface active agents can be used, however, nonionic and/or anionic compounds are normally used. And, an appropriate quantity of such surface active agents to be used in the formulation is in a range of from 0.1 to 15% by weight, and preferably from 3 to 10% by weight.

As an appropriate nonionic surface active agent, a compound prepared by adding ethylene oxide by polymerization to a higher alcohol, such as lauryl alcohol, stearyl alcohol and oleyl alcohol; a compound prepared by adding ethylene oxide by polymerization to an alkyl phenol, such as isooctyl phenol and nonyl phenol; a compound prepared by adding ethylene oxide by polymerization to an alkyl naphthol, such as butyl naphthol and octyl naphthol; a compound prepared by adding ethylene oxide by polymerization to a higher alcohol, such as palmitic acid, stearic acid and oleic acid; a higher aliphatic acid ester of polyhydric alcohol, such as sorbitan, and a compound prepared by adding ethylene oxide by polymerization to said higher aliphatic acid ester; a compound prepared by addition polymerization of ethylene oxide and propylene oxide, are given for examples.

As an appropriate anionic surface active agent, an alkyl sulfate ester, such as sodium lauryl sulfate and amine salt of oleyl alcohol sulfate ester; an alkylsulfonate, such as sodium sulfosuccinate dioctyl ester and sodium 2-ethylhexenesulfonate; and an allyl sulfonate, such as sodium isopropylnaphthalene sulfonate, sodium methylenebisnaphthalene sulfonate, sodium lignin sulfonate and sodium dodecylbenzene sulfonate, are given for example.

The content of an active ingredient in the herbicide according to the present invention can differ depending upon formulation types as described above. For example, the content can be in a range of from 5 to 90%, and preferably from 10 to 85%, for a wettable powder formulation; from 3 to 70%, and preferably from 5 to 30%, for an emulsifiable concentrate formulation; and from 0.01 to 30%, and preferably from 0.05 to 10%, for a granular formulation.

The wettable powder and the emulsifiable concentrate obtained as described above can be applied in a form of suspension or emulsion after diluting them with appropriate volume of water. The granules obtained as described above can be directly applied to and/or incorporated into soil without dilution prior to or after germination of weeds. For practical application of the herbicide according to the present invention, an active ingredient in an appropriate amount more than 0.1 g/10 are contained therein could be applied.

The herbicide according to the present invention can be used by mixed with any of other known fungicides, insecticides, acaricides, herbicides, plant growth regulators, etc. In particular, it is possible to reduce the dose of the inventive herbicide to be applied in use by mixing with other herbicide. In this case, such mixing may provide an effect not only to reduce labours required for weeding but also to give higher herbicidal performance because of a synergistic action derived from herbicides mixed together. Mixing of the inventive herbicide with a plurality of other known herbicides is also possible.

For the examples of herbicides to be preferably associated with the inventive herbicide, carbamate-type and thiocarbamate-type herbicides, such as benthiocarb, molinate and dimepiperate; amide-type herbicides, such as butachlor, pretilachlor and mefenacet; diphenyl ether-type herbicides, such as chlomethoxynil and biphenox; triazine-type herbicides, such as atrazine and cyanazine; sulfonylurea-type herbicides, such as chlorsulfuron and sulfometuron-methyl; phenoxyalkane carboxylate-type herbicides, such as MCP and MCPB; phenoxyphenoxypropionic acid-type herbicides, such as diclofop-methyl; pyridyloxyphenoxypropionic acid-type herbicides, such as fluazifop-butyl; dinitroaniline-type herbicides, such as trifluralin and pendimethalin; urea-type herbicides, such as linuron and diuron; benzoylaminopropionic acid-type herbicides, such as benzoylprop-ethyl and flamprop-ethyl; imidazolinone-type herbicides, such as imazaquin; piperophos, daimuron, bentazone, difenzoquat, naproanilide, HW-52 (4-ethoxymethoxybenz-2,3-dichloroanilide), triazophenamide, quinclorac, and cyclohexanedione-type herbicides, such as sethoxydim and clethodim, are given. In addition, a vegetable oil and an oil concentrate may be added to a mixture of the inventive herbicide with one or more of the herbicides exemplified above.

Preparation of Formulation

Now, examples of a formulation suitable to the herbicide according to present invention are given hereinbelow. However, the active ingredients and, types and additional portions of additives used shall be modified to a wide range and shall not be limited to the ones specified in the examples described below. Parts described in the following Formulation Examples means parts by weight.

| Formulation Example 24: Wettable powder | |
| --- | --- |
| The inventive compound | 20 parts |
| White carbon | 20 parts |
| Diatomaceous earth | 52 parts |
| Sodium alkylsulfate | 8 parts |

All materials are uniformly mixed and grinded to fine powder to thereby obtain a wettable powder formulation comprising an active ingredient at 20% concentration.

| Formulation Example 25: Emulsifiable Concentrate | |
| --- | --- |
| The inventive compound | 20 parts |
| Xylene | 55 parts |
| Dimethylformamide | 15 parts |
| Polyoxyethylenephenyl ether | 10 parts |

All materials are mixed and dissolved to obtain an emulsifiable concentrate formulation comprising an active ingredient at 20% concentration.

| Formulation Example 26: Granules | |
| --- | --- |
| The inventive compound | 5 parts |
| Talc | 40 parts |
| Clay | 38 parts |
| Bentonite | 10 parts |
| Sodium alkylsulfate | 7 parts |

All materials are uniformly mixed, grinded to fine powder and granulated into granules having a diameter of from 0.5 to 1.0 mm to thereby obtain a granular formulation comprising an active ingredient at 5% concentration.

Test examples carried out to show a herbicidal activity of the herbicides according to the present invention are now described hereinbelow.

Herbicidal activity is evaluated pursuant to the following criterion, and it is expressed as a herbicidal index.

| Criterion for assessment | |
| --- | --- |
| % of weeds killed | Index for killed-weeds |
| 0% | 0 |
| 20–29% | 2 |
| 40–49% | 4 |
| 60–69% | 6 |
| 80–89% | 8 |
| 100% | 10 |

Indexes 1, 3, 5, 7 and 9 represent an intermediate activity between 0 and 2, 2 and 4, 4 and 6, 6 and 8, and 8 and 10, respectively.
% of Weeds Killed = [(Fresh weight of foliage of weeds untreated − that of treated) ÷ (Fresh weight of foliage of weeds untreated)] × 100

Test Example 1

Foliar Application

In a 200 cm$^2$ planting pot filled with soil, seeds of giant foxtail, redroot Pigweed, Common cocklebur and a velvetleaf are respectively planted and are then covered with slight amount of soil to grow in a greenhouse. When each of the weeds has grown to 5 to 10 cm height, respectively, an emulsion adjusted at 250 ppm by dilution with water from an emulsifiable concentrate formulation of test compound was sprayed to fpliage of the weeds, respectively, at a volume rate of 100 liters/10 are (25 g/10 are as the active ingredient) by using a small sprayer. 3 weeks later, herbicidal performance was checked, respectively, showing the results as in Table 11.

TABLE 11

| | | Herbicidal Index | | | |
| --- | --- | --- | --- | --- | --- |
| Compound No. | Dose g/10 a | Velvetleaf | redroot Pigweed | Common cocklebur | Giant Foxtail |
| 1-2 | 25 | 10 | 10 | 9 | 10 |
| 1-12 | 25 | 10 | 10 | 8 | 9 |
| 1-17 | 25 | 10 | 10 | 9 | 10 |
| 1-21 | 25 | 10 | 10 | 7 | 10 |
| 1-23 | 25 | 10 | 10 | 7 | 10 |
| 1-25 | 25 | 10 | 10 | 8 | 9 |
| 1-28 | 25 | 10 | 9 | 10 | 10 |
| 1-31 | 25 | 10 | 9 | 10 | 8 |
| 1-51 | 25 | 10 | 10 | 8 | 10 |
| 1-54 | 25 | 10 | 10 | 8 | 10 |
| 1-56 | 25 | 8 | 10 | 8 | 10 |
| 1-57 | 25 | 10 | 8 | 8 | 10 |
| 1-60 | 25 | 8 | 10 | 8 | 8 |
| 1-61 | 25 | 8 | 10 | 8 | 0 |
| 1-62 | 25 | 8 | 10 | 8 | 10 |
| 1-63 | 25 | 8 | 10 | 8 | 10 |
| 3-27 | 25 | 10 | 10 | 10 | 10 |
| 3-53 | 25 | 9 | 10 | 9 | 10 |
| 3-67 | 25 | 9 | 10 | 8 | 10 |
| 3-73 | 25 | 10 | 10 | 10 | 10 |
| 3-74 | 25 | 10 | 10 | 9 | 10 |
| 3-82 | 25 | 10 | 10 | 9 | 10 |
| 3-92 | 25 | 9 | 10 | 8 | 8 |
| 3-93 | 25 | 10 | 10 | 9 | 10 |
| 3-94 | 25 | 10 | 10 | 8 | 10 |
| 3-107 | 25 | 10 | 9 | 9 | 10 |
| 3-110 | 25 | 9 | 10 | 9 | 10 |
| 3-115 | 25 | 10 | 10 | 8 | 10 |
| 3-116 | 25 | 10 | 10 | 9 | 10 |
| 3-117 | 25 | 10 | 10 | 8 | 10 |
| 3-119 | 25 | 10 | 10 | 8 | 10 |
| 3-120 | 25 | 10 | 10 | 8 | 10 |
| 3-129 | 25 | 10 | 10 | 8 | 10 |
| 3-130 | 25 | 10 | 10 | 8 | 10 |
| 3-131 | 25 | 10 | 9 | 8 | 10 |
| 3-132 | 25 | 9 | 8 | 9 | 8 |
| 3-133 | 25 | 10 | 10 | 10 | 10 |
| 3-134 | 25 | 8 | 10 | 9 | 10 |

TABLE 11-continued

| Compound No. | Dose g/10 a | Velvetleaf | redroot Pigweed | Common cocklebur | Giant Foxtail |
|---|---|---|---|---|---|
| 3-135 | 25 | 10 | 10 | 7 | 8 |
| 3-139 | 25 | 10 | 10 | 9 | 9 |
| 3-151 | 25 | 8 | 10 | 10 | 10 |
| 3-165 | 25 | 9 | 10 | 8 | 8 |
| 3-167 | 25 | 10 | 10 | 8 | 10 |
| 3-194 | 25 | 10 | 10 | 8 | 10 |
| 3-201 | 25 | 10 | 10 | 8 | 10 |
| 3-202 | 25 | 10 | 10 | 8 | 8 |
| 3-204 | 25 | 10 | 8 | 8 | 10 |
| 3-205 | 25 | 10 | 10 | 8 | 10 |
| 3-206 | 25 | 10 | 10 | 9 | 10 |
| 3-207 | 25 | 10 | 10 | 9 | 10 |
| 3-208 | 25 | 10 | 10 | 8 | 10 |
| 3-210 | 25 | 10 | 10 | 9 | 10 |
| 3-211 | 25 | 10 | 10 | 8 | 10 |
| 3-212 | 25 | 8 | 10 | 8 | 10 |
| 3-213 | 25 | 10 | 10 | 10 | 10 |
| 3-216 | 25 | 10 | 10 | 8 | 10 |
| 3-217 | 25 | 10 | 10 | 8 | 10 |
| 3-219 | 25 | 10 | 10 | 8 | 10 |
| 3-221 | 25 | 10 | 10 | 9 | 10 |
| 3-223 | 25 | 9 | 10 | 9 | 10 |
| 3-225 | 25 | 10 | 10 | 8 | 10 |
| 5-8 | 25 | 8 | 10 | 10 | 8 |
| 5-13 | 25 | 8 | 10 | 9 | 10 |
| 6-2 | 25 | 10 | 10 | 10 | 10 |
| 6-27 | 25 | 10 | 10 | 9 | 8 |
| 6-34 | 25 | 6 | 10 | 9 | 8 |
| 6-37 | 25 | 9 | 10 | 8 | 8 |
| 6-61 | 25 | 10 | 10 | 10 | 10 |
| 7-2 | 25 | 10 | 10 | 10 | 10 |
| 8-1 | 25 | 9 | 9 | 10 | 8 |
| 9-1 | 25 | 10 | 10 | 10 | 10 |
| 9-27 | 25 | 8 | 10 | 8 | 10 |

Test Example 2

Soil Application

In a 250 cm² planting pot filled with soil collected from an upland crop field, seeds of a giant foxtail, a velvetleaf and redroot Pigweed were respectively planted, and are then covered with slight amount of soil. On the next day, a diluted-solution prepared from a wettable powder formulation according to the Example 1 was uniformly sprayed onto soil surface the seeds at a dose of 25 g/10 are calculated as the active ingredient. 20 days later, herbicidal performance was checked, respectively, showing the results as in Table 12.

TABLE 12

| Compound No. | Dose g/10 a | Velvetleaf | redroot Pigweed | Giant Foxtail |
|---|---|---|---|---|
| 1-28 | 25 | 8 | 10 | 8 |
| 1-64 | 25 | 8 | 8 | 10 |
| 1-66 | 25 | 8 | 8 | 10 |
| 3-9 | 25 | 9 | 8 | 10 |
| 3-53 | 25 | 8 | 10 | 10 |
| 3-67 | 25 | 9 | 10 | 10 |
| 3-72 | 25 | 8 | 10 | 8 |
| 3-82 | 25 | 8 | 9 | 10 |
| 3-92 | 25 | 10 | 10 | 10 |
| 3-94 | 25 | 8 | 8 | 8 |
| 3-110 | 25 | 8 | 9 | 10 |
| 3-111 | 25 | 8 | 9 | 10 |
| 3-119 | 25 | 8 | 9 | 7 |
| 3-130 | 25 | 8 | 8 | 8 |
| 3-135 | 25 | 8 | 9 | 10 |
| 3-139 | 25 | 9 | 10 | 8 |
| 3-167 | 25 | 8 | 10 | 10 |
| 3-198 | 25 | 8 | 8 | 8 |
| 3-207 | 25 | 8 | 9 | 10 |
| 3-210 | 25 | 8 | 8 | 9 |
| 3-214 | 25 | 8 | 9 | 10 |
| 3-216 | 25 | 8 | 9 | 9 |
| 3-217 | 25 | 8 | 10 | 9 |
| 3-221 | 25 | 8 | 10 | 9 |
| 3-224 | 25 | 10 | 10 | 9 |
| 6-1 | 25 | 8 | 9 | 9 |
| 6-2 | 25 | 9 | 9 | 9 |
| 6-8 | 25 | 8 | 8 | 10 |
| 6-13 | 25 | 8 | 8 | 9 |
| 6-27 | 25 | 8 | 9 | 8 |
| 6-40 | 25 | 8 | 10 | 9 |
| 6-51 | 25 | 8 | 9 | 9 |
| 6-53 | 25 | 8 | 9 | 8 |
| 6-54 | 25 | 8 | 8 | 8 |
| 6-81 | 25 | 8 | 10 | 9 |
| 6-94 | 25 | 8 | 10 | 9 |
| 6-105 | 25 | 8 | 8 | 10 |
| 9-27 | 25 | 8 | 8 | 10 |

Test Example 3

Foliar Application in Paddy Rice Field

In a 100 cm² planting pot filled with soil collected from a paddy rice field, seeds of barnyardgrass, *Cyperus difformis* and *Scirpus juncoides* are respectively planted after preparing a paddy field for planting, and are then grown in a greenhouse. When each of the weed seeds has grown to 1 leaf stage, respectively, water was flooded into the planting pot up to a height of 3 cm. Then each wettable powder formulation prepared for test compounds was diluted with water, and the dilution was foured dropwise into the planting pot at a dose of 25 g/10 are calculated as an active ingredient, respectively. 3 weeks later, herbicidal performance was checked, respectively, showing the results as in Table 13.

TABLE 13

| Compound No. | Dose g/10 a | Barnyard-grass | *Cyperus difformis* | *Scirpus juncoides* |
|---|---|---|---|---|
| 1-5 | 25 | 8 | 8 | 8 |
| 1-16 | 25 | 10 | 10 | 7 |
| 1-18 | 25 | 10 | 9 | 8 |
| 1-31 | 25 | 9 | 10 | 8 |
| 1-46 | 25 | 10 | 10 | 10 |
| 1-49 | 25 | 10 | 8 | 8 |
| 1-51 | 25 | 8 | 8 | 8 |
| 1-58 | 25 | 8 | 8 | 10 |
| 1-59 | 25 | 9 | 8 | 8 |
| 1-62 | 25 | 8 | 8 | 8 |
| 3-9 | 25 | 8 | 8 | 8 |
| 3-53 | 25 | 8 | 8 | 8 |
| 3-67 | 25 | 10 | 8 | 8 |
| 3-107 | 25 | 10 | 8 | 8 |
| 3-110 | 25 | 10 | 9 | 8 |
| 3-111 | 25 | 10 | 10 | 8 |
| 3-112 | 25 | 10 | 8 | 9 |
| 3-119 | 25 | 10 | 8 | 10 |

TABLE 13-continued

<table>
<tr><th>Compound No.</th><th>Dose g/10 a</th><th colspan="3">Herbicidal Index</th></tr>
<tr><th></th><th></th><th>Barnyard-grass</th><th>Cyperus difformis</th><th>Scirpus juncoides</th></tr>
<tr><td>3-120</td><td>25</td><td>10</td><td>8</td><td>8</td></tr>
<tr><td>3-129</td><td>25</td><td>10</td><td>10</td><td>10</td></tr>
<tr><td>3-130</td><td>25</td><td>10</td><td>10</td><td>10</td></tr>
<tr><td>3-131</td><td>25</td><td>10</td><td>8</td><td>8</td></tr>
<tr><td>3-132</td><td>25</td><td>8</td><td>8</td><td>8</td></tr>
<tr><td>3-135</td><td>25</td><td>10</td><td>9</td><td>8</td></tr>
<tr><td>3-138</td><td>25</td><td>8</td><td>8</td><td>8</td></tr>
<tr><td>3-139</td><td>25</td><td>10</td><td>8</td><td>8</td></tr>
<tr><td>3-144</td><td>25</td><td>10</td><td>8</td><td>8</td></tr>
<tr><td>3-151</td><td>25</td><td>8</td><td>10</td><td>10</td></tr>
<tr><td>3-155</td><td>25</td><td>8</td><td>10</td><td>10</td></tr>
<tr><td>3-156</td><td>25</td><td>8</td><td>8</td><td>8</td></tr>
<tr><td>3-165</td><td>25</td><td>10</td><td>10</td><td>8</td></tr>
<tr><td>3-167</td><td>25</td><td>10</td><td>8</td><td>6</td></tr>
<tr><td>3-173</td><td>25</td><td>10</td><td>9</td><td>8</td></tr>
<tr><td>3-174</td><td>25</td><td>10</td><td>8</td><td>8</td></tr>
<tr><td>3-175</td><td>25</td><td>10</td><td>10</td><td>10</td></tr>
<tr><td>3-176</td><td>25</td><td>10</td><td>8</td><td>9</td></tr>
<tr><td>3-194</td><td>25</td><td>10</td><td>8</td><td>10</td></tr>
<tr><td>3-196</td><td>25</td><td>10</td><td>8</td><td>8</td></tr>
<tr><td>3-197</td><td>25</td><td>10</td><td>8</td><td>8</td></tr>
<tr><td>3-198</td><td>25</td><td>9</td><td>10</td><td>8</td></tr>
<tr><td>3-199</td><td>25</td><td>10</td><td>8</td><td>9</td></tr>
<tr><td>3-200</td><td>25</td><td>10</td><td>8</td><td>8</td></tr>
<tr><td>3-201</td><td>25</td><td>10</td><td>10</td><td>8</td></tr>
<tr><td>3-202</td><td>25</td><td>9</td><td>8</td><td>8</td></tr>
<tr><td>3-204</td><td>25</td><td>9</td><td>8</td><td>8</td></tr>
<tr><td>3-205</td><td>25</td><td>8</td><td>9</td><td>8</td></tr>
<tr><td>3-206</td><td>25</td><td>10</td><td>10</td><td>8</td></tr>
<tr><td>3-207</td><td>25</td><td>10</td><td>10</td><td>8</td></tr>
<tr><td>3-208</td><td>25</td><td>10</td><td>10</td><td>8</td></tr>
<tr><td>3-210</td><td>25</td><td>10</td><td>10</td><td>9</td></tr>
<tr><td>3-214</td><td>25</td><td>10</td><td>10</td><td>9</td></tr>
<tr><td>3-216</td><td>25</td><td>10</td><td>10</td><td>9</td></tr>
<tr><td>3-217</td><td>25</td><td>10</td><td>10</td><td>9</td></tr>
<tr><td>3-219</td><td>25</td><td>10</td><td>10</td><td>8</td></tr>
<tr><td>3-225</td><td>25</td><td>10</td><td>8</td><td>8</td></tr>
<tr><td>4-18</td><td>25</td><td>8</td><td>10</td><td>8</td></tr>
<tr><td>4-24</td><td>25</td><td>10</td><td>10</td><td>10</td></tr>
<tr><td>4-34</td><td>25</td><td>10</td><td>10</td><td>10</td></tr>
<tr><td>5-7</td><td>25</td><td>10</td><td>8</td><td>8</td></tr>
<tr><td>5-8</td><td>25</td><td>8</td><td>8</td><td>8</td></tr>
<tr><td>6-1</td><td>25</td><td>10</td><td>10</td><td>9</td></tr>
<tr><td>6-2</td><td>25</td><td>8</td><td>10</td><td>8</td></tr>
<tr><td>6-4</td><td>25</td><td>10</td><td>10</td><td>8</td></tr>
<tr><td>6-8</td><td>25</td><td>9</td><td>8</td><td>8</td></tr>
<tr><td>6-13</td><td>25</td><td>10</td><td>8</td><td>8</td></tr>
<tr><td>6-35</td><td>25</td><td>10</td><td>10</td><td>10</td></tr>
<tr><td>6-51</td><td>25</td><td>10</td><td>9</td><td>8</td></tr>
<tr><td>6-52</td><td>25</td><td>10</td><td>10</td><td>8</td></tr>
<tr><td>6-53</td><td>25</td><td>10</td><td>8</td><td>8</td></tr>
<tr><td>6-54</td><td>25</td><td>10</td><td>8</td><td>9</td></tr>
<tr><td>6-55</td><td>25</td><td>9</td><td>8</td><td>8</td></tr>
<tr><td>6-66</td><td>25</td><td>10</td><td>8</td><td>8</td></tr>
<tr><td>6-71</td><td>25</td><td>8</td><td>10</td><td>8</td></tr>
<tr><td>6-72</td><td>25</td><td>10</td><td>10</td><td>8</td></tr>
<tr><td>6-73</td><td>25</td><td>10</td><td>10</td><td>8</td></tr>
<tr><td>6-74</td><td>25</td><td>8</td><td>10</td><td>8</td></tr>
<tr><td>6-81</td><td>25</td><td>10</td><td>10</td><td>9</td></tr>
<tr><td>6-88</td><td>25</td><td>10</td><td>10</td><td>10</td></tr>
<tr><td>6-94</td><td>25</td><td>10</td><td>10</td><td>10</td></tr>
<tr><td>6-99</td><td>25</td><td>10</td><td>10</td><td>9</td></tr>
<tr><td>6-105</td><td>25</td><td>10</td><td>10</td><td>8</td></tr>
<tr><td>6-107</td><td>25</td><td>10</td><td>8</td><td>8</td></tr>
<tr><td>6-109</td><td>25</td><td>10</td><td>9</td><td>9</td></tr>
<tr><td>6-113</td><td>25</td><td>9</td><td>9</td><td>8</td></tr>
<tr><td>6-114</td><td>25</td><td>10</td><td>10</td><td>8</td></tr>
<tr><td>9-27</td><td>25</td><td>10</td><td>8</td><td>8</td></tr>
<tr><td>9-35</td><td>25</td><td>8</td><td>8</td><td>8</td></tr>
</table>

Industrial Use of the Invention

As described above, the compounds specified in the present invention have an excellent herbicidal activity by any application method of foliar application, soil application in upland crop fields and foliar application in paddy rice fields, and it is promising to use such compounds as a herbicide.

What is claimed is:

1. A herbicidal composition comprising a compound of formula I:

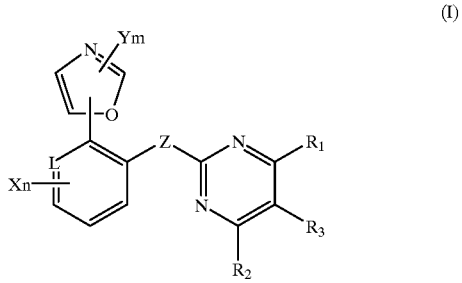

wherein

X represents H, hydroxy, mercapto, halo, cyano, nitro, amino, dimethylamino, methyl, ethyl, isopropyl, tertiarybutyl, halomethyl, cyanomethyl, methylthiomethyl, methylsulfinylmethyl, methylsulfonylmethyl, phenylthiomethyl, phenylsulfonylmethyl, methoxy, isopropoxy, pentyloxy, allyloxy, propynyloxy, methoxymethoxy, methylthiomethoxy, methylsulfonylmethoxy, carboxylpropoxy, ethoxycarbonylmethoxy, ethoxycarbonylpropoxy, carboxyl, methoxycarbonyl, ethoxycarbonyl, isopropoxycarbonyl, acethoxy, toluenesulfonyloxy, benzyl, benzyloxy, dimethoxybenzyloxy, halobenzoyloxy, dimethoxybenzoyloxy, phenyl, halophenyl, ethylphenyl, isopropylphenyl, methyl-halophenyl, ethylcarbamoyloxy, cyclohexylcarbamoyloxy, hexylcarbamoyloxy, ethoxycarbonylthiocarbamoyloxy, methylthio, methylsulfonyl, methylsulfinyl, phenylthio, phenylsulfinyl, phenylsulfonyl, phenoxy optionally substituted with halo, cyano, nitro, amino, dimethyl-amino, methyl, tertiarybutyl methoxy, phenyl or carbamoyl, pyrimidinyloxy optionally substituted with halo, methyl, methoxy or methanesulfony, pyridyloxy optionally substituted with halo, methyl or halomethyl, or dimethoxytriazyl;

Y represents H, halo, methyl, ethyl, propyl, isobutyl, propenyl, butenyl, methoxymethyl, isopropoxymethyl, heptyloxymethyl, methoxyethoxymethyl, methylthiomethyl, ethylthiomethyl, ethylsulfonylmethyl, acethoxymethyl, benzyloxymethyl, ethoxy, benzyl, phenethyl, phenyl, methoxyphenyl, tosyl, dimethylphenyl, halophenyl, aminophenyl, haloacetylaminophenyl, phenoxymethyl, carboxyl, methoxycarbonyl, ethoxycarbonyl, isopropoxycarbonyl, dimethylcarbamoyl, formyl, methoxyiminomethyl, ethoxyiminomethyl, styryl, ethoxycarbonylethenyl, cyanoethenyl, acetoethenyl, naphthyl, pyridyl;

L is nitrogen, or carbon;

Z is O, S, sulfonyl or sulfinyl;

$R_1$ and $R_2$ are independently H, halo, cyano, $C_1$–$C_6$ alkyl, $C_1$–$C_6$ alkoxy, $C_1$–$C_6$ haloalkyl, $C_1$–$C_6$ alkylamino, $C_1$–$C_6$ alkylthio;

$R_3$ is H, halogen, nitro, formyl, $C_1$–$C_6$ alkyl or acyl;

m is 1 or 2;

n is 1, 2, 3 or 4; and one or more component selected from the group consisting of wettable powder, dust, emulsifiable concentrate, vegetable powder, mineral powder, benzoate, urea, Glauber's salt, a petroleum fraction, mineral oil, vegetable oil, water, and a surface active agent.

2. A herbicidal composition comprising a compound having a formula:

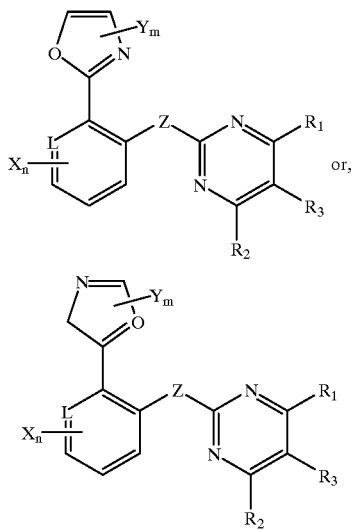

wherein

X represents H hydroxy, mercapto, halo, cyano, nitro, amino, dimethylamino, methyl, ethyl, isopropyl, tertiarybutyl, halomethyl, cyanomethyl, methylthiomethyl, methylsulfinylmethyl, methylsulfonylmethyl, phenylthiomethyl, phenylsulfonylmethyl, methoxy, isopropoxy, pentyloxy, allyloxy, propynyloxy, methoxymethoxy, methylthiomethoxy, methylsulfonylmethoxy, carboxylpropoxy, ethoxycarbonylmethoxy, ethoxycarbonylpropoxy, carboxyl, methoxycarbonyl, ethoxycarbonyl, isopropoxycarbonyl, acethoxy, toluenesulfonyloxy, benzyl, benzyloxy, dimethoxybenzyloxy, halobenzoyloxy, dimethoxybenzoyloxy, phenyl, halophenyl, ethylphenyl, isopropylphenyl, methyl-halophenyl, ethylcarbamoyloxy, cyclohexylcarbamoyloxy, hexylcarbamoyloxy, ethoxycarbonylthiocarbamoyloxy, methylthio, methylsulfonyl, methylsulfinyl, phenylthio, phenylsulfinyl, phenylsulfonyl, phenoxy optionally substituted with halo, cyano, nitro, amino, dimethyl-amino, methyl, tertiarybutyl methoxy, phenyl or carbamoyl, pyrimidinyloxy optionally substituted with halo, methyl, methoxy or methanesulfony, pyridyloxy optionally substituted with halo, methyl or halomethyl, or dimethoxytriazyl;

Y represents H, halo, methyl, ethyl, propyl, isobutyl, propenyl, butenyl, methoxymethyl, isopropoxymethyl, heptyloxymethyl, methoxyethoxymethyl, methylthiomethyl, ethylthiomethyl, ethylsulfonylmethyl, acethoxymethyl, benzyloxymethyl, ethoxy, benzyl, phenethyl, phenyl, methoxyphenyl, tosyl, dimethylphenyl, halophenyl, aminophenyl, haloacetylaminophenyl, phenoxymethyl, carboxyl, methoxycarbonyl, ethoxycarbonyl, isopropoxycarbonyl, dimethylcarbamoyl, formyl, methoxyiminomethyl, ethoxyiminomethyl, styryl, ethoxycarbonylethenyl, cyanoethenyl, acetoethenyl, naphthyl, pyridyl;

L is nitrogen, or carbon;

Z is O or S;

$R_1$ and $R_2$ are independently H, halo, cyano, $C_1$–$C_6$ alkyl, $C_1$–$C_6$ alkoxy, $C_1$–$C_6$ haloalkyl, $C_1$–$C_6$ alkylamino, $C_1$–$C_6$ alkylthio;

$R_3$ is H, halogen, nitro, formyl, $C_1$–$C_6$ alkyl or acyl;

m is 1 or 2;

n is 1, 2, 3 or 4; and one or more component selected from the group consisting of wettable powder, dust, emulsifiable concentrate, vegetable powder, mineral powder, benzoate, urea, Glauber's salt, a petroleum fraction, mineral oil, vegetable oil, water, and a surface active agent.

* * * * *

UNITED STATES PATENT AND TRADEMARK OFFICE
CERTIFICATE OF CORRECTION

PATENT NO. : 6,268,310 B1
DATED : July 31, 2001
INVENTOR(S) : Ayioshi Ueda et al.

It is certified that error appears in the above-identified patent and that said Letters Patent is hereby corrected as shown below:

Title page,
Item [75] Inventors, replace "city of second inventor" with -- Niigata, Japan -- and replace "city of third inventor" with -- Kanagawa, Japan --.

Column 35, Table 1,
No. 1-45, under heading Xn*2 replace "*6-Cl" with -- 6-Cl --

Column 39, Table 3,
No. 3-17, under heading A replace "H" with -- $CR_3$ --
Under heading Z replace "H" with -- O --
Under heading Physical Data remove "O"
No. 3-176, under heading Xn replace "6-Ph-4-Bt" with -- 6-Ph-4-Et --
No. 3-198, under heading $Y_{23}$ replace "$CH_2Pr$" with -- $CH_2Pri$ --
No. 3-201, under heading $Y_{23}$ replace "Pr" with -- $Pr^n$ --

Column 47, Table 3,
Replace "existing formula" with -- 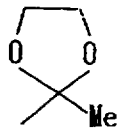

Column 47, Table 4,
No. 4-30, under heading X'n replace "4-P" with -- 4-F --

Column 55, Table 6,
Replace "existing *3 formula" with -- 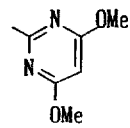

Column 61, Table 8,
No. 8-31, under heading Z replace " " with -- S --
Under Physical Data remove "S"
No. 8-42, under heading Z replace " " with -- O --
Under Physical Data remove "O"
No. 8-46, under heading Z replace " " with -- O --
Under physical data remove "O"

Column 64, Table 9,
Between $Y_5$ and $Y_7$ replace "$Y_8$" with -- $Y_6$ --

UNITED STATES PATENT AND TRADEMARK OFFICE
CERTIFICATE OF CORRECTION

PATENT NO. : 6,268,310 B1
DATED : July 31, 2001
INVENTOR(S) : Ayioshi Ueda et al.

It is certified that error appears in the above-identified patent and that said Letters Patent is hereby corrected as shown below:

Column 66, Table 9,
Between $Y_5$ and $Y_7$ replace "$Y_8$" with -- $Y_6$ --

Column 69,
Line 6, Compound No. 1-11 replace "6.59 (s,1H)" with -- 6.59 (t,1H) --
Line 45, Compound No. 3-195 replace "3.10 (c,2H)" with -- 3.10 (q,2H) --
Line 45, Compound No. 3-195 replace "3.8 (s,6H)" with -- 3.81 (s,6H) --

Column 70,
Line 38, Compound No. 6-89 replace "7.48 (t, H)" with -- 7.48 (t,1H) --

Table 11,
Compound No. 1-61, under Giant Foxtail replace "O" with -- 10 --

Table 12,
Compound No. 3-9, under Velvetleaf replace "9" with -- 8 --

Signed and Sealed this

Fifth Day of February, 2002

Attest:

JAMES E. ROGAN
*Director of the United States Patent and Trademark Office*

*Attesting Officer*